United States Patent
Frazer et al.

(12)

(10) Patent No.: US 6,489,141 B1
(45) Date of Patent: Dec. 3, 2002

(54) NUCLEIC ACID SEQUENCE AND METHODS FOR SELECTIVELY EXPRESSING A PROTEIN IN A TARGET CELL OR TISSUE

(75) Inventors: Ian Hector Frazer, St. Lucia (AU); Jian Zhou, deceased, late of Jindalee (AU), by Xiao Yi Sun, executrix

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 09/479,645

(22) Filed: Jan. 7, 2000

Related U.S. Application Data

(63) Continuation-in-part of application No. PCT/AU98/00530, filed on Jul. 9, 1998.

(30) Foreign Application Priority Data

Jul. 9, 1997 (AU) .................................................. 7765
Sep. 11, 1997 (AU) .................................................. 9467
Jan. 8, 1999 (AU) .................................................. 8078

(51) Int. Cl.[7] .......................... C12N 15/64; C12N 15/66; C12N 15/63; C12N 15/85; C12N 15/87

(52) U.S. Cl. ................ 435/69.1; 435/91.41; 435/91.42; 435/320.1; 435/325; 435/455; 435/91.4; 514/44

(58) Field of Search ..................... 800/302; 435/320.1, 435/252.3, 69.1, 325, 455, 91.42, 91.41, 91.4; 536/23.71; 530/350; 514/44

(56) References Cited

FOREIGN PATENT DOCUMENTS

WO     WO009609378   *  3/1996  ........... C12N/15/09

OTHER PUBLICATIONS

Goldman et al, 1995, J. Mol. Biol., 245: 467–473.*
Roden et al, 1996, J. of Virol., 70: 5875–5883.*
Rosenburg et al, 1993, J of Bacteriol., 175: 716–722.*
Andre et al., 1998, J. Virol. 72:1497–1503.
Bains, 1987, J. Mol. Biol. 197:379–388.
Bible et al., 2000, J. Gen. Virol. 81:1517–1527.
Bulmer, 1987, Nature 325:728–730.
Chiapello et al., 1999, Nucleic Acids Res. 27:2848–2851.
Chiu et al., 1996, Curr. Biol. 6:325–330.
Coulombe and Skup, 1986, Gene 46:89–95.
De Pasquale and Kanduc, 1998, Biochem. Mol. Biol. Int. 45:1005–1009.
Dieci et al., 2000, Protein Expr. Purif. 18:346–354.
Haas et al., 1996, Curr. Biol. 315–324.
Hastings and Emerson, 1983, J. Mol. Evol. 19:214–218.
Hentzen et al., 1981, Nature, 290:267–269.
Holm, 1986, Nucleic Acids Res., 14:3075–3087.
Kelly et al., 1983, Mol. Cell Endocrinol. 29:181–195.
Kim et al, 1997, Gene 199:293–301.
Kniskern et al., 1986, Gene 46:135–141.
Kotsopoulou et al., 2000, J. Virol. 74:4839–4852.
Leboy et al., 1987, 259:558–566.
McLachlan et al., 1984, Nucleic Acids Res. 12:9567–9575.
Mathe et al., 1999, 285:1977–1991.
Nagata et al., 1999, Biochem. Biophys. Res. Comm. 261:445–451.
Nakamura et al., 1991, FEBS Lett. 289:123–125.
O'Neill et al., 1986, Appl. Environ. Microbiol. 52:737–743.
Roche and Sauer, 1999 EMBO, 18:4579–4589.
Saier, 1995, FEBS Lett. 362:1–4.
Sharp et al., 1988, Nucleic Acids Res. 16:8207–8211.
Sharp and Devine, 1989, Nucleic Acids Res. 17:5029–5039.
Sharp and Li, 1986, J. Mol. Evol. 24:28–38.
Sharp et al., 1986, Nucleic Acids Res. 14:5125–5143.
Shields et al., 1988, Mol. Biol. Evol., 1988, 5:704–716.
Skerka et al., 2000, 17:29–41.
Uchijima et al., 1998, J. Immunol. 161:5594–5599.
Vinner et al., 1999, Vaccine 17:2166–2175.
Wu and Saier, 1991, Res. Microbiol. 142:943–949.
Zhang et al., 1991, Gene 105:61–72(Abstract).
Zolotukhin et al., 1996, J. Virol. 70:4646–4654.

* cited by examiner

*Primary Examiner*—Scott D. Priebe
*Assistant Examiner*—Peter Paras, Jr.
(74) *Attorney, Agent, or Firm*—Akin, Gump, Strauss, Hauer & Feld, L.L.P.

(57) ABSTRACT

A synthetic polynucleotide and a method are disclosed for selectively expressing a protein in a target cell or tissue of a mammal. Selective expression is effected by replacing at least one existing codon of a parent polynucleotide encoding a protein of interest with a synonymous codon to produce a synthetic polynucleotide having altered translational kinetics compared to the parent polynucleotide. The synonymous codon is selected such that it has a higher translational efficiency in the target cell or tissue relative to one or more other cells or tissues of the mammal.

60 Claims, 21 Drawing Sheets

Fig. 1A-1

```
                C                 G                           C   G   C   T   C
  1  ATG GCG TTG TGG CAA GGC CAG AAG CTG TAT CTC CCT CCA ACC CCT
      M   A   L   W   Q   G   Q   K   L   Y   L   P   P   T   P
          G
 49  GTA AGC AAG GTG CTT TGC AGT GAA ACC TAT GTG CAA AGA AAA AGC ATT
      V   S   K   V   L   C   S   E   T   Y   V   Q   R   K   S   I
                            C           G           C   C
 97  TTT TAT CAT GCA GAA ACG GAG CGC CTG CTA ACT ATA GGA CAT CCA TAT
      F   Y   H   A   E   T   E   R   L   L   T   I   G   H   P   Y
                      C       C                   G       C
145  TAC CCA GTG TCT ATC GGG GCC AAA ACT GTT CCT AAG GTC TCT GCA AAT  (SauI)
      Y   P   V   S   I   G   A   K   T   V   P   K   V   S   A   N
                      C       G           C
193  CAG TAT AGG GTA TTT AAA ATA CAA CTA CCT GAT CCC AAT CAA TTT GCA
      Q   Y   R   V   F   K   I   Q   L   P   D   P   N   Q   F   A
      G                                   C
241  CTA CCT GAC AGG ACT GTT CAC AAC CCA AGT AAA GAG CGG CTG GTG TGG  (BalI)
      L   P   D   R   T   V   H   N   P   S   K   E   R   L   V   W
```

```
              G   C  C                                           C             C  C  C
289  CCA GTC ATA GGT GTG CAG GTG TCC AGA GGG CAG CCT CTT GGA GGT ACT
     P   V   I   G   V   Q   V   S   R   G   Q   P   L   G   G   T
     ─                                                           ─
           G                                          G
337  GTA ACT GGG CAC CCC ACT TTT AAT GCT TTG CTT GAT GCA GAA AAT GTG
     V   T   G   H   P   T   F   N   A   L   L   D   A   E   N   V

C                     G     C  C
385  AAT AGA AAA GTC ACC AAC CAA CAG ATT CTG ACA GAT GAC AGG AAA (StuI)
     N   R   K   V   T   N   Q   Q   I   L   T   D   D   R   K
                                                              ACA GGC
                                                              T   G
                                                                  ─
         G                    G       G   C
433  CTA GAT GCT AAG CAA CAA ACA GCC CGT CCA TGT ACT ACC CCT GCT
     L   D   A   K   Q   Q   T   A   R   P   C   T   T   P   A
     ───                                                   ─

481  GAA GGG GAA TAT TGG ACA ACA GAC GTT CCA TGT GAT CGT CTA (XbaI)
     E   G   E   Y   W   T   T   D   V   P   C   D   R   L
                                                     ─── ───

C                   G  G           C
529  GAA AAT GGC GCC TGC CCT CTT GAA TTA AAA AAC CAC ATA GAA
     E   N   G   A   C   P   L   E   L   K   N   H   I   E
     ─
```

```
                                                                              (NaeI)
577  GAT GGG GAT ATG ATG GAA ATT GGG TTT GGT GCA GCC AAC TTC AAA GAA
      D   G   D   M   M   E   I   G   F   G   A   A   N   F   K   E

625  ATT AAT GCA AGT AAA TCA GAT CTA CCT CTT GAC ATT GCA AAT GAG ATC
      I   N   A   S   K   S   D   L   P   L   D   I   Q   N   E   I
                            C                   G       C
673  TGC TTG TAC CCA GAC TAC CTC AAA ATG GCT GAG GAC GCT GCT GGT AAT
      C   L   Y   P   D   Y   L   K   M   A   E   D   A   A   G   N
          C   C               C           G   C   C   C
721  AGC ATG TTC TTT GCA AGG GGG TCG GAG AAA GAA CAG GTG TAT GTT AGA CAC ATC
      S   M   F   F   A   R   G   S   E   K   E   Q   V   Y   V   R   H   I
          G   C   C           C               G           G
769  TGG ACC AGA GGG GGC AAA AAT GGG GAT GCC ACC GCC CCT ACC ACA GAT TTT TAT
      W   T   R   G   G   K   N   G   D   A   T   A   P   T   T   D   F   Y
      G           C       C               C   G   C       G   C
817  TTA AAG AAT AAT AAA GGG GAT GCC ACC CTT AAA ATA CCC AGT GTG CAT
      L   K   N   N   K   G   D   A   T   L   K   I   P   S   V   H
```

```
                                                                                          (SpeI)
      C   C       C           C   C   C   G   C   C   C   C
 865 TTT GGT AGT CCC AGT GGC TCA CTA GTC ACT GAT AAT CAA ATT TTT
      F   G   S   P   S   G   S   L   V   T   D   N   Q   I   F

C                   G       C
 913 AAT CGG CCC TAC TGG CTA TTC CGT GCC CAG GGC ATG AAC AAT GGA ATT
      N   R   P   Y   W   L   F   R   A   Q   G   M   N   N   G   I

C   C       C   C   C   G       C           C       C  (BsaAI)
 961 GCA TGG AAT AAT TTA TTG TTT TTA ACA GTG GGG GAC AAT ACA CGT GGT
      A   W   N   N   L   L   F   L   T   V   G   D   N   T   R   G

C   C       G           C           G       G   G   C   G
1009 ACT AAT CTT ACC ATA AGT GTA GCC TCA GAT GGA ACC CCA CTA ACA GAG
      T   N   L   T   I   S   V   A   S   D   G   T   P   L   T   E

C           C                           G           C
1057 TAT GAT AGC TCA AAA TTC AAT GTA TAC CAT AGA CAT ATG GAA GAA TAT
      Y   D   S   S   K   F   N   V   Y   H   R   H   M   E   E   Y

C   C       C       G   C       G       C       G  (NheI)
1105 AAG CTA GCC TTT ATA TTA GAG CTA TGC TCT GTG GAA ATC ACA GCT CAA
      K   L   A   F   I   L   E   L   C   S   V   E   I   T   A   Q
```

Fig. 1A-4

```
                                                               C
1153 ACT GTG TCA CAT CTG CAA GGA CTT ATG CCC TCT GTG CTT GAA AAT TGG
      T   V   S   H   L   Q   G   L   M   P   S   V   L   E   N   W
                          C           G   C       G   G           C
                                                                           (ClaI)
1201 GAA ATA GGT GTG CAG CCT ACC TCA TCG ATA TTA GAG GAC ACC TAT
      E   I   G   V   Q   P   T   S   S   I   L   E   D   T   Y
          C       C           C   C               C   G
                                                       C
1249 TAT ATA GAG TCT CCT GCA ACT AAA TGT GCA AGC AAT GTA ATT CCT
      Y   I   E   S   P   A   T   K   C   A   S   N   V   I   P
          C           C   C   C           G           C   G
                                                                   G
1297 CGC TAT GCA CCT TAT GCA GGG TTT AAG TTT TGG AAC ATA GAT CTT
      R   Y   A   P   Y   A   G   F   K   F   W   N   I   D   L
                  C                                   C   C
                                                                           (StyI)
1345 GCA AAA GAA GAC CTT TCT TTG GAC CAA TTT CAA TTT CCC TTG GGA AGA AGA
      A   K   E   D   L   S   L   D   Q   F   Q   F   P   L   G   R   R
      G           G               C           C       C
                                                                                   G
1393 TTT TTA GCA CAG CAA GGG GCA GGA TGT TCA ACT GTG AGA AAA CGA AGA
      F   L   A   Q   Q   G   A   G   C   S   T   V   R   K   R   R
      C G               C           C       C                   C
```

Fig. 1A-5

```
                       C        G    G     C           C           C     G              G  G  G  G  G     G
1441 ATT AGC CAA AAA ACT TCC AGT AAG CCT GCA AAA AAA AAA AAA AAA AAA TAA
       I   S   Q   K   T   S   S   K   P   A   K   K   K   K   K   K   -
```

Fig. 1A-6

```
                                       C              G              C
 1  ATG AGT GCA CGA AAA AGA GTA AAA CGT GCC AGT GCC TAT GAC CTG TAC
      M   S   A   R   K   R   V   K   R   A   S   A   Y   D   L   Y
             C                     G   C                     C
49  AGG ACC TGC AAG CAA GCG GGC ACA TGT CCA CCA GAT GTG ATA CGA AAG
      R   T   C   K   Q   A   G   T   C   P   P   D   V   I   R   K
       G              C                            G       C     C     C     G
97  GTA GAA GGA GAT ACT ATA GCA GAT AAA ATT TTG AAA TTT GGG GGT CTT
      V   E   G   D   T   I   A   D   K   I   L   K   F   G   G   L
       C              C       C        G           C                    C
145 GCA ATC TAC TTA GGA GGG CTA GGA ATA GGA ACA TGG TCT ACT GGA AGG   (AccI)
      A   I   Y   L   G   G   L   G   I   G   T   W   S   T   G   R
```

```
                                                                                                              (BamHI)
193 GTG GCC GCA GGT GGA TCA CCA AGG TAC ACA CCA CTC CGA ACA GCA GGG
     V   A   A   G   G   S   P   R   Y   T   P   L   R   T   A   G
         C   C   C       C                   C   C       C   C   C

241 TCC ACA TCA TCG CTT GCA TCA ATA GGA TCC AGA GCT GTA ACA GCA GGG
     S   T   S   S   L   A   S   I   G   S   R   A   V   T   A   G
         C   C       TCC        C               C           C
                 AGT

289 ACC CGC CCC AGT ATA GGT GCG TCA ATT CCT TTA GAC ACC CTT GAA ACT
     T   R   P   S   I   G   A   S   I   P   L   D   T   L   E   T
             C   C       C       C   C       C G   G

337 CTT GGG GCC TTG CGT ATA GGG GAT GTG TAT GAG GAC ACT GTG CTA GAG
     L   G   A   L   R   I   G   D   V   Y   E   D   T   V   L   E
             C       C       T       C   C       G       C   C

385 GCC CCT GCA GTC ACT CCT GAT GCT GTT CCT GCA GAT TCA GGG CTT
     A   P   A   V   T   P   D   A   V   P   A   D   S   G   L
     C       C   C       G   C   C   C           C   C   C   G
                                                                    (PstI)

433 GAT GCC CTG TCC ATA GGT ACA GAC TCG ACG GAG ACC CTC ATT ACT
     D   A   L   S   I   G   T   D   S   T   E   T   L   I   T
         C                                   G   C       G   C   C
```

```
                                                                          (SauI)
                                                         G       C        G
          G                 C                    A       C       A        C
481  CTG CTA GAG CCT GAG GGT CCC GAG GAC ATA GCG GTT CTT GAG CTG CAA
      L   L   E   P   E   G   P   E   D   I   A   V   L   E   L   Q

C                 G           C
529  CCC CTG GAC CGT CCA ACT TGG CAA GTA AGC AAT GCT GTT CAT CAG TCC
      P   L   D   R   P   T   W   Q   V   S   N   A   V   H   Q   S

C                         C       C        G
          C                  TCC                        C       C        G
577  TCT GCA TAC CAC GCC CCT CTG CAG CTG CAA TCG TCC ATT GCA GAA ACA
      S   A   Y   H   A   P   L   Q   L   Q   S   S   I   A   E   T (AvaI)
                                                         C
625  TCT GGT TTA GAA AAT ATT TTT GTA GGA GGC TCG GGT TTA GGG GAT ACA
      S   G   L   E   N   I   F   V   G   G   S   G   L   G   D   T

C       C       G                      C       C       C
673  GGA GGA GAA AAC ATT GAA CTG ACA TAC TTC GGG TCC CCA CGA ACA AGC
      G   G   E   N   I   E   L   T   Y   F   G   S   P   R   T   S

C              TCC                 C       G       C       C
                                                              C       C       G
721  ACG CCC CGC AGT ATT GCC TCT AAA TCA CGT GGC ATT TTA AAC TGG TTC
      T   P   R   S   I   A   S   K   S   R   G   I   L   N   W   F
```

Fig. 1B-3

```
 769 AGT AAA CGG TAC TAC ACA CAG GTG CCC ACG GAA GAT CCT GAA GTG TTT  (BanI)
       C   G                       C       C               C   C
      S   K   R   Y   Y   T   Q   V   P   T   E   D   P   E   V   F

817 TCA TCC CAA ACA TTT GCA AAC CCA CTG TAT GAA GCA GAA CCA GCT GTG
       C   C       G   C   C                   C   G   C   C   C
      S   S   Q   T   F   A   N   P   L   Y   E   A   E   P   A   V

865 CTT AAG GGA CCT AGT GGA CGT AGT GGG ACA GAG GTG GTT CAG TAT AAA CCT
           C           C                   C       G       C   C
      L   K   G   P   S   G   R   S   G   T   E   V   V   Q   Y   K   P

913 GAT ACA CTT ACA ACA CGT AGC GGG ACA GAG GTG GGA CCA CAG CTA CAT  (BsaAI)
           C                   C                       G       C   G
      D   T   L   T   T   R   S   G   T   E   V   G   P   Q   L   H

961 GTC AGG TAC TCA AGT ACT ATA CAT GAA GAT GTA GAA GCA ATC CCC
       G   C   C   C   TCC          C           C   G   T
      V   R   Y   S   L   T   I   H   E   D   V   E   A   I   P

1009 TAC ACA GTT GAT GAA AAT ACA CAG GGA CTT GCA TTC GTA CCC TTG CAT
       C   G               G   C   C   C       C   G                C
      Y   T   V   D   E   N   T   Q   G   L   A   F   V   P   L   H
```

Fig. 1B-4

```
                                                                                                    (SacI)
       G      G     C     C     C          C   G  C  C   C      C
1057 GAG  GAG  CAA  GCA  GGT  TTT  GAG  GAG  ATA  GAA  TTA  GAT  GAT  TTT  AGT  GAG
       E    E    Q    A    G    F    E    E    I    E    L    D    D    F    S    E

C     C           C           C          G     C     C      C
1105 ACA  CAT  AGA  CTG  CTA  CCT  CAG  AAC  ACC  TCT  ACA  CCT  GTT  GGT  AGT
       T    H    R    L    L    P    Q    N    T    S    T    P    V    G    S

C     G     C          G     C     T     C          G     C     C     C
1153 GGT  GTA  CGA  AGA  AGC  CTC  ATT  CCA  ACT  CGA  GAA  TTT  AGT  GCA  ACA  CGG
       G    V    R    R    S    L    I    P    T    R    E    F    S    A    T    R (NheI)
                C     G     C          C           C     C     G     C     C
1201 CCT  ACA  GGT  GTT  GTA  ACC  TAT  GGC  TCA  CCT  GAC  AGT  TCT  GCT  AGC
       P    T    G    V    V    T    Y    G    S    P    D    S    S    A    S

C                 G     G                 C     G           C
1249 CCA  GTT  ACT  GAC  CCT  GAT  TAC  ACT  TTT  AGT  CCT  GAC  ATC  GAT  GAC
       P    V    T    D    P    D    Y    T    F    S    P    D    I    D    D

C     C     C                                   C     G                 C
1297 ACT  ACT  ACA  CCA  ATC  ATA  ATT  ATT  GAT  GGG  CAC  ACA  GTT  GAT  TTG
       T    T    T    P    I    I    I    I    D    G    H    T    V    D    L
```

Fig. 1B-5

```
                              C                                    C       G   C   G
1345 TAC AGC AGT AAC TAC ACC TTG CAT CCC TCC TTG AGG AAA CGA AAA
      Y   S   S   N   Y   T   L   H   P   S   L   R   K   R   K

G   C   G
1393 AAA CGG AAA CAT GCC TAA
      K   R   K   H   A   -
```

Fig. 1B-6

```
          T   A   G   A           A       T   A   G       T   A   A
 1 ATG AGC AAG GGC GAG GAA CTG TTC ACT GGC GTG GTC CCA ATT CTC GTG
    M   S   K   G   E   E   L   F   T   G   V   V   P   I   L   V

A               G               A                       T   G   A
49 GAA CTG GAT GGC GAT GTG AAT GGG CAC AAA TTT TCT GTC AGC GGA GAG
    E   L   D   G   D   V   N   G   H   K   F   S   V   S   G   E

G           G               A               T       A
97 GGT GAA GGT GAT GCC ACA TAC GGA AAG CTC ACC CTG AAA TTC ATC TGC
    G   E   G   D   A   T   Y   G   K   L   T   L   K   F   I   C
```

```
                                                                                                        (NcoI)
         A       A   G       A       A           A           T               T   A   A   A   T
145  ACC ACT GGA AAG CTC CCT GTG CCA TGG CCA ACA CTG ACT ACC TTC
      T   T   G   K   L   P   V   P   W   P   T   L   T   T   F

A                       T   T                               A   A
193  AGT TCT TAT GGC GTG CAG TGC TTT TCC AGA ATG TAC CCA GAC CAT ATG AAG CAG
      S   S   Y   G   V   Q   C   F   S   R   M   Y   P   D   H   M   K   Q
                                                                                                        (AvaI)
             T               T           T       A               G                   A       A
241  CAT GAC TTT TTC AAG AGC GCC ATG CCC GAG GGC TAT GTG CAG GAG AGA
      H   D   F   F   K   S   A   M   P   E   G   Y   V   Q   E   R

A   A   T       T                   T               A           A           A       G
289  ACC ATC TTT TTC AAA GAT GAC GGG AAC TAC AAG ACC CGC GCT GAA GTC
      T   I   F   F   K   D   D   G   N   Y   K   T   R   A   E   V
                                                                                                        (SacI)
         A   T   G       A           G   T       A               A           C       A   G   A
337  AAG TTC GAA GGT GAC ACC CTG GTG AAT AGA ATC GAG CTG AAG GGC ATT
      K   F   E   G   D   T   L   V   N   R   I   E   L   K   G   I

T           A           A               G                       A           T       A   T
385  GAC TTT AAG GAG GAT GGA AAC ATT CTC GGC CAC AAG CTG GAA TAC AAC
      D   F   K   E   D   G   N   I   L   G   H   K   L   E   Y   N
```

Fig. 1C-3

```
433  TAT AAC TCC CAC AAT GTG TAC ATC ATG GCC GAC AAG AAT GGC
      Y   N   S   H   N   V   Y   I   M   A   D   K   N   G

481  ATC AAG GTC AAC TTC AAG ATC AGA CAC AAC ATT GAG GAT GGA TCC GTG   BamHI
      I   K   V   N   F   K   I   R   H   N   I   E   D   G   S   V

529  CAG CTG GCC CTC GAC CAT TAT CAA AAC CAT AAC ACT CCA ATT GAG GAC GGC CCT
      Q   L   A   L   D   H   Y   Q   N   H   N   T   P   I   E   D   G   P

577  GTG CTC CTC CCA GAC TAC CTG TCC ACC CAG ACC AGT TCT GCC CTG TCT
      V   L   L   P   D   Y   L   S   T   Q   T   S   A   L   S

625  AAA GAT CCC AAC GAA AAG AGA GAC CAC ATG GTC CTG CTG GAG TTT GTG   (XhoI)
      K   D   P   N   E   K   R   D   H   M   V   L   L   E   F   V

673  ACC GCT GGG ATC ACA CAT GGC ATG GAC GAG CTG TAC AAG TGA
      T   A   G   I   T   H   G   M   D   E   L   Y   K   —
```

NUCLEIC ACID SEQUENCE AND METHODS FOR SELECTIVELY EXPRESSING A PROTEIN IN A TARGET CELL OR TISSUE

This application is a continuation-in-part application of co-pending International Patent Application No. PCT/AU98/00530 filed Jul. 9, 1998, which designates the United States, and which claims priority of Australian Patent Application Nos. PO7765 filed Jul. 9, 1997 and PO9467 filed Sep. 11, 1997.

FIELD OF THE INVENTION

This invention relates generally to gene therapy. More particularly, the present invention relates to a synthetic polynucleotide and to a method for selectively expressing a protein in a target cell or tissue in which at least one existing codon of a parent polynucleotide encoding the protein has been replaced with a synonymous codon. The invention also relates to production of virus particles using one or more synthetic polynucleotides and the method according to the invention.

BACKGROUND OF THE INVENTION

While gene therapy is of great clinical interest for treatment of gene defects, this therapy has not entered into mainstream clinical practice, at least in part because selective delivery of genes to target tissues has proven extremely difficult. Currently, viral vectors are used, particularly retroviruses and adenovirus, which are to some extent selective. However, many vector systems are by their nature unable to produce stable integrants and some also invoke immune responses thereby preventing effective treatment. Alternatively, "naked" DNA is packaged in liposomes or other similar delivery systems. A major problem to be overcome is that such gene delivery systems themselves are not tissue selective, whereas selective targeting of genes to particular tissues would be desirable for many disorders (e.g., cancer therapy). While use of tissue specific promoters to target gene therapy has been effective in some animal models it has proven less so in man, and selective tissue specific promoters are not available for a wide range of tissues.

The current invention has arisen unexpectedly from recent investigations exploring why papillomavirus (PV) late gene expression is restricted to differentiated keratinocytes. In this regard, it is known that PV late genes L1 and L2 are only expressed in non-dividing differentiated keratinocytes (KCs). Many investigators including the present inventors have been unable to detect significant PV L1 and L2 protein expression when these genes are transduced or transfected into undifferentiated cultured cells, using a range of conventional constitutive viral promoters including retroviral long terminal repeats (LTRs) and the strong constitutive promoters of CMV and SV40.

PV L1 mRNA can however be efficiently translated in vitro using rabbit reticulocyte cell lysate, suggesting that there are no cellular inhibitors in the lysate interfering with translation of L1. The major difference between the in vitro and in vivo translation systems is that L1 comprises the dominant L1 mRNA in in vitro translation reactions, while it constitutes a minor fraction among the cellular mRNAs in intact cells.

In vivo, PV late proteins are not produced in undifferentiated KC. However, they are expressed in large quantity in highly differentiated KC. The mechanism of this tight control of late gene expression has been poorly understood, and searches by many groups for KC specific PV gene transcriptional control proteins have been unrewarding.

Blockage of translation of L1 mRNA in vivo has been attributed to sequences within the L1 ORF (Tan et al. 1995, *J. Virol.* 69 5607–5620; Tan and Schwartz, 1995, *J. Virol.* 69 2932–2945). By using a Rev and Rev-responsive element of HIV, such inhibition could be overcome (Tan et al. 1995, supra) . Accordingly, the inventors examined whether removal of putative "inhibitory sequences" in the L1 ORF would allow production of L1 protein in undifferentiated cells. Deletion mutagenesis of BPV L1 to remove putative inhibitory sequences and expression of resultant deletion mutants in CV-1 cells revealed surprisingly that despite expression of L1 mRNA, L1 protein could not be detected.

In view of the foregoing, it has been difficult hitherto to understand how papillomaviruses produce large amounts of L1 protein in the late stage of their life cycle using this apparently "untranslatable" gene. The present inventors have discovered the mechanism by which L1 protein is expressed in the late stage of the life cycle of this virus, and have also discovered a method of general application whereby polynucleotides can be designed or modified in order to effect selective expression of a protein in a target cell or tissue.

SUMMARY OF THE INVENTION

Accordingly, in one aspect of the invention, there is provided a method of constructing a synthetic polynucleotide from which a protein is selectively expressible in a target cell of a mammal, relative to another cell of the mammal, said method comprising:

selecting a first codon of a parent polynucleotide for replacement with a synonymous codon which has a higher translational efficiency in said target cell than in said other cell; and replacing said first codon with said synonymous codon to form said synthetic polynucleotide.

Preferably, said first codon and said synonymous codon are selected by:

comparing translational efficiencies of individual codons in said target cell relative to said other cell; and selecting said first codon and said synonymous codon based on said comparison.

A translational efficiency of a codon may be determined by any suitable technique. In a preferred embodiment, the translational efficiency of a codon is measured by:

introducing into said target cell and into said other cell, a synthetic construct comprising a reporter polynucleotide fused in frame with a tandem repeat (e.g. 2, 3, 4, 5, 6, or 7 or more) of said individual codon, wherein said reporter polynucleotide encodes a reporter protein, and wherein said synthetic construct is operably linked to a regulatory polynucleotide; and comparing expression of said reporter protein in said target cell and in said other cell to determine the translational efficiency of said individual codon in said target cell relative to said other cell.

Preferably, the above method is further characterized by:

introducing the synthetic construct into a progenitor cell of a cell selected from the group consisting of said target cell and said other cell; and producing said target cell from said progenitor cell, wherein said cell contains said synthetic construct.

Suitably, this method is further characterized by:

introducing the synthetic construct into a progenitor cell of a cell selected from the group consisting of said target cell and said other cell; and growing an organism or part thereof from said progenitor cell, wherein said organism comprises said cell containing said synthetic construct.

The above method may be further characterized by the step of introducing the synthetic construct into an organism or part thereof such that said synthetic construct is introduced into said target cell or said other cell.

Preferably, said synonymous codon corresponds to a reporter construct from which the reporter protein is expressed in said target cell at a level that is at least 110%, preferably at least 200%, more preferably at least 500%, and most preferably at least 1000%, of that expressed from the same reporter construct in said other cell.

In an alternate embodiment, the translational efficiency of a codon is compared by measuring the abundance of an iso-tRNA corresponding to said individual codon in said target cell relative to said other cell.

Preferably, said synonymous codon corresponds to an iso-tRNA which is in higher abundance in the target cell relative to said other cell.

Preferably, selecting said first codon and said synonymous codon comprises:
  measuring abundance of different iso-tRNAs in said target cell relative to said other cell; and
  selecting said first codon and said synonymous codon based on said measurement, wherein said synonymous codon corresponds to an iso-tRNA which is in higher abundance in said target cell than in said other cell.

Advantageously, said synonymous codon corresponds to an iso-tRNA that is present in said target cell at a level which is at least 110%, preferably at least 200%, more preferably at least 500%, and most preferably at least 1000%, of the level that is present in said other cell.

Alternatively, the step of selecting may be characterized in that a synonymous codon according to the invention is selected from the group consisting of (1) a codon used at relatively high frequency by genes, preferably highly expressed genes, of a said target cell or tissue, (2) a codon used at relatively high frequency by genes, preferably highly expressed genes, of the mammal, (3) a codon used at relatively low frequency by genes of a said one or more other cells or tissues, and (4) a codon used at relatively low frequency by genes of another organism.

The step of selecting may be characterized in that a first codon according to the invention is selected from the group consisting of (a) a codon used at relatively high frequency by genes, preferably highly expressed genes, of a said one or more other cells or tissues, (b) a codon used at relatively low frequency by genes of a said target cell or tissue, (c) a codon used at relatively low frequency by genes of the mammal, and (d) a codon used at relatively high frequency by genes of another organism.

In a preferred embodiment, the method further includes the step of selecting the first codon and the synonymous codon such that said protein is expressed from said synthetic polynucleotide in said target cell or tissue at a level which is at least 110%, preferably at least 200%, more preferably at least 500%, and most preferably at least 1000%, of that expressed from said parent polynucleotide in said target cell or tissue.

Preferably, the other cell is a precursor cell of the target cell. Alternatively, the other cell may be a cell derived from the target cell.

In another aspect, the invention provides a synthetic polynucleotide constructed according to any one of the above methods.

Suitably, said synonymous codon(s) are selected from the group consisting of gca (Ala), cuu (Leu) and cua (Leu), when said target cell is a differentiated cell, and more preferably when said target cell is a differentiated keratinocyte.

Synonymous codons for higher level expression of a protein in an undifferentiated cell, preferably an undifferentiated keratinocyte, are suitably selected from the group consisting of cga (Arg), cci (Pro) and aag (Asn).

Synonymous codon(s) are preferably selected from the group consisting of aga (Arg), cgg (Arg), tgc (Cys), gga (Gly), ggc (Gly), ccg (Pro), cga (Pro), aca (Thr), acg (Thr), and act (Thr), when said target cell is an undifferentiated cell, and preferably an undifferentiated epithelial cell.

Suitably, the first codon is selected from the group consisting of agg (Arg), tgt (Cys), ggg (Gly), ggt (Gly), ccc (Pro), cct (Pro), and acc (Thr), when said target cell is an undifferentiated cell, and preferably an undifferentiated epithelial cell.

In yet another aspect, the invention resides in a method for selectively expressing a protein in a target cell or tissue of a mammal, said method comprising:
  replacing a first codon of a parent polynucleotide encoding said protein with a synonymous codon to produce a synthetic polynucleotide having altered translational kinetics compared to said parent polynucleotide, such that said protein is expressible in said target cell, but such that said protein is not substantially expressible in another cell of the mammal; and
  introducing into a cell selected from the group consisting of said target cell and a precursor of said target cell, said synthetic polynucleotide operably linked to a regulatory polynucleotide. The protein is thereby selectively expressed in said target cell.

Preferably, said synonymous codon has a higher translational efficiency in said target cell than in said other cell.

In yet another aspect, the invention provides a method of expressing a protein in a target cell from a first polynucleotide, said method comprising:
  introducing into a cell selected from the group consisting of said target cell and a precursor of said target cell, a second polynucleotide encoding an iso-tRNA, wherein said second polynucleotide is operably linked to a regulatory polynucleotide, and wherein said iso-tRNA is normally in relatively low abundance in said target cell and corresponds to a codon of said first polynucleotide. The protein is thereby expressed in the target cell.

In a further aspect, the invention extends to a method of producing a virus particle in a cycling eukaryotic cell, wherein said virus particle comprises a protein necessary for assembly of said virus particle, and wherein said protein is not expressed in said cell from a parent polynucleotide at a level sufficient to permit virus assembly therein, said method comprising:
  replacing a first codon of said parent polynucleotide with a synonymous codon to produce a synthetic polynucleotide having altered translational kinetics compared to said parent polynucleotide, such that said protein is expressible from said synthetic polynucleotide in said cycling eukaryotic cell at a level sufficient to permit virus assembly therein; and
  introducing into a recipient cell selected from the group consisting of said cycling eukaryotic cell and a precursor of said cycling eukaryotic cell said synthetic polynucleotide operably linked to a regulatory polynucleotide, wherein said recipient cell comprises said protein necessary for assembly of said virus particle. The protein is thereby expressed and said virus particle is produced in said cycling eukaryotic cell.

In yet a further aspect of the invention, there is provided a method of producing a virus particle in a cycling cell, wherein said virus particle comprises at least one protein necessary for assembly of said virus particle, wherein said protein is not expressed in said cell from a parent polynucleotide at a level sufficient to permit virus assembly therein, and wherein a codon of said parent polynucleotide is rate limiting for the production of said protein, said method comprising introducing into said cell a polynucleotide capable of expressing therein an iso-tRNA specific for said codon. The virus particle is thereby produced in the cycling cell.

The invention also includes cells, vectors, and viruses made by any of the methods described above, and pharmaceutical compositions comprising one or more such cells, vectors, and viruses together with a pharmaceutically acceptable carrier.

BRIEF DESCRIPTION OF THE DRAWINGS

FIG. 1A, comprising FIGS. 1A-1 through 1A-6, depicts the nucleotide sequence (SEQ ID NO:1) and deduced amino acid sequence (SEQ ID NO:2) of BPV1 L1. Amino acid residues (in single letter code) are presented below the second nucleotide residue of each codon. Mutations introduced into the genes are indicated above the corresponding nucleotide residues of the original sequence. Horizontal lines indicate the sites and enzymes used for cloning. This replacement of nucleotide residues resulted in a nucleic acid sequence encoding BPV-1 L1 polypeptide with an amino acid sequence identical to the wild type, but having synonymous codons that are frequently used by mammalian genes.

FIG. 1B, comprising FIGS. 1B-1 through 1B-6, shows the nucleotide sequence (SEQ ID NO:5) and deduced amino acid sequence (SEQ ID NO:6) relating to BPV1 L2 ORF. Amino acid residues (in single letter code) are presented below the second nucleotide of each codon. Mutations introduced into the genes are indicated above the corresponding nucleotide residues of the original sequence. Horizontal lines indicate the sites and enzymes used for cloning. This replacement of nucleotide residues resulted in a nucleic acid sequence encoding BPV-1 L2 polypeptide with an amino acid sequence identical to the wild type, but having synonymous codons that are frequently used by mammalian genes.

FIG. 1C, comprising FIGS. 1C-1 through 1C-3, depicts the nucleotide sequence (SEQ ID NO:9) and deduced amino acid sequence (SEQ ID NO:10) of green fluorescent protein (GFP). Amino acid residues (in single letter code) are presented below the second nucleotide of each codon. Mutations introduced into the genes are indicated above the corresponding nucleotide residues of the original sequence. Horizontal lines indicate the sites and enzymes used for cloning. This replacement of nucleotide residues resulted in a nucleic acid sequence encoding GFP polypeptide with an amino acid sequence identical to the native sequence modified for optimal expression in eukaryotic cells, but having synonymous codons that are frequently used by papillomavirus genes.

FIG. 2A, comprising FIGS. 2A-1 and 2A-2, is a pair of images, each of which depicts a confocal micrograph showing detection of L1 protein expressed from synthetic (FIGS. 2A-2) and wild type (FIGS. 2A-1) BPV1 L1 genes. COS-1 cells were transfected with a synthetic L1 expression plasmid pCDNA/HBL1, and a wild type L1 expression plasmid pCDNA/BPVL1 wt. The expression of L1 was detected by immunofluorescent staining. Cells were fixed after 36 hrs and incubated with rabbit anti-BPV1 L1 antiserum, followed by FITC-conjugated goat anti-rabbit IgG antibody.

FIG. 2B is an image which depicts detection by Western blot of L1 protein from Cos-1 cells transfected with pCDNA/HBL1 and pCDNA/BPVL1 wt. Lane A is MOCK; Lane B is Wt BPV1 L11; Lane C is HB BPV1 L1; and Lane D is BPV1 Virions.

FIG. 3A, comprising FIGS. 3A-1 and 3A-2, is a pair of images, each of which depicts a confocal micrograph showing detection of L2 protein expressed from synthetic (FIG. 3A-2) and wild type (FIG. 3A-1) BPV1 L2 genes. COS-1 cells were transfected with a synthetic L2 expression plasmid pCDNA/HBL2, and a wild type L2 expression plasmid pCDNA/BPVL2 wt. The expression of L2 was detected by immunofluorescent staining. Cells were fixed after 36 hrs and incubated with rabbit anti-BPV1 L2 antiserum, followed by FITC-conjugated goat anti-rabbit IgG antibody.

FIG. 3B is an image which depicts detection by Western blot of L2 protein from COS-1 cells transfected with pCDNA/HBL2 and pCDNA/BPVL2 wt. Lane A is HB BPV1 L2; Lane B is Wt BPV1 L2; Lane C is BPV1 Virions; and Lane D is BPV1 Virions.

FIG. 4, comprising In FIG. 4A, wt L1 (Lane A) or HB L1 (Lane B) plasmid DNA was added to the T7 DNA polymerase-coupled in vitro translation system. L1 protein was detected by Western blot analysis. Lane C is a negative control. The triangle atop the remaining lanes indicates L1 wt+tRNA. In FIG. 4B, the translation efficiency of wt L1 or HB L1 sequences in the presence or absence of tRNA was compared. Translation was carried out in rabbit reticulocyte lysate (rabbit) or wheat germ extract (wheat), and samples were collected every two minutes starting from minute 8. The numbers atop the figure indicate minutes. Left side of FIG. 4B indicates if $10^{-5}$ M bovine liver or yeast tRNA was supplied. In the Figure, "LS" means L1 sequences; "RS" means tRNA source; "TS" means Translation System; "N" means Nil; "L" means Liver; "Y" means Yeast; "R" means Rabbit; and "W" means Wheat.

FIG. 5A is a schematic representation of plasmids used to determine L2 expression from BPV cryptic promoter(s). The wild type L1 sequence and most of the wild type L2 sequence were deleted from the BPV1 genome by BamHI and HindIII digestion and the remaining BPV1 sequence (in yellow) was cloned into pUC18. Wild type or synthetic humanized L2 sequences (in red) were inserted into the BamHI site of the BPV1 genome. The position of the inserted SV40 ori sequence (in white) is indicated. The plasmid in which modified L2 was used but without SV40 ori sequence was also used as a control. The plasmids were transfected into COS-1 cells and the expression of L2 protein was determined using BPV1 L2-specific polyclonal antiserum followed by FITC-linked anti rabbit IgG.

FIG. 5B, comprising FIGS. 5B-1 through 5B-4, is a series of images, each of which depicts a confocal micrograph showing expression of L2 protein from native papillomavirus promoter. The plasmids shown in FIG. 5A were used to transfect COS-1 cells (pCICR3 in FIG. 5B-2; pCICR2 in FIG. 5B-3; and pCICR1 in FIG. 5B-4) and the expression of L2 protein was determined using BPV1 L2-specific polyclonal antiserum followed by FITC-linked anti-rabbit IgG. A mock transfection (FIG. 5B-1) in which the cells did not receive plasmid was used as control.

FIG. 6A, comprising FIGS. 6A-1, 6A-2, and 6A-3, is a series of images, each of which depicts a confocal micrograph showing expression of GFP in COS-1 cells transfected with wild-type gfp (wt) (FIG. 6A-2) or a synthetic gfp gene (FIG. 6A-3) carrying codons used at relatively high frequency by papillomavirus genes (p). FIG. 6A-1 shows results from a mock transfection.

FIGS. 7A through 7L, is a series of images, each of which depicts the expression pattern of GFP in vivo from wild-type gfp gene, or a synthetic gfp gene carrying codons used at relatively high frequency by papillomavirus genes. Using a gene gun, mice were shot with PGFP (FIGS. 7A through 7F) and GFP (FIGS. 7G through 7L) expression plasmids encoding GFP protein. A transverse section of the mouse skin section shows where the gfp gene is expressed. Bright-field photographs (FIGS. 7A, 7B, 7G, and 7H) of the same section where dermis (D) epidermis (E) are highlighted are shown to identify the location of fluorescence in the epidermis. Arrows indicate fluorescent signals.

DETAILED DESCRIPTION

Figures 1, 2, 2A, 2B:
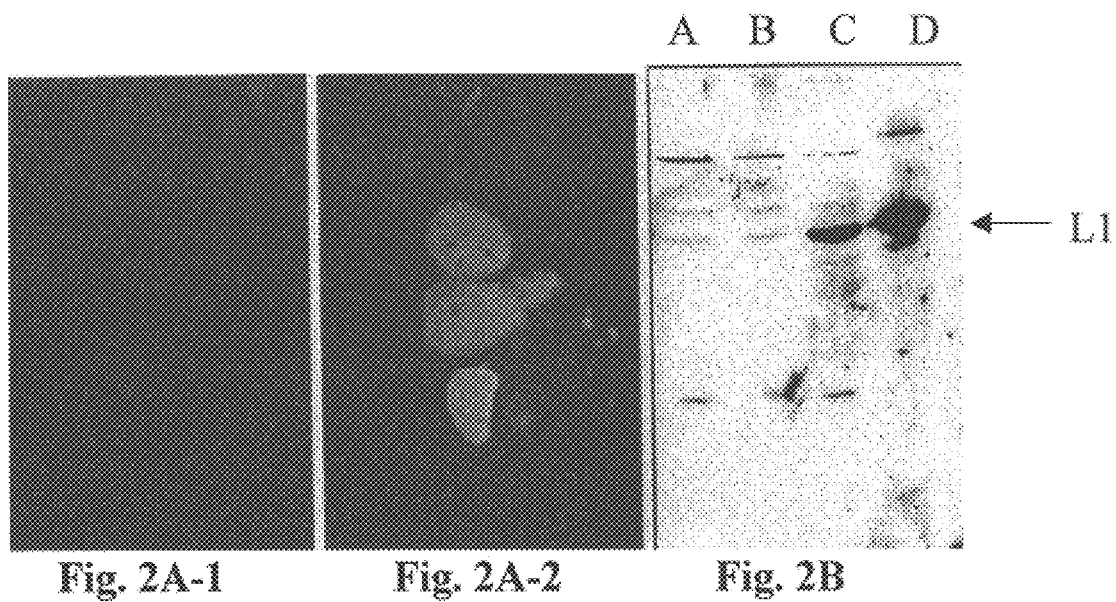

While investigating the mechanism by which protein expression is controlled during the life cycle of a bovine papillomavirus (PV), the inventors, surprisingly, discovered that PV L1 protein can be produced at substantially enhanced levels in an undifferentiated host cell by replacing existing codons of a native L1 gene with synonymous codons used at relatively high frequency by genes of the undifferentiated host cell compared to the existing codons. It has also been found unexpectedly that there are substantial differences in the relative abundance of particular isoaccepting transfer RNAs (tRNAs) in different cells or tissues and this plays a pivotal role in protein expression from a gene with a given codon usage or composition. This discovery has been reduced to practice in synthetic polynucleotides and generic methods, which utilize codon alteration as a means for targeting expression of a protein to particular cells or tissues or alternatively, to cells in a specific state of differentiation.

1. Definitions

The articles "a" and "an" are used herein to refer to one or to more than one (i.e. to at least one) of the grammatical object of the article. By way of example, "an element" means one element or more than one element.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "expressible" is meant expression of a protein to a level sufficient to effect a particular function associated with the protein. By contrast, the terms "not expressible" and "not substantially expressible" as used interchangeably herein refers to (a) no expression of a protein, (b) expression of a protein to a level that is not sufficient to effect a particular function associated with the protein, (c) expression of a protein, which cannot be detected by a monoclonal antibody specific for the protein, or (d) expression of a protein, which is less that 1% of the level expressed in a wild-type cell that normally expresses the protein.

By "expressing said synthetic construct" is meant transcribing the synthetic construct such that mRNA is produced.

By "expression vector" is meant any autonomous genetic element capable of directing the synthesis of a protein encoded by the vector. Such expression vectors are known by practitioners in the art.

As used herein, the term "function" refers to a biological, enzymatic, or therapeutic function.

By "highly expressed genes" is meant genes that express high levels of mRNA, and preferably high level of protein, relative to other genes.

By "isoaccepting transfer RNA" or "iso-tRNA" is meant one or more transfer RNA molecules that differ in their anticodon nucleotide sequence but are specific for the same amino acid.

By "natural gene" is meant a gene that naturally encodes the protein. However, it is possible that the parent polynucleotide encodes a protein that is not naturally-occurring but has been engineered using recombinant techniques.

The term "non-cycling cell" as used herein refers to a cell that has withdrawn from the cell cycle and has entered the G0 state. In this state, it is known that transcription of endogenous genes and protein translation are at substantially reduced levels compared to phases of the cell cycle, namely G1, S, G2 and M. By contrast, the term "cycling cell" as used herein refers to a cell, which is in one of the above phases of the cell cycle.

By "obtained from" is meant that a sample such as, for example, a polynucleotide extract or polypeptide extract is isolated from, or derived from, a particular source of the host. For example, the extract can be obtained from a tissue or a biological fluid isolated directly from the host.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

By "pharmaceutically-acceptable carrier" is meant a solid or liquid filler, diluent or encapsulating substance that can be safely used in topical or systemic administration to a mammal.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polynucleotide" or "nucleic acid" as used herein designates mRNA, RNA, cRNA, cDNA or DNA. The term typically refers to oligonucleotides greater than 30 nucleotide residues in length.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Preferably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labeled directly or indirectly.

The terms "precursor cell or tissue" and "progenitor cell or tissue" as used herein refer to a cell or tissue that can gives rise to a particular cell or tissue in which protein expression is to be targeted or in which translational efficiency of a codon is to be determined.

By "recombinant polypeptide" is meant a polypeptide made using recombinant techniques, i.e., through the expression of a recombinant or synthetic polynucleotide.

"Stringency" as used herein, refers to the temperature and ionic strength conditions, and presence or absence of certain organic solvents, during hybridization. The higher the stringency, the higher will be the degree of complementarity between immobilized polynucleotides and the labeled polynucleotide.

"Stringent conditions" refers to temperature and ionic conditions under which only polynucleotides having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "synthetic polynucleotide" as used herein refers to a polynucleotide formed in vitro by the manipulation of a polynucleotide into a form not normally found in nature. For example, the synthetic polynucleotide can be in the form of an expression vector. Generally, such expression vectors include transcriptional and translational regulatory polynucleotide operably linked to the polynucleotide.

The term "synonymous codon" as used herein refers to a codon having a different nucleotide sequence than another codon but encoding the same amino acid as that other codon.

By "translational efficiency" is meant the efficiency of a cell's protein synthesis machinery to incorporate the amino acid encoded by a codon into a nascent polypeptide chain. This efficiency can be evidenced, for example, by the rate at which the cell is able to synthesize the polypeptide from an RNA template comprising the codon, or by the amount of the polypeptide synthesized from such a template.

By "vector" is meant a polynucleotide molecule, preferably a DNA molecule derived, for example, from a plasmid, bacteriophage, or plant virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

2. Selection of Synonymous Codons

The present invention arises from the unexpected discovery that the translational efficiencies of different codons varies between different cells or tissues, or alternatively between cells or tissues in different states of differentiation or between cells in different stages of the cell cycle. Such differences can be exploited together with codon composition of a gene to regulate and direct expression of a protein to a particular cell or cell type, including cells in a selected tissue. Alternatively, these differences can be exploited together with codon composition of a gene to regulate and direct expression of a protein to a cell or tissue in a selected state of differentiation or in a selected stage of the cell cycle. According to the present invention, this selective targeting is effected by replacing at least one existing codon (sometimes referred to as a "first codon") of a parent polynucleotide encoding the protein with a synonymous codon (i.e. one which encodes the same amino acid residue as the first codon).

Replacement of synonymous codons for existing codons is not new per se. In this regard, we refer to International Application Publication No WO 96/09378 which utilizes such substitution to provide a method of expressing proteins of eukaryotic and viral origin at high levels in in vitro mammalian cell culture systems, the main thrust of that method being the harvesting of such proteins. In distinct contrast, the present invention utilizes substitution of one or more codons in a gene to target expression of the gene to particular cells or tissues with the ultimate aim of facilitating gene therapy as described herein.

The present method preferably includes the step of selecting the codons such that the synonymous codon has a higher translational efficiency in said target cell or tissue ("cell or tissue" is sometimes referred to herein as "cell/tissue") relative to said one or more other cells or tissues. As used herein, expression of a protein in a tissue refers alternatively to expression of the protein within a cell of the tissue or production of the protein within a cell and export of the protein from the cell to, for example, the extracellular matrix of a tissue.

Methods for determining translational efficiencies of different codons in and between different cells or tissues are described in detail in Section 3. The translational efficiencies so determined can be used to identify which isocoding triplets are differentially translated between the different cells or tissues. In a typical scenario, there will be: (A) codons with higher translational efficiencies in a target cell/tissue relative to one or more other cells/tissues; (B) codons with higher translational efficiencies in the one or more other cells/tissues relative to the target cell/tissue; and (C) codons with about the same translational efficiencies in the target cell/tissue relative to the one or more other cells/tissues. Synonymous codons are selected such that they correspond to (A) codons. Preferably, a synonymous codon is selected such that it has the largest difference in translational efficiency in the target cell or tissue relative to the existing codon that it replaces. Existing codons in a parent polynucleotide are preferably selected such that they do not have the same translational bias as the synonymous codons with respect to the target cell/tissue and the one or more other cell/tissue (i.e., existing codons should preferably not correspond to (A) codons). However, existing codons can have similar translational efficiencies in each of the target cell/tissue and the one or more other cells/tissues (i.e., existing codons can correspond to (C) codons. They can also have a translational bias opposite to that of the synonymous codons (i.e., existing codons can, and preferably do, correspond to (B) codons).

Suitably, a synonymous codon has a translational efficiency in the target cell/tissue that is at least 110%, preferably at least 200%, more preferably at least 500%, and still more preferably at least 1000%, of that in the other cell(s)/tissue(s). In the case of two or more synonymous codons having similar translational efficiencies in the target cell/tissue relative to the other cell(s)/tissue(s), it will be appreciated that any one of these codons can be used to replace the existing codon.

It is preferable but not necessary to replace all the existing codons of the parent polynucleotide with synonymous codons having higher translational efficiencies in the target cell/tissue compared to the other cells/tissues. Increased expression can be accomplished even with partial replacement. Suitably, the replacement step affects 5%, 10%, 15%, 20%, 25%, 30%, more preferably 35%, 40%, 50%, 60%, 70% or more of the existing codons of the parent polynucleotide.

The difference in level of protein expressed in the target cell/tissue from a synthetic polynucleotide relative to that expressed in the other cell(s)/tissue(s) depends on the percentage of existing codons replaced by synonymous codons, and the difference in translational efficiencies of the synonymous codons in the target cell/tissue relative to the other cell(s)/tissue(s). Put another way, the fewer such replacements, and/or the smaller the difference in translational efficiencies of the synonymous codons between the different cells/tissues, the smaller the difference in protein expression between the target cell/tissue and the other cell(s)/tissue(s) will be. Conversely, the more such replacements, and/or the greater the difference in translational efficiencies of the synonymous codons between the different cells/tissues, the greater the difference in protein expression between the target cell/tissue and the other cell(s)/tissue(s) will be. The inventors have found in this respect that a protein can be expressed from a synthetic polynucleotide in a target cell/tissue at levels greater than 10,000-fold over those expressed in another cell/tissue.

In contrast to differential protein expression between different cells/tissues, it will be appreciated that a synthetic polynucleotide may be tailored with synonymous codons such that expression of a protein in a target cell is enhanced. In this regard, the difference in level of protein expressed in the target cell/tissue from a synthetic polynucleotide relative to that expressed from a parent polynucleotide depends on the percentage of existing codons replaced by synonymous codons, and the difference in translational efficiencies between the existing codons and the synonymous codons in the target cell/tissue. Put another way, the fewer such replacements, and/or the smaller the difference in translational efficiencies between the synonymous and existing codons, the smaller the difference in protein expression between the synthetic polynucleotide and parent polynucleotide will be. Conversely, the more such replacements, and/or the greater the difference in translational efficiencies between the synonymous and existing codons, the greater the difference in protein expression between the synthetic polynucleotide and parent polynucleotide will be. The inventors have found in this respect that a protein can be expressed from a synthetic polynucleotide in a target cell/tissue at levels greater than 10,000-fold than from a parent polynucleotide.

Preferably, the at least one existing codon and the synonymous codon are selected such that said protein is expressed from said synthetic polynucleotide in said target cell or tissue at a level which is at least 110%, preferably at least 200%, more preferably at least 500%, and most preferably at least 1000%, of that expressed from said parent polynucleotide in said target cell or tissue.

In a preferred embodiment, the synonymous codon is a codon which has a higher translational efficiency in the target cell or tissue relative to a precursor cell or tissue of the target cell or tissue.

In an alternate embodiment, the synonymous codon is a codon which has a higher translational efficiency in the target cell or tissue relative to a cell or tissue derived from said target cell or tissue.

The two codons can be selected by measuring translational efficiencies of different codons in the target cell or tissue relative to the one or more other cells or tissues and identifying the at least one existing codon and the synonymous codon based on this measurement.

Synonymous codon(s) are preferably selected from the group consisting of aga (Arg), cgg (Arg), tgc (Cys), gga (Gly), ggc (Gly), ccg (Pro), cga (Pro), aca (Thr), acg (Thr), and act (Thr), wherein said target cell is an undifferentiated cell, and preferably an undifferentiated epithelial cell.

Suitably, the at least one existing codon is selected from the group consisting of agg (Arg), tgt (Cys), ggg (Gly), ggt (Gly), ccc (Pro), cct (Pro), and acc (Thr), wherein said target cell is an undifferentiated cell, and preferably an undifferentiated epithelial cell.

Suitably, synonymous codons for higher level expression of a protein in a differentiated cell, preferably a differentiated keratinocyte, are selected from the group consisting of gca (Ala), cuu (Leu) and cua (Leu).

Synonymous codons for higher level expression of a protein in an undifferentiated cell, preferably an undifferentiated keratinocyte, are suitably selected from the group consisting of cga (Arg), cci (Pro) and aag (Asn).

3. Methods of Determining Codon Translational Efficiency 3.1. Expressing a Synthetic Construct Comprising a Tandem Repeat of Identical Codons Fused in Frame to a Reporter Polynucleotide A major aspect of the present invention is based, at least in part, on the discovery that different but synonymous stretches of identical codons fused respectively in frame with a reporter polynucleotide can give rise to different levels of reporter protein expressed within a given cell type. Not wishing to be bound by any particular theory, it is believed that a tandem series of identical codons causes a ribosome to pause during translation if the iso-tRNA corresponding to the identical codons is limiting. In this regard, it is known that ribosomal pausing leads to a failure to complete a nascent polypeptide chain and an uncoupling of transcription and translation. Accordingly, the levels of reporter protein expressed in the different cells or tissues are sensitive to the intracellular abundance of the iso-tRNA species corresponding to the identical codons and therefore provide a direct correlation of a cell's or tissue's preference for translating a given codon. This means, for example, that if the levels of the reporter protein obtained in a cell or tissue type to which a synthetic construct having a tandem series of identical first codons is provided are lower than the levels expressed in the same cell or tissue type to which a different synthetic construct having a tandem series of identical second codons is provided (i.e. wherein the first codons are different from, but synonymous with, the second codons), then it can be deduced that the cell or tissue has a higher preference for the second codon relative to the first codon with respect to translation. Put another way, the second codon has a higher translational efficiency compared to the first codon in the cell or tissue type.

With regard to differential protein expression between different cell or tissue types, it will be appreciated that if the levels of the reporter protein obtained in a target cell or tissue type to which a synthetic construct having a tandem series of identical codons is provided are lower than the levels expressed in the another cell or tissue type to which the same synthetic construct is provided, then it can be deduced that the target cell or tissue has a higher preference for the codon relative to the other cell or tissue with respect to translation. Put another way, the codon has a higher translational efficiency in the target cell or tissue compared to the other cell or tissue type.

Suitably, the tandem repeat comprises at least three identical codons. Preferably, the tandem repeat comprises four identical codons, more preferably five or seven identical codons and most preferably six identical codons.

The tandem repeat can be fused at a location adjacent to, or within, the reporter polynucleotide. The location is preferably selected such that the tandem repeat interferes with translation of at least a detectable portion of the reporter protein such that expression of the protein can be detected or assessed. Preferably, the tandem repeat is located immediately upstream (translationally) from the reporter polynucleotide.

It is of course possible that a tandem repeat of identical amino acid residues (e.g., an oligo-proline repeat) can render the reporter protein unstable. Typically, protein instability is detected when expression of the reporter gene is not detectable with any choice of isoaccepting codon specific for the amino acid corresponding to the tandem repeat. The inventors have found in this regard that protein instability can be alleviated by use of at least one spacer codon within the tandem repeat of identical codons, wherein the spacer codon encodes a neutral amino acid.

The at least one spacer codon can be placed adjacent to, or interposed between, some or all of the identical codons corresponding to the tandem repeat. For example, a suitable interposition for a penta-repeat of identical codons can be selected from the group consisting of: (a) I-S-I-S-I-S-I-S-I-S; (b) S-I-S-I-S-I-S-I-S-I; (c) I-S-I-S-I-I-S-I; (d) I-S-I-I-S-I-S-I; (e) I-S-I-S-I-I-I; (f) I-I-S-I-S-I-I; (g) I-I-I-S-I-S-I; (h) I-S-I-I-S-I-I; (i) I-I-S-I-I-S-I; (j) I-S-I-I-I-S-I; (k) I-S-I-I-I-I; (l) I-I-S-I-I-I; (m) I-I-I-S-I-I; and (n) I-I-I-I-S-I, wherein I corresponds to an identical codon of a tandem repeat and S corresponds to a spacer codon.

Preferably, a spacer codon is efficiently translated in the cell or tissue type relative to other synonymous codons. This is important so that translation of the spacer codon is not rate limiting. The neutral amino acid includes, but is not restricted to, alanine and glycine.

The reporter polynucleotide can encode any suitable protein for which expression can be detected directly or indirectly such as by suitable assay. Suitable reporter polynucleotides include, but are not restricted to, polynucleotides encoding β-galactosidase, firefly luciferase, alkaline phosphatase, chloramphenicol acetyltransferase (CAT), β-glucuronidase (GUS), herbicide resistance genes such as the bialophos resistance (BAR) gene that confers resistance to the herbicide BASTA, and green fluorescent protein (GFP). Assays for the activities associated with such proteins are known by those of skill in the art. Preferably, the reporter polynucleotide encodes GFP.

Persons of skill in the art will appreciate that reporter polynucleotides need not correspond to a full-length gene encoding a particular reporter protein. In this regard, the invention also contemplates reporter polynucleotide sub-sequences encoding desired portions of a parent reporter protein, wherein an activity or function of the parent protein is retained in said portions. A polynucleotide sub-sequence encodes a domain of the reporter protein having an activity associated therewith and preferably encodes at least 10, 20, 50, 100, 150, or 500 contiguous amino acid residues of the reporter protein.

The instant method is applicable to any suitable cell or tissue type and, hence, is not restricted to application to mammalian cells/tissues. Accordingly, the cell or tissue type can be of any animal or plant origin. The cell or tissue type can be of any suitable lineage. For example, a suitable cell can include a eukaryotic cell, and preferably a cell or cell line capable of being grown in vitro. Suitable cell lines can include, for example, CV-1 cells, COS cells, yeast or spodoptera cells. The invention also contemplates cells that can be prokaryotic in origin.

Suitable methods for isolating particular cells or tissues are known to those of skill in the art. For example, one can take advantage of one or more particular characteristics of a cell or tissue to specifically isolate the cell or tissue from a heterogeneous population. Such characteristics include, but are not limited to, anatomical location of a tissue, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaffinity separation (e.g., magnetic bead separation such as Dynabead™ separation), density separation (e.g., metrizamide, Percoll™, or Ficoll™ gradient centrifugation), and cell-type specific density separation.

In an alternate embodiment, progenitor cells or tissues can be used for initially introducing the synthetic construct. Any suitable progenitor cell or tissue can be used which gives rise to a particular cell or tissue of interest for which codon preference is to be ascertained. For example, a suitable progenitor cell can comprise an undifferentiated cell. In the case of a plant, a suitable progenitor cell and tissue can include a meristematic cell and a callus tissue, respectively.

In another embodiment, the synthetic construct can be introduced first into an organism or part thereof before subsequent expression of the construct in a particular cell or tissue type. Any suitable organism is contemplated by the invention including unicellular and as multi-cellular organisms. Exemplary multi-cellular organisms include mammals (e.g. humans) and plants.

The invention further provides a synthetic construct comprising a reporter polynucleotide fused in frame with a tandem repeat of (e.g., 2, 3, 4, 5, 6, or 7 or more) identical codons, wherein said reporter polynucleotide encodes a reporter protein, and wherein said synthetic construct is operably linked to one or more regulatory polynucleotides.

The construction of the synthetic construct can be effected by any suitable technique. For example, in vitro mutagenesis methods can be employed, which are known to those of skill in the art. Suitable mutagenesis methods are described for example in the relevant sections of Ausubel, et al. (supra) and of Sambrook, et al., (supra) which are incorporated herein by reference. Alternatively, suitable methods for altering DNA are set forth, for example, in U.S. Pat. Nos. 4,184,917, 4,321,365 and 4,351,901, which are incorporated herein by reference. Instead of in vitro mutagenesis, the synthetic polynucleotide can be synthesized de novo using readily available machinery. Sequential synthesis of DNA is described, for example, in U.S. Pat. No. 4,293,652, which is incorporated herein by reference. However, it should be noted that the present invention is not dependent on, and not directed to, any one particular technique for constructing the synthetic construct.

Regulatory polynucleotides which can be utilized to regulate expression of the synthetic polynucleotide include, but are not limited to, a promoter, an enhancer, and a transcription terminator. Such regulatory polynucleotides are known to those of skill in the art. The construct preferably comprises at least one promoter.

Regulatory polynucleotides which can be utilized to regulate expression of the synthetic construct include, but are not limited to, a promoter, an enhancer, and a transcriptional terminator. Such regulatory polynucleotides are known to those of skill in the art. Suitable promoters that can be utilized to induce expression of the polynucleotides of the invention include constitutive promoters and inducible promoters.

3.2. Determination of Abundance of Different tRNA Species in and/or between Different Cells The present invention contemplates any suitable method for determining the abundance of different iso-tRNA species in and/or between different cell or tissue types. For example, such method can include isolating a particular cell or tissue from a mammal, preparing an RNA extract from the cell or tissue which extract includes tRNA, and probing the extract with polynucleotides having different nucleic acid sequences, each being specific for a particular iso-tRNA to thereby determine the relative abundance of different iso-tRNAs in said cell or tissue. Preferably, this method is applied to two or more different cell or tissue types to determine the relative abundance of different iso-tRNAs between those cell or tissue types.

Suitable methods for isolating particular cells or tissues are known to those of skill in the art and are described, for example, in Section 3.1 above.

Any suitable method for isolating total RNA from a cell or tissue can be used. Typical procedures contemplated by the invention are described in CURRENT PROTOCOLS IN MOLECULAR BIOLOGY (Ausubel, et al., Eds.) (John Wiley & Sons, Inc. 1997), hereby incorporated by reference, at page 4.2.1 through page 4.2.7. Preferably, techniques which favor isolation of tRNA are employed as, for example, described in Brunngraber, E. F. (1962, *Biochem. Biophys. Res. Commun.* 8: 1–3), which is hereby incorporated by reference.

The probing of an RNA extract is suitably effected with different oligonucleotide sequences each being specific for a particular iso-tRNA. Of course it will be appreciated that for a given mammal, oligonucleotide sequences would need to be selected which hybridize specifically with particular iso-tRNA sequences expressed by the mammal. Such selection is within the realm of one of ordinary skill in the art based on any known iso-tRNA sequence. Reference can be made in this regard to a compilation of tRNA sequences and sequences of tRNA genes described in Sprinzl et al (1996, *Nucleic Acids Res.* 24(1): 68–72; 1998, 26(1): 148–53; the entire disclosures of which are incorporated herein by reference.

In the case of a mouse, for example, exemplary oligonucleotide sequences which can be used include those described by Gauss and Sprinzl (1983, *Nucleic Acids Res.* 11: 1 incorporated herein by reference) . In this respect, the oligonucleotide sequences can, for example, be any of:

5'-TA$\underset{GCA}{A}$GGACTGTAAGACTT-3' (SEQ ID NO:13) for Ala

5'-CG$\underset{CGA}{A}$GCCAGCCAGGAGTC-3' (SEQ ID NO:14) for Arg

5'-CT$\underset{AAC}{A}$GATTGGCAGGAATT-3' (SEQ ID NO:15) for Asn

5'-TAAGATATATAGATTAT-3' (SEQ ID NO:16) for Asp-$_{GAC}$

5'-AAGTCTTAGTAGAGATT-3' (SEQ ID NO:17) for Cys$^{TGC}$

5'-TATTTCTACACAGCATT-3' (SEQ ID NO:18) for Glu$^{GAA}$

5'-CTAGGACAATAGGAATT-3' (SEQ ID NO:19) for Gln$^{CAA}$

5'-TACTCTCTTCTGGGTTT-3' (SEQ ID NO:20) for Gly$^{GGA}$

5'-TGCCGTGACTCGGATTC-3' (SEQ ID NO:21) for His$^{CAC}$

5'-TAGAAATAAGAGGGCTT-3' (SEQ ID NO:22) for Ile$^{ATC}$

5'-TACTTTTATTTGGATTT-3' (SEQ ID NO:23) for Leu$^{CTA}$

5'-TATTAGGGAGAGGATTT-3' (SEQ ID NO:24) for Leu$^{CTT}$

5'-TCACTATGGAGATTTTA-3' (SEQ ID NO:25) for Lys$^{AAA}$

5'-CGCCCAACGTGGGGCTC-3' (SEQ ID NO:26) for Lys$^{AAG}$

5'-TAGTACGGGAAGGATTT-3' (SEQ ID NO:27) for Met$^{elong}$

5'-TGTTTATGGGATACAAT-3' (SEQ ID NO:28) for Phe$^{TTC}$

5'-TCAAGAAGAAGGAGCTA-3' (SEQ ID NO:29) for Pro$^{CCA}$

5'-GGGCTCGTCCGGGATTT-3' (SEQ ID NO:30) for Pro$^{CCI}$

5'-ATAAGAAAGGAAGATCG-3' (SEQ ID NO:31) for Ser$^{AGC}$

5'-TGTCTTGAGAAGAGAAG-3' (SEQ ID NO:32) for Thr$^{ACA}$

5'-TGGTAAAAAGAGGATTT-3' (SEQ ID NO:33) for Tyr$^{TAC}$

5'-TCAGAGTGTTCATTGGT-3' (SEQ ID NO:34) for Val$^{GTA}$

Typically, the abundance of iso-tRNA species can be determined by blotting techniques that include a step whereby a sample RNA or tRNA extract is immobilized on a matrix (preferably a synthetic membrane such as nitrocellulose), a hybridization step, and a detection step. Northern blotting can be used to identify an RNA sequence that is complementary to a polynucleotide probe. Alternatively, dot blotting and slot blotting can be used to identify complementary DNA/RNA or RNA/RNA nucleic acid sequences. Such techniques are known by those skilled in the art, and have been described, for example, in Ausubel, et al (supra) at pages 2.9.1 through 2.9.20.

According to such methods, a sample of tRNA immobilized on a matrix is hybridized under stringent conditions to a complementary polynucleotide (such as one having a sequence mentioned above) which is labeled, for example, radioactively, enzymatically or fluorochromatically.

While stringent washes are typically carried out at temperatures from about 42° C. to 68° C., one skilled in the art will appreciate that other temperatures can be suitable for stringent conditions. Maximum hybridization typically occurs at about 20° to 25° below the $T_m$ for formation of a DNA-DNA hybrid. It is known in the art that the Tm is the melting temperature, or temperature at which two complementary polynucleotides dissociate. Methods for estimating $T_m$ are known in the art (see, e.g., CURRENT PROTOCOLS IN MOLECULAR BIOLOGY supra at page 2.10.8). Maximum hybridization typically occurs at about 10° to 15° below the $T_m$ for a DNA-RNA hybrid.

Other stringent conditions are known in the art. A skilled artisan will recognize that various factors can be manipulated to optimize the specificity of the hybridization. Optimization of the stringency of the final washes can serve to ensure a high degree of hybridization.

Methods for detecting labeled polynucleotides hybridized to an immobilized polynucleotide are known to practitioners in the art. Such methods include autoradiography, chemiluminescent, fluorescent and colorimetric detection.

Advantageously, the relative abundance of an iso-tRNA between two or more cells or tissues can be determined by comparing the respective levels of binding of a labeled polynucleotide specific for the iso-tRNA to equivalent amounts of immobilized RNA obtained from the two or more cells or tissues. Similar comparisons are suitably carried out to determine the respective relative abundance of other iso-tRNAs between the two or more cells or tissues. One of ordinary skill in the art will thereby be able to determine a relative tRNA abundance table (see for example TABLE 2) for different cells or tissues. From such comparisons, one or more synonymous codons can be selected such that the or each synonymous codon corresponds to an iso-tRNA which is in higher abundance in the target cell or tissue relative to other cells or tissues of the mammal.

In the present embodiment, a synonymous codon is preferably selected such that its corresponding iso-tRNA is present in the target cell or tissue at a level which is at least 110%, preferably at least 200%, more preferably at least 500%, and most preferably at least 1000%, of that present in one or more other cells or tissues of the mammal.

3.3. Analysis of Codon Usage

Alternatively, synonymous codons can be selected by analyzing the frequency at which codons are used by genes expressed in (i) particular cells or tissues, (ii) substantially all cells or tissues of the mammal, or (iii) an organism which can infect particular cells or tissues of the mammal.

Codon frequency tables as well as suitable methods for determining frequency of codon usage in an organism are described, for example, in an article by Sharp et al (1988, *Nucleic Acids Res.* 16 8207–8211), which is incorporated herein by reference. Reference also can be made to an article by Nakamura et al (2000, *Nucleic Acids Res* 28(1): 292, incorporated herein by reference), which presents the frequency of each of the 257 468 complete protein-coding sequences (CDSs) compiled from the taxonomic divisions of the GenBank DNA sequence database. The sum of the codons used by 8792 organisms is also calculated. The data files relating to this article can be obtained from the anonymous ftp sites of DDBJ, Kazusa and EBI. A list of the codon usage of genes and the sum of the codons used by each organism can, for example, be obtained through web sites.

The relative level of gene expression (e.g., detectable protein expression vs. no substantial or detectable protein expression) can provide an indirect measure of the relative translational efficiencies of codons, the relative abundance of specific iso-tRNAs expressed, or both, in different cells or tissues. For example, a virus can be capable of propagating within a first cell or tissue (which can include a cell or tissue at a specific stage of differentiation) but can be substantially incapable of propagating in a second cell or tissue (which can include a cell or tissue at another stage of differentiation). Comparison of the pattern of codon usage by genes of the virus with the pattern of codon usage by genes expressed in the second cell or tissue can thus provide indirectly a set of codons that have high translational efficiencies and a set of codons that have low translational efficiencies in the first cell or tissue relative to the second cell or tissue. Simultaneously, the above comparison can also provide indirectly a set of codons that that have higher translational efficiencies and a set of codons that have low translational efficiencies in the second cell or tissue relative to the first cell or tissue.

From the foregoing, a synonymous codon according to the invention can correspond to a codon selected from the group consisting of (1) a codon used at relatively high frequency by genes, preferably highly expressed genes, of a target cell or tissue, (2) a codon used at relatively high frequency by genes, preferably highly expressed genes, of the mammal, (3) a codon used at relatively low frequency by genes of one or more other cells or tissues, and (4) a codon used at relatively low frequency by genes of another organism.

By contrast, an existing codon according to the invention can correspond to a codon selected from the group consisting of (a) a codon used at relatively high frequency by genes, preferably highly expressed genes, of one or more other cells or tissues, (b) a codon used at relatively low frequency by genes of a target cell or tissue, (c) a codon used at relatively low frequency by genes of the mammal, and (d) a codon used at relatively high frequency by genes of another organism.

Preferably, the genes from which codon frequency data are obtained do not relate to mitochondrial genes.

Suitably, a highly expressed gene according to the invention encodes a protein that is expressed at high levels, and preferably specifically (i.e., substantially only, e.g. at a level at least about 100-fold greater than in other cells or tissues), in the target cell/tissue. Examples of such genes include the lactalbumen gene expressed in breast epithelium, oncogenes expressed in cancer cells (e.g., Bcl-2, p53, erbB, C-myb, C-mos, C-rel etc), insulin expressed in beta cells, transglutaminase and loricrin expressed in differentiated epithelium, and E2F1 expressed in cycling undifferentiated cells Codons used at a relatively high frequency by genes, preferably highly expressed genes, of the mammal can be selected from the group consisting of: cuc (Leu), cuu, (Leu), cug (Leu), uua (Leu), uug (Leu); cgg (Arg), cgc (Arg), aga (Arg), agg (Arg); agu (Ser), agc (Ser), ucu (Ser), ucc (Ser), and uca (Ser). Alternatively, such codons can include auu (Ile), auc (Ile); guu (Val), guc (Val), gug (Val); acu (Thr), acc (Thr), aca (Thr); gcu (Ala), gcc (Ala), gca (Ala); cag (Glu); ggc (Gly), gga (Gly), ggg (Gly).

Codons used at a relatively low frequency by genes of mammals are described, for example, in Sharp et al (1988, supra). Such codons include, but are not restricted to, cua (Leu); cga (Arg), cgu (Arg); ucg (Ser). Alternatively, such codons can include aua (Ile); gua (Val); acg (Thr); gcg (Ala); caa (Glu); ggu (Gly).

4. Construction of Synthetic Polynucleotides

The step of replacing synonymous codons for existing codons can be effected by any suitable technique. For example, in vitro mutagenesis methods can be employed which are known to those of skill in the art and include those described in Section 3.1 above.

The parent polynucleotide is preferably a natural gene. However, it is possible that the parent polynucleotide encodes a protein that is not naturally-occurring but has been engineered using recombinant techniques.

The parent polynucleotide need not be obtained from the mammal but can be obtained from any suitable source, such as from a eukaryotic or prokaryotic organism. For example, the parent polynucleotide can be obtained from another mammal or other animal. Alternatively, the parent polynucleotide can be obtained from a pathogenic organism. In such a case, a natural host of the pathogenic organism is preferably a mammal. For example, the pathogenic organism can be a yeast, bacterium or virus.

For example, suitable proteins which can be used for selective expression in accordance with the invention include, but are not limited to the cystic fibrosis transmembrane conductance regulator (CFTR) protein, and adenosine deaminase (ADA). In the case of CFTR, a parent polynucleotide encoding the CFTR protein which can be utilized to produce the synthetic polynucleotide is described, for example, in Riordan et al (1989, Science 245 1066–1073), and in the GenBank database under locus designation HUM-CFTRM (Accession number M28668), which are incorporated herein by reference.

Regulatory polynucleotides which can be utilized to regulate expression from the synthetic polynucleotide include, but are not limited to, a promoter, an enhancer, and a transcriptional terminator. Such regulatory polynucleotides are known to those of skill in the art.

Synthetic polynucleotides according to the invention can be operably linked to one or more regulatory polynucleotides in the form of an expression vector.

The invention also contemplates synthetic polynucleotides encoding one or more desired portions of the protein to be expressed. A polynucleotide encodes a domain of the protein having a function associated therewith, or which is otherwise detectable, and preferably encodes at least 10, 20, 50, 100, 150, or 500 contiguous amino acid residues of the protein.

The step of introducing the synthetic polynucleotide into a target cell differs depending on the intended use and species, and can involve one or more of non-viral and viral vectors, cationic liposomes, retroviruses, and adenoviruses such as, for example, described in Mulligan, R. C., (1993 Science 260 926–932) which is hereby incorporated by reference. Such methods can include, for example:

A. Local application of the synthetic polynucleotide by injection (Wolff et al., 1990, Science 247 1465–1468, which is hereby incorporated by reference), surgical implantation, instillation or any other means. This method can also be used in combination with local application by injection, surgical implantation, instillation or any other means, of cells responsive to the protein encoded by the synthetic polynucleotide so as to increase the effectiveness of that treatment. This method can also be used in combination with local application by injection, surgical implantation, instillation or any other means, of another factor or factors required for the activity of said protein.

B. General systemic delivery by injection of DNA, (Calabretta et al., 1993, Cancer Treat. Rev. 19 169–179, which is incorporated herein by reference), or RNA, alone or in combination with liposomes (Zhu et al., 1993, Science 261 209–212, which is incorporated herein by reference), viral capsids or nanoparticles (Bertling et al., 1991, Biotech. Appl. Biochem. 13 390–405, which is incorporated herein by reference) or any other mediator of delivery. Improved targeting might be achieved by linking the synthetic polynucleotide to a targeting molecule (the so-called "magic bullet" approach employing, for example, an antibody), or by local application by injection, surgical implantation or any other means, of another factor or factors required for the activity of the protein encoding said synthetic polynucleotide , or of cells responsive to said protein.

C. Injection or implantation or delivery by any means, of cells that have been modified ex vivo by transfection (for example, in the presence of calcium phosphate: Chen et al., 1987, *Mole. Cell Biochem.* 7 2745–2752, or of cationic lipids and polyamines: Rose et al., 1991, BioTech. 10 520–525, which articles are incorporated herein by reference), infection, injection, electroporation (Shigekawa et al., 1988, *BioTech.* 6 742–751, which is incorporated herein by reference) or any other way so as to increase the expression of said synthetic polynucleotide in those cells. The modification can be mediated by plasmid, bacteriophage, cosmid, viral (such as adenoviral or retroviral; Mulligan, 1993, *Science* 260 926–932; Miller, 1992, *Nature* 357 455–460; Salmons et al., 1993, *Hum. Gen. Ther.* 4 129–141, which articles are incorporated herein by reference) or other vectors, or other agents of modification such as liposomes (Zhu et al., 1993, *Science* 261 209–212, which is incorporated herein by reference), viral capsids or nanoparticles (Bertling et al., 1991, *Biotech. Appl. Biochem.* 13 390–405, which is incorporated herein by reference), or any other mediator of modification. The use of cells as a delivery vehicle for genes or gene products has been described by Barr et al., 1991, *Science* 254 1507–1512 and by Dhawan et al., 1991, *Science* 254 1509–1512, which articles are incorporated herein by reference. Treated cells can be delivered in combination with any nutrient, growth factor, matrix or other agent that will promote their survival in the treated subject.

5. Pharmaceutical Compositions

In yet another aspect, the invention provides a pharmaceutical composition comprising the synthetic nucleic sequences of the invention and a pharmaceutically acceptable carrier.

Depending upon the particular route of administration, a variety of pharmaceutically acceptable carriers, known in the art can be used. These carriers can be selected from a group including sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Any suitable technique can be employed for determining expression of the protein from said synthetic polynucleotide in a particular cell or tissue. For example, expression can be measured using an antibody specific for the protein of interest or portion thereof. Such antibodies and measurement techniques are known to those skilled in the art.

6. Applications 6.1. Targeting Expression of a Protein to a Differentiated Cell

In one embodiment of the present invention, the target cell is suitably a differentiated cell. Advantageously, the protein which is desired to be selectively expressed in the differentiated cell is not expressible in a precursor cell thereof (such as an undifferentiated or less differentiated cell of the mammal) from a parent polynucleotide at a level sufficient to effect a particular function associated with said protein. In this embodiment, the step of replacing at least one existing codon with a synonymous codon is characterized in that, when compared to the at least one existing codon, the synonymous codon has a higher translational efficiency in the differentiated cell compared to the precursor cell. Accordingly, a synthetic polynucleotide is produced having altered translational kinetics compared to the parent polynucleotide wherein the protein is expressible in the differentiated cell at a level sufficient to effect a particular function associated with said protein, but wherein the protein is not expressible in the precursor cell at a level sufficient to effect said function.

The above embodiment can be utilized advantageously for somatic gene therapy where overexpression of a protein in undifferentiated cells such as stems cells has undesirable consequences including death or differentiation of the stem cells. In such a case, a suitable protein can include cystic fibrosis transmembrane conductance regulator (CFTR) protein, and adenosine deaminase (ADA).

The differentiated cell can comprise a cell of any lineage including a cell of epithelial, hemopoetic or neural origin. For example, the differentiated cell can be a mature differentiated keratinocyte.

6.2. Targeting Expression of a Protein to Progeny of a Stem Cell but not to the Stem Cell Itself The synthetic polynucleotide produced above can be transfected directly into the differentiated cell for the desired function or alternatively, transfected into the precursor cell. For example, in the case of ADA deficiency, expression of ADA in stem cells can result in loss of stem phenotype that is undesirable. However, an advantageous therapy can reside in transducing autologous marrow stem cells with a synthetic polynucleotide operably linked to one or more regulatory polynucleotides, wherein existing codons of the wild type ADA gene have been replaced with synonymous codons which have higher translational efficiencies in differentiated lymphocytes compared to the marrow stem cells. The transduced stem cells can then be re-infused into the patient. This approach will result in transduced marrow stem cells which are not capable of expressing ADA themselves, but which are able to give rise to a renewable population of differentiated lymphocytes which are capable of expressing ADA at levels sufficient to permit a therapeutic effect. In this regard, a suitable cell source for this purpose can comprise stem cells isolated as CD34 positive cells from a patient's peripheral blood or marrow. For gene delivery, a suitable vector can include a retrovirus or an adeno-associated virus.

Alternatively, in the case of inducing cell mediated immunity, dendritic cells are important antigen presenting cells (APC) but have a very limited life span for antigen presentation once activated of between 14 to 21 days. Consequently, dendritic cells provide relatively short-term immune stimulation that can not be optimal. However, in accordance with the present invention, a long-term immune stimulation can be provided by transducing autologous bone marrow-derived CD34 positive dendritic cell precursors with a synthetic polynucleotide encoding an antigen, such as the melanoma antigen MART-1. In this example, the synthetic sequence is constructed such that existing codons of a wild-type polynucleotide encoding MART-1 are replaced with synonymous codons which have higher translational efficiencies in the dendritic cells compared to the dendritic cell precursors. The transduced dendritic cell precursors can then be re-infused into the patient. This approach will result in transduced dendritic cell precursors which are not capable of expressing MART-1 themselves, but which are able to give rise to a renewable population of dendritic cells which are capable of expressing MART-1 at levels sufficient to permit a lifelong intermittent re-stimulation of a cytotoxic T lymphocyte (CTL) response to the MART-1 antigen.

6.3. Targeting Expression of a Protein to a Stem Cell but not to Progeny of the Stem Cell In an alternate embodiment, the target cell can be an undifferentiated cell wherein the protein is not expressible in said undifferentiated cell from a parent polynucleotide encoding the protein, at a level sufficient to effect a particular function associated with the protein. In such a case, at least one existing codon of the parent polynucleotide is replaced with a synonymous codon which has a higher translational efficiency in the undifferentiated cell compared to a differentiated cell. This results in a synthetic polynucleotide having altered translational kinetics compared to said parent polynucleotide wherein the protein is expressible in the undifferentiated cell at a level sufficient to effect a particular function associated with the protein, but wherein the protein is not expressible in differentiated cells derived from the undifferentiated cell at a level sufficient to effect said function.

This alternate embodiment may, by way of example, be used to permit expression of a transcriptional regulatory protein which, when expressed in a particular undifferentiated cell or stem cell, facilitates differentiation of the stem cell along a particular cell lineage. It will be appreciated that in such a case, the regulatory protein is normally expressed from a gene in which existing codons have low translational efficiencies in the stem cell and that therefore the protein is not normally capable of being expressed at levels sufficient to commit the stem cell to differentiate along a particular cell lineage. However, upon delivery of a parent polynucleotide encoding the protein and having altered codons (i.e. one or more first codons replaced with more highly efficiently translated synonymous codons), the protein can be expressed in the undifferentiated stem cell, thereby inducing differentiation of the stem cell into a desired cell lineage. It will also be apparent that such commitment to differentiate along a particular cell lineage can be utilized to prevent production of a particular lineage of cells such as cancer cells.

Alternatively, the method according to this embodiment can be used to express a transcriptional regulatory protein that is involved in the production of a therapeutic agent or agents. Such a protein can include, for example, NF-kappa-B transcription factor p65 subunit (NF-kappa-B p65) which is involved in the production of interleukin-2 (IL-2), interleukin-3 (IL-3) and granulocyte and macrophage colony stimulating factor (GMCSF). NF-kappa-B p65 is encoded naturally by a nucleotide sequence comprising a number of existing codons having low translational efficiencies in stem cells. Accordingly, such a sequence can be used as the sequence of a parent polynucleotide according to this embodiment. A suitable nucleotide sequence encoding this protein is described, for example, in Lyle et al (1994, *Gene* 138 265–266) and in the GenBank database as locus HUMNFKB65A, having Accession Number L19067, which are incorporated herein by reference.

A suitable undifferentiated cell which can be utilized in accordance with the present embodiment includes but is not limited to a stem cell, such as a CD34 positive hemopoetic stem cell.

The present embodiment can also be used advantageously for gene therapy where ongoing regulated expression of a transgene is desirable. For example, secure but reversible induction of fertility is desirable in veterinary practice and in humans. Such induction can be effected by transducing autologous breast ductal epithelial cells with a synthetic polynucleotide encoding a leutinising hormone (LH) antagonist or a leutinising hormone releasing hormone (LHRH) antagonist under the control of one or more regulatory polynucleotides. The synthetic polynucleotide can be produced by replacing existing codons of a parent polynucleotide with synonymous codons having high translational efficiencies in resting breast ductal epithelial cells compared to differentiated cells arising therefrom. Once the transduced cells are implanted back into the patient, expression can be switched off by oral administration of progestagen, forcing the differentiation of the majority of the stem cells and loss of expression of the antagonist. Once pregnancy is established, the suppression would be self-sustaining by the naturally produced progestagen. In one example of determining codon translational efficiencies according to this embodiment, the iso-tRNA composition of resting and estrogen-deprived breast epithelial cells can be established by first obtaining resting cells from reduction mammoplasty, and determining the cellular tRNA composition in the presence and absence of estrogen. The synthetic polynucleotide can be introduced into autologous resting epithelial cells by cell electroporation ex vivo, and the transduced cells can be subsequently transplanted subcutaneously into the patient. Progestagen can be administered as required to reverse induction of fertility.

6.4. Targeting Expression of a Toxin to a Tumor Cell but not to any Other Cells of the Mammal Many toxins and drugs are available that can kill tumor cells. However, these toxins and drugs are generally toxic for all dividing cells. This problem can be nevertheless ameliorated by establishing the iso-tRNA composition in a tumor clone, and constructing a synthetic toxin gene (e.g., ricin gene) or a synthetic anti-proliferation gene (e.g., the tumor suppressor p53) using synonymous codons corresponding to iso-tRNAs expressed at relatively high abundance in the tumor clone compared to normal dividing cells of the mammal. Alternatively, synonymous codons can be deduced from an analysis of the translational efficiencies of different codons in tumor cells compared to normal dividing cells to thereby construct the synthetic gene. The synthetic gene is then introduced into the patient by suitable means to selectively express the synthetic genes in tumor cells.

Alternatively, a chemotherapy enhancing product gene (i.e., a drug resistance gene e.g., the multi-drug resistance gene) having a codon pattern unlikely to be expressed efficiently in the tumor can be employed.

6.5. Targeting Gene Therapy to Control Body Fat

Leptins are proteins known to control satiety. By analogy with animal data, however, if too much leptin is administered to a patient, leptin-induced starvation can occur. Advantageously, a synthetic gene encoding leptin can be constructed including synonymous codons having high translational efficiencies in activated adipocytes compared to non-activated adipocytes. The synthetic gene can then be introduced into the patient by suitable means such that leptin is expressed in activated adipocytes and not expressed (or not substantially expressed) in non-activated adipocytes. As body fat turnover diminishes under the influence of leptin-reduced appetite, the metabolic activity of the adipocytes falls and the leptin production decreases correspondingly.

6.6. Targeting Expression of a Protein to a Stage of the Cell Cycle

In another embodiment of the invention, the target cell can be a non-cycling cell. In this case, the protein which is desired to be selectively expressed in the non-cycling cell is expressible in a cycling cell of the mammal from a parent polynucleotide at a level sufficient to effect a particular function associated with the protein. The synonymous codons are selected such that each has a higher translational efficiency in the non-cycling cell compared to the cycling cell. Accordingly, a synthetic polynucleotide is produced having altered translational kinetics compared to the parent polynucleotide wherein the protein is expressible in the non-cycling cell at a level sufficient to effect a particular function associated with said protein, but wherein the protein is not expressible in the non-cycling cell to effect said function.

7. Expressing a Protein in a Target Cell or Tissue by in vivo Expression of iso-tRNAs in the Target Cell or Tissue The invention also extends to a method wherein a protein can be selectively expressed in a target cell by introducing into the cell an auxiliary polynucleotide capable of expressing in the target cell one or more isoaccepting transfer RNAs which are not normally expressed in relatively high abundance in the target cell but which are rate-limiting for expression of the protein from a parent polynucleotide to a level sufficient for effecting a function associated with the protein. In this embodiment, introduction of the auxiliary polynucleotide sequence in the target cell changes the translational kinetics of the parent polynucleotide such that said protein is expressed at a level sufficient to effect a function associated with the protein.

The step of introducing the auxiliary polynucleotide sequence into the target cell or a tissue comprising a plurality of these cells can be effected by any suitable means. For example, analogous methodologies for introduction of the synthetic polynucleotide referred to above can be employed for delivery of the auxiliary polynucleotide into said target cell.

In practice, the choice of iso-tRNA supplied to a target cell using this method depends on whether the target cell in which protein expression is desired has a low or high abundance of that iso-tRNA and on whether the parent polynucleotide comprises codons corresponding to that iso-tRNA species. Thus, an iso-tRNA is supplied to the target cell by the auxiliary polynucleotide when that iso-tRNA is in relatively low abundance in the target cell and when parent polynucleotide comprises codons corresponding to that iso-tRNA species.

8. Assembly of Virus Particles in Cells Which do not Normally Permit Assembly of Virus Particles The invention also provides a method for producing a virus particle in a cycling eukaryotic cell. The virus particle comprises at least one protein necessary for virus assembly, wherein the at least one protein is not expressed in the cell from a parent polynucleotide at a level sufficient to permit virus assembly therein. This method is characterized by replacing at least one existing codon of the parent polynucleotide with a synonymous codon to produce a synthetic polynucleotide having altered translational kinetics compared to the parent polynucleotide such that the at least one protein is expressible from the synthetic polynucleotide in the cell at a level sufficient to permit virus assembly therein. The synthetic polynucleotide so produced is operably linked to one or more regulatory polynucleotides and is then introduced into the cell or a precursor cell thereof. The at least one protein is expressed subsequently in the cell in the presence of other viral proteins required for assembly of the virus particle to thereby produce the virus particle.

Advantageously, the synonymous codons, when compared to their corresponding existing codons, have higher translational efficiencies in the cycling cell compared to a non-cycling cell.

The cycling cell can be any cell in which the virus is capable of replication. Suitably, the cycling cell is a eukaryotic cell. Preferably, the cycling cell used for production of the virus particle is a eukaryotic cell line capable of being grown in vitro such as, for example, CV-1 cells, COS cells, yeast or spodoptera cells.

Suitably, the at least one protein of the virus particle is a viral capsid protein or capsomer. Suitable viral capsid proteins include, but are not restricted to, the L1 and/or L2 proteins of papillomavirus, VP1-3 of polyomavirus, VP1-6 of blue tongue virus, and the capsid proteins of adenovirus.

The other viral proteins required for assembly of the virus particle in the cell can be expressed from one or more other polynucleotides which suitably contain the rest of the viral genome. In the case of the at least one protein comprising L1 and/or L2 of papillomavirus, said other polynucleotide(s) preferably comprises the papillomavirus genome without the polynucleotides encoding L1 and/or L2.

In another embodiment, there is provided a method for producing a virus particle in a cycling cell wherein the virus particle comprises at least one protein that is necessary for assembly of the virus particle. In this embodiment, the protein is not expressed in the cycling cell from a parent polynucleotide at a level sufficient to permit virus assembly therein, and at least one existing codon of the parent polynucleotide is rate-limiting for the production of the at least one protein. The method includes introducing into the cell a polynucleotide capable of expressing therein an isoaccepting transfer RNA specific for said at least one codon.

The invention also provides virus particles made by any of the above methods, as well as cells or tissues containing therein the synthetic polynucleotides of the invention, or alternatively, cells or tissues produced from the methods of the invention.

The invention is further described with reference to the following non-limiting examples.

GENERAL DISCUSSION OF CERTAIN EXAMPLES

In the present specification the inventors have confirmed that one determinant of the efficiency of translation of a gene in mammalian cells is its codon composition. This observation has commonly been made when genes from prokaryotic organisms have been expressed in eukaryotic cells (Smith, D. W., 1996, *Biotechnol. Prog.* 12:417–422). The present inventors have also presented evidence that mRNA encoding the capsid genes of papillomavirus are not effectively translated in cultured eukaryotic cells, apparently because tRNA availability is rate limiting for translation, and that the block to PV late gene translation in eukaryotic cells in culture can be overcome by altering the codon usage of the late genes to match the consensus for mammalian genes, or alternatively by providing exogenous tRNAs. Alterations to mRNA secondary structure or protein binding (Sokolowski, et al., 1998, *J. Virol.* 72:1504–1515) as a consequence of the changes to the primary sequence of the PV capsid genes might contribute to the observed differences in efficiency of translation of the natural and modified PV capsid gene mRNAs in cultured cells. However, the enhancement of translation of the natural but not the modified mRNA that was observed after addition of tRNA in a mammalian in vitro translation system, which was not observed in a plant translation system, strengthens the argument that tRNA availability is rate limiting for translation of the natural gene in mammalian cells. A shortage of critical tRNAs could result in slowed elongation of the nascent peptide or premature termination of translation (Oba, et al., 1991, *Biochimie* 73:1109–1112). Slowed elongation appears to be the major consequence for the PV late gene. Analysis of codon usage in the PV genome shows that PV late genes use many codons that mammalian cells rarely use. For example, PV frequently uses UUA for leucine, CGU for arginine, ACA for threonine, and AUA for isoleucine, whereas these codons are significantly less often used in mammalian genes. In contrast, papillomavirus late genes can be expressed efficiently in yeast (Jansen, et al., 1995, *Vaccine* 13:1509–1514) (Sasagawa, et al., 1995, *Virology* 206:126–135) and the codon composition of yeast and papillomavirus genes are similar (Table 1). An apparent exception is that PV L1 genes can be efficiently expressed in insect cells (Kirnbauer, et al., 1992, Proc. Natl. Acad. Sci. USA 89:12180–12184) using recombinant baculovirus, or in various undifferentiated mammalian cells using recombinant vaccinia (Zhou, et al., 1991, Virology 185:251–257). As infection with vaccinia or baculovirus down regulates cellular protein synthesis, efficient expression of the L1 capsid proteins under these circumstances may occur because less cellular mRNA is available in a virus infected cell to compete with the L1 mRNA for the rarer tRNAs.

Codon composition could be a more general determinant of gene expression within different stages of differentiation of the same tissue. Although the genetic code is essentially universal, different organisms exhibit differences in codon composition of their genes, while the codon composition of genes tends to be relatively similar for all genes within each organism, and matched to the population of iso-tRNAs for that organism (Ikemura, T., 1981, J. Mol. Biol. 146:1–21). However, populations of tRNAs in differentiating and neoplastic cells are different (Kanduc, D., 1997, Arch. Biochem. Biophys. 342:1–6; Yang, and Comb, 1968, J. Mol. Biol. 31:138–142; Yang, and Novelli, 1968, Biochem. Biophys. Res. Commun. 31: 534–539) and the tRNA populations also vary in cells growing under different growth conditions (Doi, et al., 1968, J. Biol. Chem. 243:945–951). Accordingly, the inventors believe that codon composition and tRNA availability together provide a primitive mechanism for spatial and/or temporal regulation of gene expression. It is recognized that the G+C content of many dsDNA viruses, a crude marker for viral gene codon composition, is markedly different from the G+C content of the DNA of the cells they infect (Strauss, et al., 1995, "Virus Evolution" in Virology (eds. Fields, B. N., et al.), Lippincott-Raven, Philadelphia, pp. 153–171). Viruses may therefore have evolved to take advantage of codon composition to regulate their own program of gene expression, perhaps to avoid expression of lethal quantities of viral proteins in undifferentiated cells where the virus utilizes the cellular machinery to replicate its genome.

As the inventors' observations represent an apparently novel mechanism of regulation of gene translation within a single tissue, it is relevant to consider how this relates to previously proposed hypotheses for the restriction of expression of PV late genes to differentiated epithelium. A number of explanations have been proposed for the observation that PV late genes are only effectively expressed in differentiated epithelium. Reduced late gene transcription may reflect dependence of transcription from the late promoter on transcription factors expressed only in differentiated epithelium, or may alternatively be due to suppression of late promoter transcription by viral (Stubenrauch, et al., 1996, J. Virol. 70:119–126) or cellular gene products expressed in undifferentiated cells. The "late" promoters of HPV31b and of HPV5 (Haller, et al., 1995, Virology 214:245–255; Hummel, et al., 1992, J. Virol. 66:6070–6080) are described as differentiation dependent, although the search for relevant transcription control factors in differentiated keratinocytes by conventional footprinting and DNA binding studies has to date been unrewarding. Our data show that capsid proteins are not translated from PV L1 and L2 mRNAs in cells transfected with CMV promoter-based expression vectors (FIG. 2), suggesting that in addition to any transcriptional controls that may exist that there is a post-transcriptional block to capsid protein synthesis in undifferentiated cells. Sequences resembling 5' splice donor sites exist within L1 or L2 mRNA or within flanking untranslated message which are inhibitory to transcription of genes with which they are associated (Kennedy, et al., 1991, J. Virol. 65:2093–2097) (Furth, et al., 1994, Mol. Cell. Biol. 14:5278–5289). Other AU rich sequences in L1 or L2 mRNA promote mRNA degradation (Sokolowski, et al., 1997, Oncogene 15:2303–2319). These mechanisms inhibiting L1 and L2 expression in undifferentiated cells have yet to be shown to be inactive in differentiated epithelium, to explain the successful translation of late genes in this tissue.

Because inhibitory RNA sequences within the L1 coding sequence could have been rendered non-functional by the systematic codon substitution employed in the experiments described herein and the untranslated inhibitory sequences were not included in the inventors' test system, the respective roles of inhibitory sequences and codon mismatch in suppression of PV late gene expression in cultured mammalian cells cannot be determined. However, regulatory polynucleotides promoting RNA degradation or inhibiting translation are presumed to act through interaction with nuclear or cytoplasmic proteins (Sokolowski, et al., 1998, J. Virol. 72:1504–1515), and inefficient translation of native sequence L1 mRNA was observed in a cell free translation system from anucleate cells, demonstrating that codon composition of the PV late genes must play some role in regulation of PV late gene translation.

Further evidence supporting the hypothesis that codon composition is an important determinant of PV capsid gene expression was gathered from an analysis of the 84 PV L1 sequences currently available in GenBank. The codon composition of the L1 genes, and particularly the frequency of usage of the rarer codons, was essentially the same across all the published sequences as would be predicted by the similar G+C content of the papillomavirus genomes. The PV L1 gene is relatively conserved at the amino acid level, showing 60–80% amino acid homology between PV genotypes, as might be expected by the constraints on capsid protein function. There are, however, no obvious constraining influences on the codon composition of the PV late genes beyond those of the inventors' hypothesis, as the late gene region does not code for other genes, either in other reading frames or on the complementary DNA strand, and has no known cis acting regulatory functions. If codon composition of the capsid genes were not important for PV function, a considerable heterogeneity of codon usage might therefore be expected, given the evolutionary diversity of PVs (Chan, et al. 1995, J. Virol. 69:3074–3083).

Taken together, the data and evidence outlined herein makes a strong case that codon usage is a significant determinant of expression of PV late genes in undifferentiated and differentiated epithelial cells, and that this observation is generalizable. The relative role of message instability and codon mismatch in determining expression in differentiated tissues requires comparisons of transcriptional activity and translation of the L1 or L2 genes driven from strong constitutive promoters in differentiated and undifferentiated epithelium. Such work can be performed using either transgenic technology or keratinocyte raft cultures.

Although mechanisms of transcriptional regulation of PV L1 or L2 gene expression in the superficial layer of differentiated epithelium have been proposed (Zeltner et al., 1994, J. Virol. 68:3620; Brown, et al., 1995, Virology 214:259; Stoler et al., 1992, Hum. Pathol. 23:117; Hummel et al., 1995, J. Virol. 69:3381; Haller et al., 1995, Virology 214:245; Barksdale and Baker, 1993, J. Virol. 67:5605), measurable PV late gene mRNA is not always associated with production of late proteins (Zeltner et al., 1994, supra; Ozbun and Meyers, 1997, J. Virol. 71:5161), and the data presented here indicate that translation regulation can play a major part in controlling PV late gene expression. This observation has implications as herein described for the regulation of expression of genes related to the specialized functions of any differentiated tissue, and also for targeting of expression of therapeutic genes to such tissue while avoiding the potentially deleterious consequences of expression of the exogenous gene in a self renewing stem cell population.

Example 1

Expression of Synthetic L1 and L2 Protein in Undifferentiated Cells

Materials and Methods
Codon Replacements in the Bovine PV (BPV) L1 and L2 Genes

The DNA and amino acid sequences of the wild-type L1 (SEQ ID NOS:1,2) and L2 genes (SEQ ID NOS:5,6) are shown respectively in FIGS. 1A and 1B. To determine whether the presence of rare codons in wild-type L1 (SEQ ID NO:1) and L2 (SEQ ID NO:5) genes (Table 1) inhibited translation, we synthesized the L1 (SEQ ID NO:3) and L2 (SEQ ID NO:7) genes using synonymous substitutions as shown. To construct the synthetic sequences, we synthesized 11 pairs of oligonucleotides for L1 and 10 pairs of oligonucleotides for L2. Each pair of oligonucleotides has restriction sites incorporated to facilitate subsequent cloning (FIGS. 1A and 1B). The degenerate oligonucleotides were used to amplify L1 and L2 sequences by PCR using a plasmid with BPV1 genome as the template. The amplified fragments were cut with appropriate enzymes and sequentially ligated to pUC18 vector, producing pUCHBL1 and pUCHBL2. The synthetic L1 (SEQ ID NO:3) and L2 (SEQ ID NO:7) sequences were sequenced and found to be error-free, and then sub-cloned into the mammalian expression vector pCDNA3 containing SV40 ori (Invitrogen), giving expression plasmids pCDNA/HBL1 and pCDNA/HBL2. To compare expression of L1 and L2 with that of the original sequences, the wild type L1 (SEQ ID NO:1) and L2 (SEQ ID NO:5) genes were cloned into the pCDNA3 vector, resulting in pCDNA/BPVL1 wt and pCDNA/BPVL2 wt.
Immunofluorescence and Western Blot Staining For immunoblotting assays, COS-1 cells in 6-well plates were transfected with 2 μg L1 or L2 expression plasmids using lipofectamine (Gibco). 36 hrs after transfection, cells were washed with 0.15M phosphate buffered 0.9% NaCl (PBS) and lysed in SDS loading buffer. The cellular proteins were separated by 10% SDS PAGE and blotted onto a nitrocellulose membrane. The L1 or L2 proteins were identified by electrochemiluminescence (Amersham, UK), using BPV1 L1 (DAKO) or L2-specific (17) antisera. For immunofluorescent staining, COS-1 cells were grown on 8-chamber slides, transfected with plasmids, and fixed and permeabilised with 85% ethanol 36 hr after transfection. The slides were blocked with 5% milk-PBS and probed with L1 or L2-specific antisera, followed by FITC-conjugated anti-rabbit IgG (Sigma). For GFP or PGFP plasmid transfected cells, the cell were fixed with 4% buffered formaldehyde and viewed by epi-fluorescence microscopy.
Northern Blotting COS-1 cells transfected with various plasmids were used to extract cytoplasmic or total RNA using the QIAGEN Rneasy™ mini kit according to the supplier's handbook. Briefly, for cytoplasmic RNA purification, buffer RLN (50 mM Tris, pH 8.0, 140 mM NaCl, 1.5 mM $MgCl_2$ and 0.5% NP40) was directly added to monolayer cells and cells were lysed in 4° C. for 5 min. After the nuclei were removed by centrifugation, cytoplasmic RNA was purified by column chromatography. For total RNA extraction, the monolayer cells were lysed using buffer RLT supplied by the kit and RNA was purified by spin column. The purified RNAs were separated by 1.5% agarose gel in the presence of formaldehyde. The RNAs were then blotted onto nylon membrane and probed with (a) 1:1 mixed 5'-end labeled L1 wt and HBL1 fragments; (b) 1:1 mixed 5'-end labeled L2 wt and HBL2 fragments; (c) 1:1 mixed 5'-end labeled GFP and PGFP fragments or (d) randomly labeled PAGDH fragment. The blots were washed extensively at 65° C. and exposed to X-ray films for three days.
Results To test the hypothesis that the codon composition of the genes encoding the L1 and L2 capsid proteins of papillomavirus (PV) contributes to their preferential expression in differentiated epithelial cells, we produced synthetic BPV1 L1 (SEQ ID NO:3) and L2 (SEQ ID NO:7) genes, substituting codons preferentially used in mammalian genes for the codons frequently present in the wild type BPV1 L1 and L2 sequences which are rare in eukaryotic genes (FIGS. 1A, 1B).

For the L1 gene, a total of 202 base substitutions were made in 196 codons, without changing the encoded amino acid sequence (FIG. 1A). This synthetic "humanized" BPV L1 gene (SEQ ID NO:3) was designated HBL1. In a similarly modified BPV1 L2 gene (SEQ ID NO:7) designated HBL2, 303 bases were changed to substitute 290 less frequently used codons with the corresponding preferentially used codons. Using the synthetic HBL1 (SEQ ID NO:3) and HBL2 (SEQ ID NO:7) genes, we constructed two eukaryotic expression plasmids based on pCDNA3, and designated pCDNA/HBL1 and pCDNA/HBL2. Similar expression plasmids, constructed with the wild type BPV1 L1 (SEQ ID NO:1) and BPV1 L2 (SEQ ID NO:5) genes, were designated pCDNA/BPVL1 wt and pCDNA/BPVL2wt, respectively. In each of these plasmids, the SV40 ori allowed replication in COS-1 cells, and the L1 or L2 gene was driven by a strong constitutive CMV promoter.

Figures 1, 2, 3A, 3B:
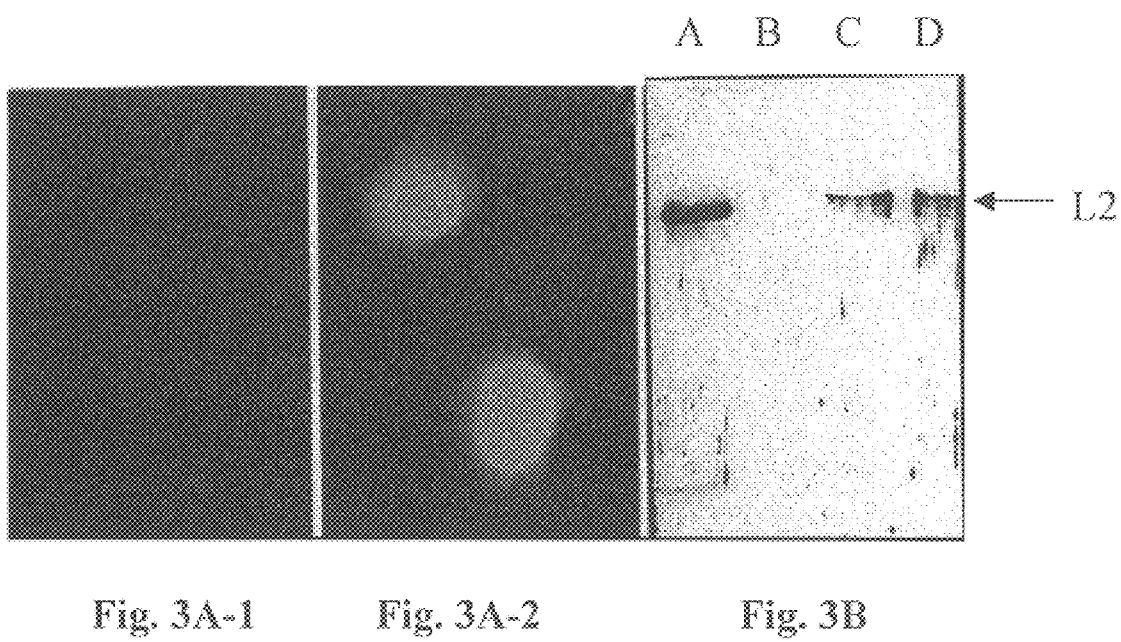

To compare the expression of the synthetic humanized and the wild type BPV1 L1 or BPV1 L2 genes, we separately transfected COS-1 cells with each of the L1 and L2 plasmids described above. Transfected cells were analyzed for expression of L1 (SEQ ID NO:2, 4) or L2 (SEQ ID NO:6, 8) protein by immunofluorescence 36 hr after transfection (FIGS. 2A and 3A). Cells transfected with the pCDNA3 expression plasmid containing the synthetic humanized L1 (SEQ ID NO:3) or L2 (SEQ ID NO:7) genes were observed to produce large amounts of the corresponding protein, while cells transfected with expression plasmids with the wild type L1 (SEQ ID NO:1) or L2 (SEQ ID NO:5) sequences produced no detectable L1 or L2 protein (FIGS. 2A and 3A, see nuclear staining of L1 and L2 proteins). To compare more accurately expression of the different L1 and L2 constructs, L1 and L2 protein expression was assessed by immunoblot in COS-1 cells transfected with the wild type or synthetic humanized BPV1 L1 or L2 pCDNA3 expression constructs (FIGS. 2B and 3B) Large amounts of immunoreactive L1 and L2 proteins were expressed from the synthetic humanized L1 (SEQ ID NO:3) and L2 (SEQ ID NO:7) sequences, but no L1 or L2 protein was expressed from the wild type L1 and L2 sequences (SEQ ID NO:1, 5).

Figure 2C:
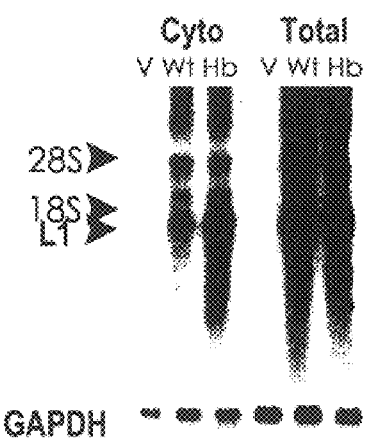
FIG. 2C is an image which depicts a Northern blot in which L1 mRNA extracted from transfected cells was probed with $^{32}$P-labeled probes produced from wild type L1 sequence. The amount of mRNA loaded in respective lanes was examined by hybridization of the mRNA sample with a gapdh probe.
Figure 3C:
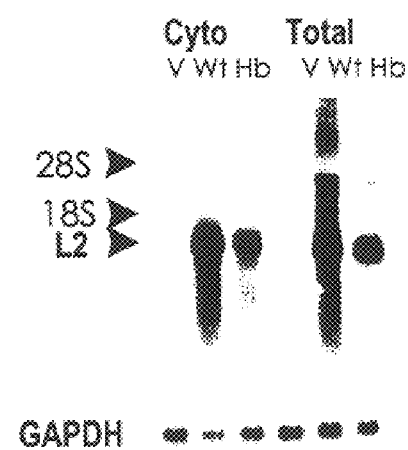
FIG. 3C is an image which depicts a Northern blot in which L2 mRNA extracted from transfected cells was probed with $^{32}$P-labeled probes produced from wild type L2 sequence. The amount of mRNA loaded in respective lanes was examined by hybridization of the mRNA sample with a gapdh probe.

To establish whether the alterations to the primary sequence of the L1 and L2 mRNA that resulted from the codon alterations also affected steady state expression of the corresponding message, mRNA was prepared from COS-1 cells transfected with the various capsid protein gene constructs. Using GAPDH as an internal standard, it was established by Northern blot that two to three times more modified than wild type L1 mRNA, and similar levels of wild type and modified L2 mRNA were present in the cytoplasm of transfected cells (FIGS. 2C and 3C). The amount of L1 or L2 protein expressed per arbitrary unit of L1 or L2 mRNA was at least 100 fold higher for the humanized gene constructs than for the natural gene constructs.

In a comparative study, the wild-type and humanized L1 gene were also transfected into five laboratory cell lines representative of different tissue types (CV-1, COS 1, 3T3, HL-60 and pTET). As expected from the above results, the humanized L1 gene is well expressed in CV-1 cells (of epithelial origin), and in COS-1 cells, which are similar in origin, whereas the wild-type gene is not detectably expressed in these cells. Both constructs were also found to be poorly expressed in undifferentiated HL-60 cells (of hemopoetic origin), and in 3T3 cells (of mesenchymal origin), whereas the wild-type gene but not the humanized gene was expressed in pTET.

Example 2

Papillomavirus Late Protein Translation in vitro

Materials and Methods
In vitro Translation Assay

One microgram of each plasmid was incubated with 20 $\mu$Ci $^{35}$S-methionine (Amersham) and 40 $\mu$L T7 coupled rabbit reticulocyte or wheat germ lysates (Promega). Translation was performed at 30° C. and stopped by adding SDS loading buffer. The L1 proteins were separated by 10% SDS PAGE and examined by autoradiography.

Production of Aminoacyl-tRNA $2.5 \times 10^{-4}$ M tRNA (Boehringer) was added to a 20 $\mu$L reaction containing 10 mM Tris-acetate, pH.7.8, 44 mM KCl, 12 mM MgCl$_2$, 9 mM -mercaptoethanol, 38 mM ATP, 0.25 mM GTP and 7 $\mu$L rabbit reticulocyte extract. The reaction was carried out at 25° C. for 20 min, and 30 $\mu$L H$_2$O was added to the reaction to dilute the tRNAs to $1 \times 10^{-4}$ M. The aminoacyl-tRNAs were then aliquoted and stored at $-70°$ C.

Results

Figure 4A:
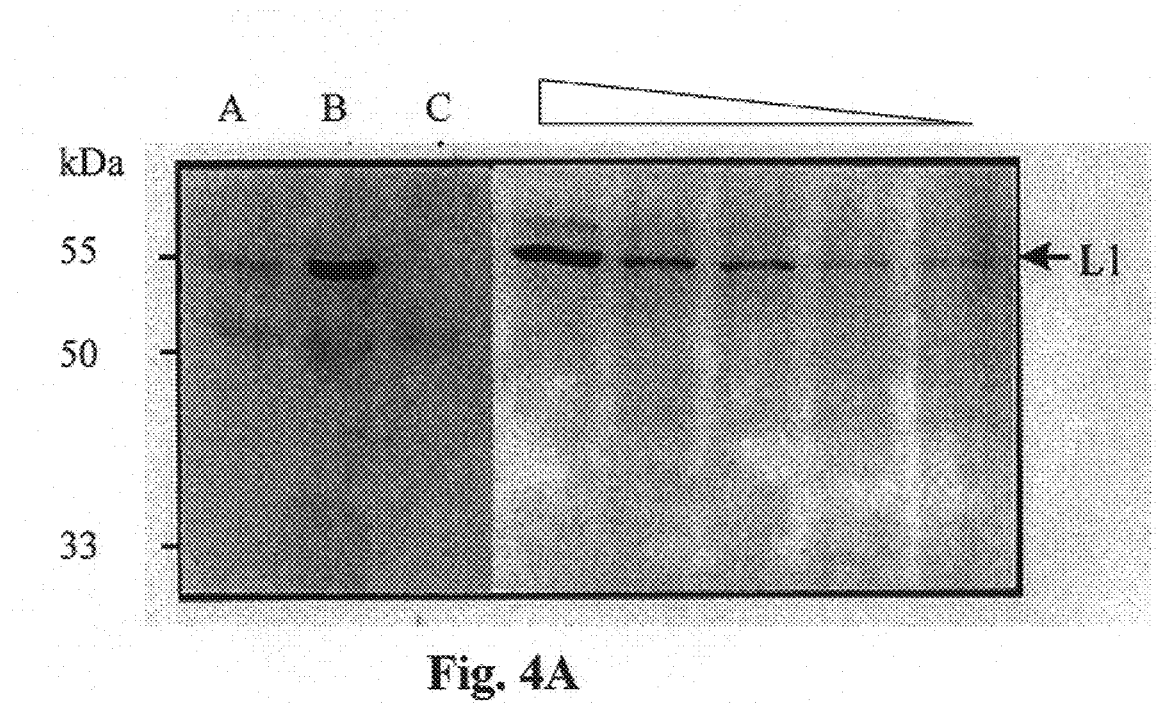
FIGS. 4A and 4B, is a series of images which depict in vitro translation of BPVL1 sequences, wild type BPVL1 (wt) or synthetic L1 (HB) using rabbit reticulocyte lysate or wheat germ extract in the presence of $^{35}$S-methionine.
Figure 4B:
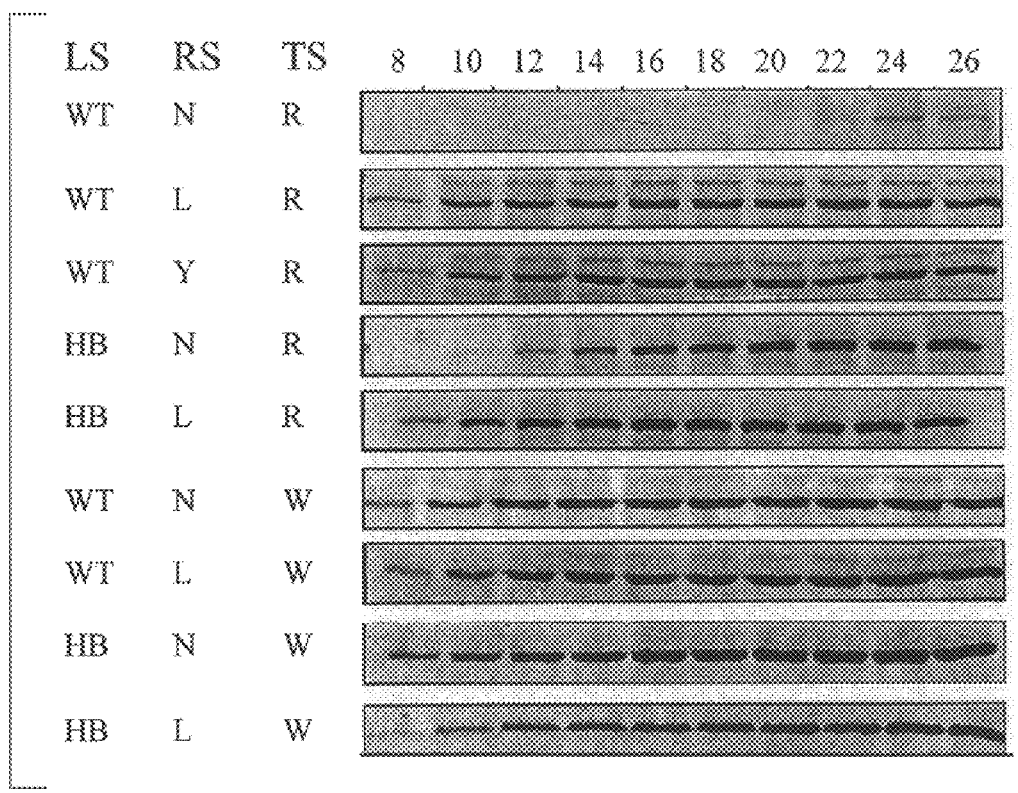

As the major limitation to expression of the wild type BPV L1 and L2 genes appeared to be translational in our system, we wished to test whether this limitation reflected a limited availability of the appropriate tRNA species for gene translation. As transient expression of the synthetic genes within intact cells can be regulated by many factors, we tested our hypothesis in a cell free system using rabbit reticulocyte lysate (RRL) or wheat germ lysate to examine gene translation. Similar amounts of plasmids expressing the wild type or synthetic humanized BPV1 L1 gene were added to a T7-DNA polymerase coupled RRL transcription/translation system in the presence of $^{35}$S-methionine. After 20 minutes, translated proteins were separated by SDS PAGE and visualized by autoradiography. Efficient translation of the modified L1 gene was observed (FIG. 4A, lane 2), while translation of the wild type BPV1 L1 sequence resulted in a weak 55 kDa L1 band (FIG. 4A, lane 1). We reasoned that although the wild type sequence was not optimized for translation in RRL, some translation would occur, as there would be no cellular mRNA species competing for the 'rare' codons present in the wild type L1 sequence. The above data suggest that the observed difference in efficiency of translation of the wild type and synthetic humanized L1 genes is a consequence of limited availability of the tRNAs required for translation of the rare codons present in the wild type gene. We therefore expected that addition of excess tRNA to the in vitro translation system would overcome the inhibition of translation of the wild type L1 gene. To address this question, $10^{-5}$ M aminoacyl-tRNAs from yeast were added into the RRL translation system, and L1 protein synthesis was assessed. Introduction of exogenous tRNAs resulted in a dramatic improvement in translation of the wild type L1 sequence, which now gave a yield of L1 protein comparable to that observed with the synthetic humanized L1 sequence (SEQ ID NO:3) (FIG. 4A). Enhancement of translation of the wild type L1 gene (SEQ ID NO:1) by aminoacyl-tRNA was dose-dependent, with an optimum efficiency at $10^{-5}$ M tRNA. As addition of exogenous tRNA improved the yield of L1 protein translated from the wild type L1 gene sequence (SEQ ID NO:1), we assessed the speed of translation of wild type and humanized L1 mRNA. Samples were collected from the translation mixture every 2 minutes, starting at the 8th minute. Translation of L1 (SEQ ID NO:2, 4) from the wild type sequence (SEQ ID NO:1) was much slower than from the humanized L1 sequence (SEQ ID NO:3) (FIG. 4B), and the retardation of translation could be completely overcome by adding exogenous tRNA from commercially available yeast tRNA. Yeast tRNA was chosen in the above analysis because the codon usage in yeast is similar to that of papillomavirus (Table 1). Addition of exogenous tRNA did not significantly improve the translation of the humanized L1 gene (SEQ ID NO:3), indicating that this sequence was optimized with regard to codon usage for the rabbit reticulocyte translation machinery (FIG. 4B). In separate experiments we established that wt L1 translation could also be enhanced by liver tRNA (FIG. 4), and by tRNAs extracted from bovine skin epidermis, which presumably constitutes a mixture of tRNAs from differentiated and undifferentiated cells.

Example 3

Translation of Wild Type L1 is Efficient in Wheat Germ Extract

To further test our hypothesis that tRNA availability is a determinant of expression of the wild type BPV1 L1 gene (SEQ ID NO:1), we examined translation of L1 in a cell type in which a quite different set of tRNAs would be available. In a wheat germ translation system, wild type L1 mRNA was translated as efficiently as humanized L1 mRNA, and addition of exogenous aminoacyl-tRNAs did not improve the translation efficiency of either wild type or humanized sequences (FIG. 4B). This indicated that in wheat germ there are sufficient of the tRNAs which are limiting for translation of wild type L1 sequence in RRL to allow efficient L1 translation.

Example 4

Modified Late Genes Can Be Expressed in Undifferentiated Cells from Papillomavirus Promoter(s)

Figures 1, 2, 3, 4, 5A, 5B:
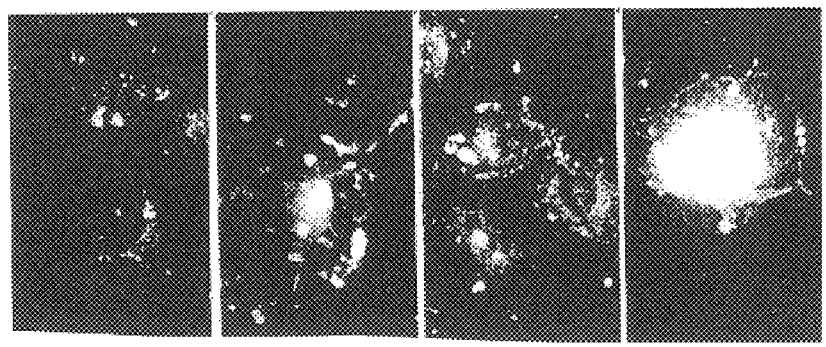

While our data presented above indicates that translation is limiting for the production of BPV1 capsid proteins in our test system, these experiments were conducted in systems which are not truly representative of the viral late gene transcription from the BPV genome, in part because the genes were driven by a strong CMV promoter. We therefore wished to establish whether synthetic humanized BPV capsid protein mRNA would be translated more efficiently than the wild type mRNA, if transcribed from the natural BPV1 promoter. This would establish whether translation was indeed one of the limiting factors for expression of BPV1 late genes driven from the natural cryptic late gene promoter in an undifferentiated cell. The BPV genome was cleaved at nt 4450 and 6958 with BamHI/HindIII and the original L1 (nt 4186–5595) and L2 (5068–7095) ORFs were removed. The synthetic humanized L2 gene (SEQ ID NO:7), together with an SV40 ori sequence to allow plasmid replication in eukaryotic cells, were inserted into the BPV genome lacking L1/L2 ORF sequences. This plasmid (FIG. 5A) was designated pCICR1. A similar plasmid was constructed with wild type (SEQ ID NO:5) rather than synthetic humanized L2 and designated pCICR2. Cos-1 cells were transfected with these plasmids and L2 protein expression examined by immunofluorescence of transfected cells. Synthetic humanized L2 (SEQ ID NO:7), driven by the natural BPV-1 promoter, was efficiently expressed, whereas the wild type L2 sequence (SEQ ID NO:5), driven from a similar construct, produced no immunoreactive L2 protein (SEQ ID NO:6,8) (FIG. 5B). As undifferentiated cells supported the expression of the humanized L2 gene (SEQ ID NO:7) but not the wild type L2 (SEQ ID NO:5) expressed from the cryptic late BPV promoter, the results confirmed our earlier observations from experiments using the CMV promoter. However, the plasmids tested here contained SV40 ori, designed to replicate the DNA in Cos cells. The increased copy number of the BPV1 L2 plasmids or the transcriptional enhancing activity of the SV40 ori might explain in part the increased efficiency of expression of L2 in this experimental system when compared with infected skin. However, the marked difference in expression between the natural and humanized genes seen with a CMV promoter construct is still observed with the natural promoter.

Example 5

Substitution of Papillomavirus-preferred Codons Prevents Translation but not Transcription of a Non-papillomavirus Gene in Undifferentiated Cells Materials and Methods
Codon Replacement in gfp Gene To construct a modified gfp gene (SEQ ID NO:11) using papillomavirus preferred codons (PGFP), 6 pairs of oligonucleotides were synthesized. Each pair of oligonucleotides has restriction sites incorporated and was used to amplify gfp using a humanized gfp gene (SEQ ID NO:9) (GIBCO) as template. The PCR fragments were ligated into the pUC18 vector to produce pUCPGFP. The PGFP gene was sequenced, and cloned into BamHI site of the same mammalian expression vector, pCDNA3, under the CMV promoter. The DNA and deduced amino acid sequences of the humanized gfp gene are shown in FIGS. 1C. Mutations introduced into the wild type gfp gene (SEQ ID NO:9) to produce the Pgfp gene (SEQ ID NO:11) are indicated above the corresponding nucleotide residues of the wild-type sequence.

Results

Figures 1, 2, 3, 6A:
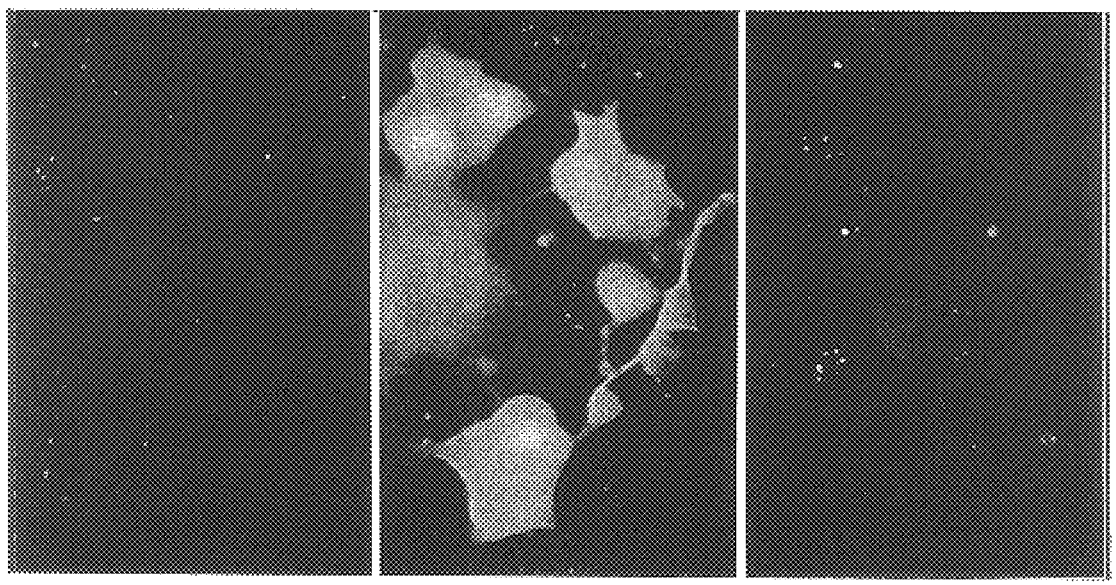
Figure 6B:
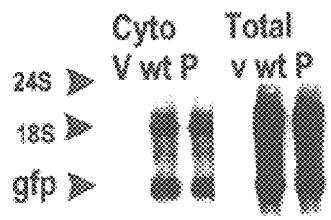
FIG. 6B is an image which depicts a Northern blot in which mRNA extracted from cells transfected with gfp or P gfp was probed with $^{32}$P-labeled gfp, using gapdh as a reference gene.

To further confirm that condon usage can alter gene expression in mammalian cells, we made a further variant on a synthetic gfp gene modified for optimal expression in eukaryotic cells (Zolotukhin, et al., 1996. *J. Virol.* 70:4646–4654). In our variant, codons optimized for expression in eukaryotic cells were substituted by those preferentially used in papillomavirus late genes. Of 240 codons in the humanized gfp gene (SEQ ID NO:9), which expresses high levels of fluorescent protein in cultured cells, 156 were changed to the corresponding papillomavirus late gene-preferred codons to produce a new gfp gene (SEQ ID NO:11) designated Pgfp. Expression of Pgfp (SEQ ID NO:11) in undifferentiated cells was compared with that of humanized gfp (SEQ ID NO:9). COS-1 cells transfected with the humanized gfp (SEQ ID NO:9) produced a bright fluorescent signal after 24 hrs, while cells transfected with Pgfp (SEQ ID NO:11) produced only a faint fluorescent signal (FIG. 6A-3). To confirm that this difference reflected differing translational efficacy, gfp specific mRNA was tested in both transfections and found not to be significantly different (FIG. 6B). Thus, codon usage and corresponding tRNA availability apparently determines the observed restriction of expression of PV late genes, and modification of codon usage in other genes similarly prevents their expression in undifferentiated cells.

Example 6

PGFP with Papillomavirus-preferred Codons is Efficiently Expressed in vivo in Differentiated Mouse Keratinocytes Materials and Methods
Delivery of Plasmid DNA into Mouse Skin by Gene Gun Fifty microgram of DNA was coated onto 25 μg gold micro-carriers by calcium precipitation, following the manufacturer's instructions (Bio-Rad). C57/bl mouse skin was bombarded with gold particles coated with DNA plasmid at a pressure of 600 psi. Serial sections were taken from the skin and examined for distribution of the particles, confirming that a pressure of 600 psi could deliver particles throughout the epidermis.

Results

Figure 7:
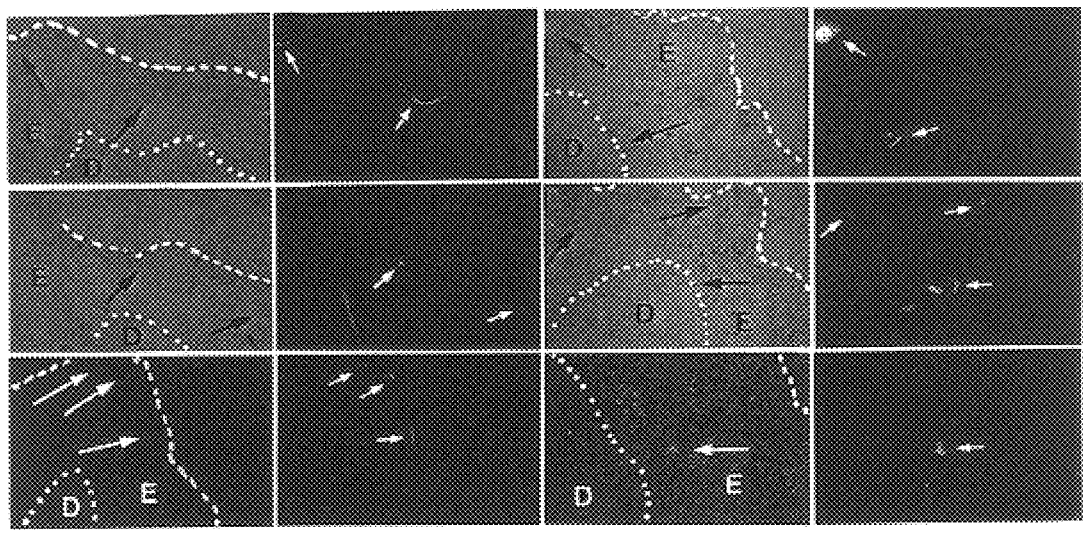
FIG. 7, comprising

Mice were shot with gold beads carrying PGFP DNA plasmid and, 24 hrs later, skin samples were cut from the site of DNA delivery and examined for expression of GFP protein (SEQ ID NO:10, 12). Fluorescence was detected mostly in upper keratinocyte layers, representing the differentiated epithelium, and was not seen in undifferentiated basal cells. In contrast, skin sections shot with the humanized GFP plasmid showed fluorescence in cells randomly distributed throughout the whole epidermis (FIG. 7). Although GFP-positive cells were rare in both PGFP- (SEQ ID NO:11) and GFP-inoculated (SEQ ID NO:9) mouse skin, fluorescence was observed only in differentiated strata in the PGFP sample (SEQ ID NO:11), whereas fluorescence was observed throughout the epidermis in GFP-inoculated (SEQ ID NO:9) mouse skin. This result confirmed that the use of papillomavirus-preferred codons resulted in the protein being expressed in an epithelial differentiation-dependent manner.

Example 7

Microinjection of Yeast tRNA and Wild Type L1 Gene into Cultured Cells

To test if yeast tRNA could facilitate expression of wild type BPV-1 L1 (SEQ ID NO:1) (as yeast uses a similar set of codons to those observed in papillomavirus for its own genes), 2 pL of mixtures containing tRNA (2 mg/mL) (purified yeast tRNA (Boehringer Mannheim) or bovine liver tRNA—control) and BPV L1 DNA (2 µg/mL) can be injected into CV-1 cells (Lu and Campisi, 1992, *Proc. Natl. Acad. Sci. U.S.A.* 89 3889–3893). The injected cells can then be cultured for 48 hrs at 37° C. and examined for expression of L1 gene by standard immunofluorescence methods using BPV L1-specific antibody and quantified by FACS analysis (Qi et al 1996, *Virology* 216 35–45).

Example 8

Establishment of a Cell Line which can Continuously Produce HPV Virus Particles

To produce infectious PV, various methods have been tried including the epithelial raft culture system (Dollard et al 1992, *Genes Dev* 6 1131–1142), and cell lines containing BPV-1 episomal DNA, and infected by BPV-1 L1/L2 recombinant vaccinia (Zhou et al 1993, *J. Gen. Virol.* 74 763–768) or transfected by SFV RNA (Roden et al 1996, *J. Virol.* 70 5875–5883). The yield of particles is in each case low. In a reduction to practice of our discovery, synthetic BPV L1 (SEQ ID NO:3) and L2 genes (SEQ ID NO:7) (as described in Example 1) can be used to produce infectious BPV in a cell line containing BPV-1 episomal DNA. Fibroblast cell lines (CON/BPV) containing BPV-1 episomal DNA (Zhou et al 1993, *J. Gen. Virol.* 74 763–768) can be used for transfection of the synthetic BPV-1 L1 (SEQ ID NO:3) and L2 genes (SEQ ID NO:7) under control of CMV promoter. BPV particles can then be purified from the cell lysate and the purified particles examined for the presence of BPV-1 genome. Standard methods such as transfection with lipofectamine (BRL) and G418 selection of transfected cells can be utilized to generate suitable transfectants expressing humanized L1 (SEQ ID NO:3) and L2 (SEQ ID NO:7) in the background of BPV-1 episomal DNA. Examination of L1 and L2 protein expression can be performed using rabbit anti-BPV L1 or rabbit anti-BPV L2 polyclonal antibodies. BPV particles can then be purified using our published methods (Zhou et al 1995, *Virology* 214 167–176) and can be characterized by electron microscopy and DNA blotting. The infectivity of BPV particles isolated from the cultured cells can be tested in focus formation assays using C127 fibroblasts.

Example 9

Analysis of tRNA Composition

Method for Extracting and Measuring tRNA from Tissues

Tissue(100 g) is homogenized in a Waring™ Blender with 150 mL of phenol (Mallinckrodt, Analytical Reagent, 88%) saturated with water (15:3) and 150 mL of 1.0 M NaCl, 0.005 M EDTA in 0.1 M Tris-chloride buffer, pH 7.5. The homogenate was spun for ten minutes at top speed in the International clinical centrifuge and the upper layer was carefully decanted off. To this aqueous layer, three volumes of 95% ethanol were added. The resultant precipitate was spun down at top speed in the Internationals clinical centrifuge and re-suspended in 250 mL of 0.1 M Tris/chloride buffer, pH 7.5. This solution was added (flow rate of 15–20 drops per minute) to a column (2×10 cm) of 2 g of DEAE-cellulose previously equilibrated with cold 0.1 M Tris-chloride buffer pH 7.5. The column was then washed with 1 L of Tris-chloride buffer, pH 7.5 and the RNA eluted with 1.0 M NaCl in 0.1 M Tris-chloride buffer, pH 7.5. The first 10 mL of NaCl solution were discarded as "hold-up." Sufficient salt solution (60–80 mL) was then collected until the optical density of the effluent was less than three at 260 nm. This solution was extracted twice with an equal volume of phenol saturated with water and twice with ether. To the aqueous solution containing the RNA, three volumes of 95% ethanol were added and the solution wag allowed to stand overnight in the cold. The precipitate was spun down and washed first with 80% and then twice with 95% ethanol and dried in a vacuum. Approximately 60 mg of soluble RNA were obtained from a 100-g lot of rat liver.

Quantitating tRNAs

The following nylon membranes are used: Biodine™ A and B (PALL). For the preparation of dot blots, the tRNA samples (from 1 pg to 5 ng) are denatured at 60° C. for 15 min in 1–5 µL of 15% formaldehyde. 10×SSC (SSC is NaCl 0.3 M, tri-sodium citrate 0.03 M). The samples are spotted in 1 µL aliquots onto the membranes that have been soaked for 15 min in deionized water and slightly dried between two sheets of 3MM Whatman™ paper prior to the application of the samples. The tRNAs are fixed covalently (in the membranes by ultraviolet-irradiation (10 mm using an ultraviolet lamp at 254 nm and 100 W strength at a distance of 20 cm) and the membranes are baked for 2–3 h at 80° C.

A 5' end labeled synthetic deoxyribo-oligonucleotide complementary to the A54-A73 sequence of the tRNA is used as a probe for the hybridization experiments. Labeling of the oligonucleotide is performed by direct phosphorylation of the 5'-OH ended probe.

For hybridization experiments, the UV-irradiated 20 membranes are first pre-incubated for 5 h at 50° C. in 50% deionized formamide, 5×SSC, 1% SDS, 0.04% Ficoll™ 0.04% polyvinylpyrrolidone and 250 µL/mL of sonicated salmon sperm DNA using 5 mL of buffer for 100 cm² of membrane. Hybridization is finally performed overnight at 50° C. in the above solution (2.5 mL/100 cm²) where the labeled probe has been added. After hybridization, the membranes are washed twice in 2×SSC, 0.1% SDS for 5 min at room temperature, twice in 2×SSC, 1% SDS for 30 mm at 60° C. and finally in 0.1×SSC. 0.1% SDS for 30 min at room temperature. To detect 30 the hybridized probes the membranes are exposed for 16 h to Fuji™ XR film at 70° C. with an intensifying screen.

Sequence of tRNA Probes

The sequences of the tRNA probes are as follows:

Ala$^{GCA}$: 5'-TAAGGACTGTAAGACTT (SEQ ID NO:13)
Arg$^{CGA}$: 5'-CGAGCCAGCCAGGAGTC (SEQ ID NO:14)
Asn$^{AAC}$: 5'-CTAGATTGGCAGGAATT (SEQ ID NO:15)
Asp$^{GAC}$: 5'-TAAGATATATAGATTAT (SEQ ID NO:16)
Csy$^{TGC}$: 5'-AAGTCTTAGTAGAGATT (SEQ ID NO:17)
Glu$^{GAA}$: 5'-TATTTCTACACAGCATT (SEQ ID NO:18)
Gln$^{CAA}$: 5'-CTAGGACAATAGGAATT (SEQ ID NO:19)
Gly$^{GGA}$: 5'-TACTCTCTTCTGGGTTT (SEQ ID NO:20)
His$^{CAC}$: 5'-TGCCGTGACTCGGATTC (SEQ ID NO:21)
Ile$^{ATC}$: 5'-TAGAAATAAGAGGGCTT (SEQ ID NO:22)
Leu$^{CTA}$: 5'-TACTTTTATTTGGATTT (SEQ ID NO:23)

Leu$^{CTT}$: 5'-TATTAGGGAGAGGATTT (SEQ ID NO:24)
Lys$^{AAA}$: 5'-TCACTATGGAGATTTTA (SEQ ID NO:25)
Lys$^{AAG}$: 5'-CGCCCAACGTGGGGCTC (SEQ ID NO:26)
Met$^{elong}$: 5'-TAGTACGGGAAGGATTT (SEQ ID NO:27)
Phe$^{TTC}$: 5'-TGTTTATGGGATACAAT (SEQ ID NO:28)
Pro$^{CCA}$: 5'-TCAAGAAGAAGGAGCTA (SEQ ID NO:29)
Pro$^{CCI}$: 5'-GGGCTCGTCCGGGATTT (SEQ ID NO:30)
Ser$^{AGC}$: 5'-ATAAGAAAGGAAGATCG (SEQ ID NO:31)
Thr$^{ACA}$: 5'-TGTCTTGAGAAGAGAAG (SEQ ID NO:32)
Tyr$^{TAC}$: 5'-TGGTAAAAAGAGGATTT (SEQ ID NO:33)
Val$^{GTA}$: 5'-TCAGAGTGTTCATTGGT (SEQ ID NO:34)

Example 10

Comparison of the Relative Abundance of tRNA Species in Undifferentiated and Differentiated Keratinocytes Materials and Methods Isolation of Epidermal Cells 2-day old mice were killed and their skins removed. The skins were digested with 0.25% trypsin PBS at 4° C. overnight. The epidermis was separated from the dermis using forceps and minced with scissors in 10% FCS DMEM medium. The cell suspension was first filtered through a 1 mm and then a 0.2 mm nylon net. The cell suspension was then pelleted and washed twice with PBS.

Density Gradient Centrifugation

The keratinocytes were re-suspended in 30% Percoll and separated by centrifugation through a discontinuous Percoll gradient (1.085, 1.075 and 1.050 g/mL) at 1200×g at room temperature for 25 min. The cells were then washed with PBS and used to extract tRNA.

tRNA Purification

The cells were lysed in 5 mL of lysis buffer (0.2 M NaOH, 1% SDS) for 10 min at room temperature. The lysate was neutralized with 5 mL of 3.0 M potassium acetate (pH 5.5). After centrifugation, the supernatant was diluted with 3 volumes of 100 mM Tris (pH 7.5) and added to a DEAE column equilibrated with 100 mM Tris (pH 7.5). An equal volume of isopropanol was added to the aqueous solution containing tRNA, and the solution was allowed to stand overnight at 4° C. The tRNA was spun down and washed with 75% ethanol, then dissolved in RNase-free water.

tRNA Blotting

Ten nanograms of each tRNA sample in 1 μL was denatured in 60° C. for 15 min in 4 pL formaldehyde and 5 μL 20×SSC. The samples were spotted in 1 μL aliquots onto charged nylon membrane (Amersham), and the tRNAs were fixed with UV and probed with $^{32}$P-oligonucleotides.

Results

Comparison of the abundance of the tRNA species in undifferentiated and differentiated keratinocytes showed that the levels of some tRNA populations changed dramatically. For example, the levels of tRNAs specific for Ala$^{GCA}$, Leu$^{CTT}$, Leu$^{CTA}$ were increased in differentiated cells while tRNAs for Arg$^{CGA}$, Pro$^{CCI}$, Asn$^{AAC}$ were more abundant in undifferentiated keratinocytes (see Table 2).

Example 11

Construction of Expression Vectors for Determining Relative Codon Preferences in Mammalian Cells Synthetic gfp genes were constructed in which a single artificial start codon (ATG) followed by a stretch of five identical codons is fused in frame immediately upstream of a gfp coding sequence. A reverse oligonucleotide primer (SEQ ID NO:219; sequence complementary to the termination codon for GFP, is underlined), and a suite of forward oligonucleotide primers (SEQ ID NO: 160 through 218; the first codon of GFP, is underlined) were synthesized and used for PCR amplification of a humanized gfp gene (SEQ ID NO:158) (GIBCO) as template with Taq DNA polymerase (Amplification parameters: 95° C./30 sec; 52° C./30 sec; 72° C./1 min; 30 cycles). The amplified fragments have nucleic acid sequences and deduced amino acid sequences as shown in SEQ ID NO:35 through 157.

In summary, the synthetic fragments contain an artificial start codon followed by a tandem repeat of five identical codons specific for a given iso-tRNA species. The tandem repeat immediately precedes the second codon of the gfp gene. The synthetic fragments by SEQ ID NO, and encoded tandem repeat, are presented in the TABLE 3.

The amplified fragments were cloned between the EcoRI and KpnI sites of the mammalian expression vector pCDNA3 containing SV40 ori (Invitrogen) and the CMV promoter.

Transfection of COS-1 Cells

COS-1 cells were grown continuously in DMEM media supplemented with 10% fetal calf serum (FCS), glutamine, penicillin and streptomycin. Cells were passaged from a 150 cm$^2$ flask into multiple 25 cm$^2$ flasks. Cells were transfected using a QIAGEN Effectene™ transfection kit (and the manufacturer's instructions, incorporated herein by reference) when confluency of the cells was between 60–80%. Briefly, 1 μg of plasmid DNA was diluted into 10 μL of filtered TE buffer and 140 μL of QIAGEN™ Buffer EC. Eight microliters of QIAGEN™ Enhancer was added followed by vortexing and incubation at room temperature for 2–5 min. QIAGEN™ Effectene (10 μL) was added followed by vortexing for 10 seconds and a further incubation at room temperature for 10 min. The cells were washed once in 1×PBS followed by re-suspension in fresh media (1 mL). After 48 hrs, cells were harvested and washed in 1×PBA (phosphate buffered saline plus azide). Cells adhering to the flask were removed by scraping with a cell scraper. Cells were then filtered through a 70 μm filter before addition of 300 μL of 2% paraformaldehyde and 300 μL of 10 ×FCS. Cells were kept on ice in the dark until FACS analysis.

Synthetic gfp mRNA expression of transfected cells was tested by reverse transcriptase PCR. GFP protein expression was analyzed by confocal microscopy and flow cytometry.

Confocal Microscopy

Transfected COS-1 cells were examined using a Bio-Rad MRC-600 laser-scanning confocal microscope equipped with a krypton-argon laser and filter sets suitable for the detection of fluorescein and Texas red dyes (Bio-Rad KlyK2), and a Nikon 603 PlanApo™ numerical aperture 1.2 water-immersion objective. Dual-channel confocal images and video montages of the transfected cells can be suitably composed using ADOBE PhotoShop™.

Flow Cytometry

Transfected COS-1 cells were analyzed with a Becton Dickinson™ Flow cytometer Elite II. Omega Filters™ allowed detection of green fluorescence emission (EMI510/20—collects light from 490–530 nm) and yellow fluorescence emission (EM2 550/30—collects light form 525–580 nm) from the transfected cells.

Results

A series of 64 reporter constructs (see TABLE 3) was made and validated, in which the gfp gene is preceded in frame by a tandem repeat of 5 identical codons. Together, the series covers the entire set of isoaccepting codon triplets.

The series was transfected into a single cell line, and expression levels measured by flow cytometry (see TABLE 4). Overall, the expression level of the reporter gene constructs in the cell line varied over a range of 20-fold, according to the triplet used in the reporter construct. Repeated determinations on the same construct showed excellent inter-assay reproducibility ($r^2=0.9$). Variation in expression levels across the isoaccepting codons for a single amino acid ranged from 1.4-fold for valine to 13-fold for threonine, with a median of about 4-fold. Variation in expression between amino acids was of the same order of magnitude. The order of magnitude of the effect is defined as an average of 4 fold per amino acid if 5 copies are incorporated, compatible with an extreme in range of expression levels of up to $(1.6)^{200}=10^{86}$ over an average 200-amino acid residues protein. This figure is derived as:

$[1+((4-1) ( \text{range of reporter construct expression})/5 (\text{no of triplets in the reporter construct}))]^{200 (\text{no of amino acid residues in the protein})}$ and is more than sufficient to explain the observed differences in expression of mammalian genes according to codon usage.

The results presented in TABLE 4 also show that various codons in the undifferentiated epithelial cells (COS-1) have translational efficiencies at least two-fold higher or two-fold lower relative to those of their corresponding synonymous codons. Representative codons having at least a two-fold higher translational efficiency relative to at least one of their corresponding synonymous codons include aga (Arg), cgg (Arg), tgc (Cys), gga (Gly), ggc (Gly), ccg (Pro), cga (Pro), aca (Thr), acg (Thr), and act (Thr). Thus, these codons appear to be preferred for translation in the undifferentiated epithelial cells. By contrast, representative codons having at least a two-fold lower translational efficiency relative to at least one of their corresponding synonymous codons include agg (Arg), tgt (Cys), ggg (Gly), ggt (Gly), ccc (Pro), cct (Pro), and acc (Thr) These latter codons would therefore appear to be less preferred for translation in the undifferentiated epithelial cells. Accordingly, if higher protein expression is required within undifferentiated epithelial cells such as COS-1 cells, the preferred codons should be used to replace any existing codons of a parent polynucleotide encoding the protein that correspond to the less preferred codons. In this respect, a codon substitution algorithm for increasing protein expression in non-differentiated epithelial cells is presented in TABLE 5. However, if lower protein expression is required in non-differentiated epithelial cells, the less preferred codons should be used to replace any existing codons of the parent polynucleotide that correspond to the preferred codons.

The disclosure of every patent, patent application, and publication cited herein is hereby incorporated by reference in its entirety.

The present invention has been described in terms of particular embodiments found or proposed by the present inventors to comprise preferred modes for the practice of the invention. Those of skill in the art will appreciate that, in light of the present disclosure, numerous modifications and changes can be made in the particular embodiments exemplified without departing from the scope of the invention. All such modifications are intended to be included within the scope of the appended claims.

Table Legends

TABLE 1

The codon usage data for human, cow, yeast and wheat proteins are derived from published results (Wada, K. et al, 1992, Nucleic Acids Res 20 Suppl: 2111–2118; 1991, Nucleic Acids Res 19 Suppl: 1981–1986; 1990, Nucleic Acids Res 18 Suppl: 2367–411), which are incorporated herein by reference. The BPV1 data are from sequences in the GenBank database.

TABLE 2

Each iso-acceptor tRNA with anticodon shown as superscript is shown on top row. The letter "x" indicates an arbitrary value for the relative abundance of tRNA between differentiated ("superficial" layer of the epidermis) and undifferentiated ("basal" layer of the epidermis) cell layers, wherein "10x" and "100x" indicates about a ten-fold and about a one hundred-fold difference, respectively, in abundance of iso-tRNA between these layers.

TABLE 3

Synthetic gfp constructs are tabulated by SEQ ID NO and by the codon corresponding to the tandem repeat of five identical codons immediately upstream of the gfp gene.

TABLE 4

Mean fluorescence intensities of up to four different samples of transiently transfected COS-1 cells are shown (Green mean 1–4). Synthetic gfp constructs are tabulated by SEQ ID NO and by the codon corresponding to the tandem repeat immediately upstream of the gfp gene.

TABLE 5

Input codons and output codons represent, respectively, synonymous codons and existing (i.e. "first") codons according to the invention. Change means an actual change of a codon.

Tables

TABLE 1

Frequency (per one thousand) of codon usage for individual organisms.

| Amino acids | Codons | Human | Cow | Yeast | Wheat | BPVL1/L2 |
|---|---|---|---|---|---|---|
| ARG | CGA | 5.4 | 5.5 | 2.3 | 2.3 | 7.2 |
|  | CGC | 11.3 | 12.2 | 2.0 | 7.5 | 4.1 |
|  | CGG | 10.4 | 11.2 | 1.1 | 4.6 | 5.1 |
|  | CGU | 4.7 | 3.7 | 7.5 | 1.1 | 10.4 |

TABLE 1-continued

Frequency (per one thousand) of codon usage for individual organisms.

| Amino acids | Codons | Human | Cow | Yeast | Wheat | BPVL1/L2 |
|---|---|---|---|---|---|---|
|  | AGA | 9.9 | 9.9 | 24.0 | 4.1 | 14.4 |
|  | AGG | 11.1 | 11.4 | 7.5 | 7.1 | 9.3 |
| LEU | CUA | 6.2 | 4.9 | 11.8 | 12.1 | 18.6 |
|  | CUC | 19.9 | 21.2 | 4.1 | 18.6 | 6.2 |
|  | CUG | 42.5 | 46.6 | 8.3 | 15.5 | 15.5 |
|  | CUU | 10.7 | 10.6 | 9.6 | 6.5 | 20.7 |
|  | UUA | 5.3 | 4.0 | 24.5 | 1.8 | 14.5 |
|  | UUG | 11.0 | 9.6 | 32.1 | 15.3 | 15.5 |
| SER | UCA | 9.3 | 7.6 | 15.6 | 14.6 | 16.6 |
|  | UCC | 17.7 | 17.6 | 14.4 | 10.1 | 11.4 |
|  | UCG | 4.2 | 4.5 | 6.5 | 9.6 | 6.2 |
|  | UCU | 13.2 | 11.2 | 24.6 | 14.8 | 15.5 |
|  | AGC | 18.7 | 18.7 | 7.1 | 12.8 | 12.4 |
|  | AGU | 9.4 | 8.6 | 11.7 | 12.9 | 21.7 |
| THR | ACA | 14.4 | 11.4 | 15.6 | 4.6 | 37.3 |
|  | ACC | 23.0 | 21.1 | 13.9 | 15.9 | 19.7 |
|  | ACG | 6.7 | 7.8 | 6.7 | 4.5 | 4.1 |
|  | ACU | 12.7 | 9.6 | 22.0 | 11.8 | 28.0 |
| PRO | CCA | 14.6 | 12.0 | 21.4 | 71.2 | 22.8 |
|  | CCC | 20.0 | 19.2 | 5.9 | 11.1 | 15.5 |
|  | CCG | 6.5 | 7.9 | 4.1 | 19.4 | 0.0 |
|  | CCU | 15.5 | 14.6 | 12.8 | 10.3 | 33.1 |
| ALA | GCA | 14.0 | 13.1 | 15.3 | 11.2 | 33.1 |
|  | GCC | 29.1 | 35.8 | 15.5 | 19.5 | 17.6 |
|  | GCG | 7.2 | 9.3 | 5.1 | 13.8 | 4.1 |
|  | GCU | 19.6 | 19.1 | 28.3 | 9.6 | 13.5 |
| GLY | GGA | 17.1 | 16.2 | 8.9 | 25.9 | 22.8 |
|  | GGC | 25.4 | 28.1 | 8.9 | 28.0 | 12.4 |
|  | GGG | 17.3 | 19.2 | 5.1 | 28.5 | 22.8 |
|  | GGU | 11.2 | 11.8 | 34.9 | 9.6 | 18.6 |
| VAL | GUA | 5.9 | 5.1 | 10.0 | 4.4 | 15.5 |
|  | GUC | 16.3 | 18.4 | 14.9 | 14.8 | 6.2 |
|  | GUG | 30.9 | 32.9 | 9.5 | 12.9 | 23.8 |
|  | GUU | 10.4 | 9.9 | 26.6 | 11.6 | 16.6 |
| LYS | AAA | 22.2 | 21.6 | 37.7 | 4.5 | 37.2 |
|  | AAG | 34.9 | 37.1 | 35.2 | 17.4 | 13.5 |
| ASN | AAC | 22.6 | 22.4 | 25.8 | 14.2 | 10.3 |
|  | AAU | 16.6 | 12.5 | 31.4 | 6.7 | 24.8 |
| GLN | CAA | 11.1 | 9.7 | 29.8 | 171.8 | 22.8 |
|  | CAG | 33.6 | 34.4 | 10.4 | 79.4 | 17.6 |
| HIS | CAC | 14.2 | 14.0 | 8.2 | 8.2 | 6.2 |
|  | CAU | 9.3 | 7.5 | 12.3 | 7.1 | 13.4 |
| GLU | GAA | 26.8 | 24.4 | 48.9 | 7.8 | 36.2 |
|  | GAG | 41.4 | 45.4 | 16.9 | 19.7 | 21.7 |
| ASP | GAC | 29.0 | 31.5 | 22.3 | 13.0 | 18.6 |
|  | GAU | 21.7 | 19.2 | 37.0 | 4.0 | 33.1 |
| TYR | UAC | 18.8 | 20.3 | 16.5 | 24.5 | 17.6 |
|  | UAU | 12.5 | 10.5 | 16.5 | 12.5 | 18.6 |
| CYS | UGC | 14.5 | 13.9 | 3.7 | 14.8 | 5.2 |
|  | UGU | 9.9 | 9.4 | 7.6 | 4.9 | 5.2 |
| PHE | UUC | 22.6 | 25.5 | 20.0 | 14.1 | 7.2 |
|  | UUU | 15.8 | 17.0 | 23.2 | 15.0 | 23.8 |
| ILE | AUA | 5.8 | 5.2 | 12.8 | 5.4 | 22.7 |
|  | AUC | 24.3 | 25.8 | 18.4 | 19.7 | 8.2 |
|  | AUU | 14.9 | 13.1 | 31.1 | 10.7 | 20.7 |

TABLE 3

Synthetic constructs and tandem codon repeats encoded thereby.

| SEQ ID NO | Tandem repeat |
|---|---|
| 35 | Ala (GCA) × 5 |
| 37 | Ala (GCC) × 5 |
| 39 | Ala (GCG) × 5 |
| 41 | Ala (GCT) × 5 |
| 43 | Arg (AGA) × 5 |
| 45 | Arg (AGG) × 5 |
| 47 | Arg (CGA) × 5 |
| 49 | Arg (CGC) × 5 |
| 51 | Arg (CGG) × 5 |
| 53 | Arg (CGT) × 5 |
| 55 | Asn (AAC) × 5 |
| 57 | Asn (AAT) × 5 |
| 59 | Asp (GAC) × 5 |
| 61 | Asp (GAT) × 5 |
| 63 | Cys (TGC) × 5 |
| 65 | Cys (TGT) × 5 |
| 67 | Gln (CAA) × 5 |
| 69 | Gln (CAG) × 5 |
| 71 | Gly (GAA) × 5 |
| 73 | Glu (GAG) × 5 |
| 75 | Gly (GGA) × 5 |
| 77 | Gly (GGC) × 5 |
| 79 | Gly (GGG) × 5 |
| 81 | Gly (GGT) × 5 |
| 83 | His (CAC) × 5 |
| 85 | His (CAT) × 5 |
| 87 | Ile (ATA) × 5 |
| 89 | Ile (ATC) × 5 |
| 91 | Ile (ATT) × 5 |
| 93 | Leu (CTA) × 5 |
| 95 | Leu (CTC) × 5 |
| 97 | Leu (CTG) × 5 |
| 99 | Leu (CTT) × 5 |
| 101 | Leu (TTA) × 5 |
| 103 | Leu (TTG) × 5 |
| 105 | Lys (AAA) × 5 |
| 107 | Lys (AAG) × 5 |
| 109 | Phe (TTT) × 5 |
| 111 | Phe (TTC) × 5 |
| 113 | Pro (CCC) × 5 |
| 115 | Pro (CCG) × 5 |
| 117 | Pro (CCT) × 5 |
| 119 | Pro (CGA) × 5 |
| 121 | Ser (AGC) × 5 |
| 123 | Ser (AGT) × 5 |
| 125 | Ser (TCA) × 5 |
| 127 | Ser (TCC) × 5 |
| 129 | Ser (TCG) × 5 |
| 131 | Ser (TCT) × 5 |
| 133 | Thr (ACA) × 5 |
| 135 | Thr (ACC) × 5 |
| 137 | Thr (ACG) × 5 |
| 139 | Thr (ACT) × 5 |
| 141 | Trp (TGG) × 5 |
| 143 | Tyr (TAT) × 5 |
| 145 | Tyr (TAC) × 5 |
| 147 | Val (GTA) × 5 |

TABLE 2 tRNA population changes as KC starts to differentiate.

| tRNA | $Arg^{CGA}$ | $Ala^{GCA}$ | $His^{CAC}$ | $Leu^{CTT}$ | $Leu^{CTA}$ | $Lys^{AAG}$ | $Lys^{AAA}$ | $Met^{Ini}$ |
|---|---|---|---|---|---|---|---|---|
| Superficial | x | 100x | X | 100x | 100x | 10x | x | x |
| Basal | 100x | x | 10x | x | x | x | x | 10x |

| tRNA | $Pro^{CCI}$ | $Val^{GTA}$ | $Val^{GTI}$ | $His^{CAC}$ | $Asn^{AAC}$ | $Thr^{ACA}$ | $Met^{Elo}$ | $Gly^{GGA}$ |
|---|---|---|---|---|---|---|---|---|
| Superficial | x | 10x | x | 10x | x | x | x | x |
| Basal | 100x | x | x | X | 100x | x | 10x | x |

TABLE 3-continued

Synthetic constructs and tandem codon repeats encoded thereby.

| SEQ ID NO | Tandem repeat |
|---|---|
| 149 | Val (GTC) × 5 |
| 151 | Val (GTG) × 5 |
| 153 | Val (GTT) × 5 |
| 155 | Stop (TAA) × 5 |
| 156 | Stop (TAG) × 5 |
| 157 | Stop (TGA) × 5 |
| 158 | control |

TABLE 4

GFP protein expression in transiently transfected COS-1 cells

| SEQ ID NO | Codon | [DNA] (µg/mL) | Green mean 1 | Green mean 2 | Green mean 3 | Green mean 4 | Average |
|---|---|---|---|---|---|---|---|
| 35 | Ala (GCA) | 1.07 | 45.70 | 54.40 | | | 50.05 |
| 37 | Ala (GCC) | 1.10 | 43.70 | 50.00 | | | 46.85 |
| 39 | Ala (GCG) | 0.03 | 28.50 | 42.40 | | | 35.45 |
| 41 | Ala (GCT) | 0.56 | 11.60 | 48.30 | | | 29.95 |
| 43 | Arg (AGA) | 0.90 | 29.00 | 33.00 | | | 31.00 |
| 45 | Arg (AGG) | 0.34 | 7.35 | 2.88 | | | 5.12 |
| 47 | Arg (CGA) | 1.00 | 18.30 | 14.20 | | | 16.25 |
| 49 | Arg (CGC) | 0.86 | 14.60 | 16.00 | | | 15.30 |
| 51 | Arg (CGG) | 1.00 | 22.50 | 20.60 | | | 21.55 |
| 53 | Arg (CGT) | 0.68 | 21.70 | 32.20 | | | 26.95 |
| 55 | Asn (AAC) | 0.02 | | | | | |
| 57 | Asn (AAT) | 0.38 | 28.30 | 8.22 | | | 18.26 |
| 59 | Asp (GAC) | 0.46 | 24.90 | 17.80 | | | 21.35 |
| 61 | Asp (GAT) | 1.39 | 14.50 | 18.90 | | | 16.70 |
| 63 | Cys (TGC) | 0.68 | 21.90 | 16.10 | | | 19.00 |
| 65 | Cys (TGT) | 1.14 | 5.95 | 5.89 | | | 5.92 |
| 67 | Gln (CAA) | 0.28 | 26.50 | 43.50 | | | 35.00 |
| 69 | Gln (CAG) | 1.98 | 44.70 | 48.60 | | | 46.65 |
| 71 | Glu (GAA) | 0.60 | 10.30 | 22.70 | | | 16.50 |
| 73 | Glu (GAG) | 0.43 | 3.86 | | | | |
| 75 | Gly (GGA) | 0.33 | 28.80 | 36.30 | | | 32.55 |
| 77 | Gly (GGC) | 1.62 | 17.80 | 28.10 | | | 22.95 |
| 79 | Gly (GGG) | 1.15 | 6.43 | 4.96 | | | 5.70 |
| 81 | Gly (GGT) | 1.39 | 7.12 | 4.02 | | | 5.57 |
| 83 | His (CAC) | 1.62 | 29.90 | 39.70 | | | 34.80 |
| 85 | His (CAT) | 1.69 | 43.40 | 37.20 | | | 40.30 |
| 87 | Ile (ATA) | 0.69 | 2.76 | 3.98 | | | 3.37 |
| 89 | Ile (ATC) | 1.52 | 4.12 | 2.83 | | | 3.48 |
| 91 | Ile (ATT) | 1.77 | 3.19 | 3.16 | | | 3.18 |
| 93 | Leu (CTA) | 0.10 | 15.00 | 3.01 | 5.26 | 2.44 | 6.43 |
| 95 | Leu (CTC) | 1.74 | 2.70 | 2.92 | 2.56 | | 2.73 |
| 97 | Leu (CTG) | 0.41 | 2.80 | 7.51 | 2.63 | | 4.31 |
| 99 | Leu (CTT) | 1.43 | 3.17 | 3.56 | 2.70 | | 3.14 |
| 101 | Leu (TTA) | 0.62 | 3.85 | 3.91 | 2.66 | | 3.47 |
| 103 | Leu (TTG) | 0.70 | 2.87 | 4.63 | 2.85 | | 3.45 |
| 105 | Lys (AAA) | 0.10 | 11.90 | 8.24 | | | 10.07 |
| 107 | Lys (AAG) | 0.56 | 19.20 | 16.00 | | | 17.60 |
| 109 | Phe (TTT) | 2.28 | 2.67 | | | | |
| 111 | Phe (TTC) | 1.65 | 4.35 | | | | |
| 113 | Pro (CCC) | 0.40 | 12.00 | 8.95 | | | 10.48 |
| 115 | Pro (CCG) | 0.13 | 17.40 | 25.40 | | | 21.40 |
| 117 | Pro (CCT) | 0.40 | 10.60 | 9.89 | | | 10.25 |
| 119 | Pro (CGA) | 0.17 | 27.20 | 34.80 | | | 31.00 |
| 121 | Ser (AGC) | 0.03 | 62.40 | | | | |
| 123 | Ser (AGT) | 0.81 | 23.10 | | | | |
| 125 | Ser (TCA) | 0.08 | 30.70 | 37.20 | | | 33.95 |
| 127 | Ser (TCC) | 1.68 | 32.90 | | | | |
| 129 | Ser (TCG) | 1.58 | 60.00 | | | | |
| 131 | Ser (TCT) | 0.62 | 26.80 | 40.70 | | | 33.75 |
| 133 | Thr (ACA) | 1.70 | 37.80 | 39.90 | | | 38.85 |

TABLE 4-continued

GFP protein expression in transiently transfected COS-1 cells

| SEQ ID NO | Codon | [DNA] (μg/mL) | Green mean 1 | Green mean 2 | Green mean 3 | Green mean 4 | Average |
|---|---|---|---|---|---|---|---|
| 135 | Thr (ACC) | 7.69 | 3.48 | 2.75 | | | 3.12 |
| 137 | Thr (ACG) | 1.06 | 36.10 | 44.10 | | | 40.10 |
| 139 | Thr (ACT) | 1.42 | 38.80 | 42.60 | | | 40.70 |
| 141 | Trp (TGG) | 1.19 | 5.21 | 4.29 | | | 4.75 |
| 143 | Tyr (TAT) | 0.02 | | | | | |
| 145 | Tyr (TAC) | 1.07 | 12.00 | 15.00 | | | 13.50 |
| 147 | Val (GTA) | 0.16 | 10.50 | 3.81 | | | 7.16 |
| 149 | Val (GTC) | 0.66 | 15.20 | 4.55 | 3.65 | 5.06 | 7.12 |
| 151 | Val (GTG) | 0.10 | 9.17 | 4.29 | 7.03 | 2.36 | 5.71 |
| 153 | Val (GTT) | 0.49 | 14.10 | 2.63 | 3.70 | 2.49 | 5.73 |
| 155 | stop (TAA) | 1.88 | 39.40 | 35.30 | | | 37.35 |
| 156 | stop (TAG) | 2.86 | 2.88 | 3.28 | | | 3.08 |
| 157 | stop (TGA) | 0.02 | | | | | |
| 158 GFP alone control | | 9.34 | 61.60 | 30.40 | 55.00 | | 39.09 |
| | | | 2.33 | 2.21 | 2.16 | 2.00 | 2.18 |

TABLE 5

Substitution algorithm used for high level expression in non-differentiated epithelial cells

| Input Codon | Output Codon | Amino Acid | Change |
|---|---|---|---|
| AAA | AAG | LYS | Yes |
| AAC | AAC | ASN | No |
| AAG | AAG | LYS | No |
| AAT | AAC | ASN | Yes |
| AAU | AAC | ASN | Yes |
| ACA | ACC | THR | Yes |
| ACC | ACC | THR | No |
| ACG | ACC | THR | Yes |
| ACT | ACC | THR | Yes |
| ACU | ACC | THR | Yes |
| AGA | AGG | ARG | Yes |
| AGC | AGC | SER | No |
| AGG | AGG | ARG | No |
| AGT | AGC | SER | Yes |
| AGU | AGC | SER | Yes |
| ATA | ATC | ILE | Yes |
| ATC | ATC | ILE | No |
| ATG | ATG | MET | No |
| ATT | ATC | ILE | Yes |
| AUA | ATC | ILE | Yes |
| AUC | ATC | ILE | No |
| AUG | ATG | MET | No |
| AUU | ATC | ILE | Yes |
| CAA | CAG | GLN | Yes |
| CAC | CAC | HIS | No |
| CAG | CAG | GLN | No |
| CAT | CAC | HIS | Yes |
| CAU | CAC | HIS | Yes |
| CCA | CCC | PRO | Yes |
| CCC | CCC | PRO | No |
| CCG | CCC | PRO | Yes |
| CCT | CCC | PRO | Yes |
| CCU | CCC | PRO | Yes |
| CGA | CGC | ARG | Yes |
| CGC | CGC | ARG | No |
| CGG | CGC | ARG | Yes |
| CGT | CGC | ARG | Yes |
| CGU | CGC | ARG | Yes |
| CTA | CTG | LEU | Yes |
| CTC | CTG | LEU | Yes |
| CTG | CTG | LEU | No |
| CTT | CTG | LEU | Yes |
| CUA | CTG | LEU | Yes |
| CUC | CTG | LEU | Yes |
| CUG | CTG | LEU | No |
| CUU | CTG | LEU | Yes |
| GAA | GAG | GLU | Yes |
| GAC | GAC | ASP | No |
| GAG | GAG | GLU | No |
| GAT | GAC | ASP | Yes |
| GAU | GAC | ASP | Yes |
| GCA | GCC | ALA | Yes |
| GCC | GCC | ALA | No |
| GCG | GCC | ALA | Yes |
| GCT | GCC | ALA | Yes |
| GCU | GCC | ALA | Yes |
| GGA | GGC | GLY | Yes |
| GGC | GGC | GLY | No |
| GGG | GGG | GLY | No |
| GGT | GGC | GLY | Yes |
| GGU | GGC | GLY | Yes |
| GTA | GTG | VAL | Yes |
| GTC | GTG | VAL | Yes |
| GTG | GTG | VAL | No |
| GTT | GTG | VAL | Yes |
| GUA | GTG | VAL | Yes |
| GUC | GTG | VAL | Yes |
| GUG | GTG | VAL | No |
| GUU | GTG | VAL | Yes |
| TAA | TAA | XXX | No |
| TAC | TAC | TYR | No |
| TAG | TAG | XXX | No |
| TAT | TAC | TYR | Yes |
| TCA | TCC | SER | Yes |
| TCC | TCC | SER | No |
| TCG | TCC | SER | Yes |
| TCT | TCC | SER | Yes |
| TGA | TGA | XXX | No |
| TGC | TGC | CYS | No |
| TGG | TGG | TRP | No |
| TGT | TGT | CYS | No |
| TTA | CTG | LEU | Yes |
| TTC | TTC | PHE | No |
| TTG | CTG | LEU | Yes |

TABLE 5-continued

Substitution algorithm used for high level expression in non-differentiated epithelial cells

| Input Codon | Output Codon | Amino Acid | Change |
|---|---|---|---|
| TTT | TTC | PHE | No |
| UAA | TAA | XXX | No |
| UAC | TAC | TYR | No |
| UAG | TAG | XXX | No |
| UAU | TAC | TYR | Yes |
| UCA | TCC | SER | Yes |
| UCC | TCC | SER | No |
| UCG | TCC | SER | Yes |
| UCU | TCC | SER | Yes |
| UGA | TGA | XXX | No |
| UGC | TGC | CYS | No |
| UGG | TGG | TRP | No |
| UGU | TGT | CYS | No |
| UUA | CTG | LEU | Yes |
| UUC | TTC | PHE | No |
| UUG | CTG | LEU | Yes |
| UUU | TTC | PHE | Yes |

What is claimed is:

1. A method of constructing a synthetic polynucleotide encoding a polypeptide, said method comprising:
   selecting a first codon of a parent polynucleotide for replacement with a synonymous codon, wherein said synonymous codon is selected on the basis that it exhibits a higher translational efficiency in a first cell of a mammal than in a second cell of said mammal; and
   replacing said first codon with said synonymous codon to construct said synthetic polynucleotide.

2. The method of claim 1, wherein said first codon and said synonymous codon are selected by:
   comparing translational efficiencies of individual codons in said first cell relative to said second cell; and
   selecting said first codon and said synonymous codon based on said comparison.

3. The method of claim 2, wherein the translational efficiency of an individual codon is measured by:
   introducing into said first cell and into said second cell, a synthetic construct comprising a reporter polynucleotide fused in frame with a tandem repeat of said individual codon, wherein said reporter polynucleotide encodes a reporter protein, and wherein said synthetic construct is operably linked to a regulatory polynucleotide; and
   comparing expression of said reporter protein in said first cell and in said second cell to determine the translational efficiency of said individual codon in said first cell relative to said second cell.

4. The method of claim 3, further comprising:
introducing said synthetic construct into a progenitor cell that is a progenitor of another cell selected from the group consisting of said first cell and said second cell; and
culturing said progenitor cell such that it differentiates to become said other cell, wherein said other cell contains said synthetic construct.

5. The method of claim 3, wherein said synonymous codon is the same as the tandemly repeated codon in a reporter construct from which said reporter protein is expressed in said first cell at a level that is at least 110% the level of said reporter protein that is expressed from the same reporter construct in said second cell.

6. The method of claim 3, wherein said tandem repeat comprises at least three copies of said individual codon.

7. The method of claim 2, wherein the translational efficiency of an individual codon is compared by measuring the abundance of an iso-tRNA corresponding to said individual codon in said first cell relative to said second cell.

8. The method of claim 7, wherein said synonymous codon corresponds to an iso-tRNA which is in higher abundance in said first cell relative to said second cell.

9. The method of claim 7, wherein selecting said first codon and said synonymous codon comprises:
measuring abundance of different iso-tRNAs in said first cell relative to said second cell; and
selecting said first codon and said synonymous codon based on said measurement, wherein said synonymous codon corresponds to an iso-tRNA which is in higher abundance in said first cell than in said second cell.

10. The method of claim 7, wherein said synonymous codon corresponds to an iso-tRNA that is present in said first cell at a level which is at least 110% of the level of the iso-tRNA that is present in said second cell.

11. The method of claim 1, wherein said synonymous codon is selected from the group consisting of (1) a codon used at relatively high frequency by genes of said first cell, (2) a codon used at relatively high frequency by genes of said mammal, (3) a codon used at relatively low frequency by genes of said second cell, and (4) a codon used at relatively low frequency by genes of an organism other than said mammal.

12. The method of claim 1, wherein said first codon is selected from the group consisting of (a) a codon used at relatively high frequency by genes of said second cell, (b) a codon used at relatively low frequency by genes of said first cell, (c) a codon used at relatively low frequency by genes of said mammal, and (d) a codon used at relatively high frequency by genes of an organism other than said mammal.

13. The method of claim 1, wherein said first codon and said synonymous codon are selected such that said protein is expressed from said synthetic polynucleotide in said first cell at a level which is at least 110% of the level at which said protein is expressed from said parent polynucleotide in said first cell.

14. The method of claim 1, wherein said second cell is a precursor cell of said first cell.

15. The method of claim 1, wherein said second cell is a cell derived from said first cell.

16. The method of claim 1, wherein said protein is not substantially expressible in said second cell.

17. The method of claim 1, wherein said first cell is of the same type as said second cell, but is at a different stage of differentiation.

18. The method of claim 1, wherein said first cell is of the same type as said second cell, but is at a different stage of the cell cycle.

19. A method of selectively expressing a protein in a first cell of a mammal, said method comprising:
selecting a first codon of a parent polynucleotide encoding said protein for replacement with a synonymous codon, wherein said synonymous codon is selected on the basis that it exhibits a higher translational efficiency in said first cell than in a second cell of said mammal;
replacing said first codon with said synonymous codon to construct a synthetic polynucleotide; and
introducing said synthetic polynucleotide into a cell selected from the group consisting of said first cell and a precursor of said first cell, said synthetic polynucleotide being operably linked to a regulatory polynucleotide,
whereby said protein is selectively expressed in said first cell.

20. The method of claim 19, wherein said synonymous codon has a higher translational efficiency in said first cell than in said second cell.

21. A method of expressing a protein from a first polynucleotide in a cell, said method comprising:
introducing into said cell a second polynucleotide encoding an iso-tRNA, wherein said second polynucleotide is operably linked to a regulatory polynucleotide, and wherein said iso-tRNA is normally in relatively low abundance in said cell in comparison to other iso-tRNAs and corresponds to a codon of said first polynucleotide; and
expressing said second polynucleotide in said cell, whereby said protein is expressed in said cell.

22. A method of producing a virus particle in a cycling animal cell, wherein said virus particle comprises a protein necessary for assembly of said virus particle, and wherein said protein is expressed in said cell from a parent polynucleotide, but not at a level sufficient to permit virus assembly therein, said method comprising:
replacing a first codon of said parent polynucleotide with a synonymous codon to produce a synthetic polynucleotide having enhanced translational kinetics compared to said parent polynucleotide, such that said protein is expressible from said synthetic polynucleotide in said cell at a level sufficient to permit virus assembly therein; and
introducing into said cell said synthetic polynucleotide operably linked to a regulatory polynucleotide,
whereby said protein is expressed and said virus particle is produced in said cell.

23. The method of claim 22, wherein said synonymous codon has a higher translational efficiency in said cell than said first codon.

24. A method of producing a virus particle in a cycling cell, wherein said virus particle comprises at least one protein necessary for assembly of said virus particle, wherein said protein is expressed in said cell from a first polynucleotide, but not at a level sufficient to permit virus assembly therein, and wherein the abundance of an iso-tRNA specific for a codon of said first polynucleotide limits the rate of production of said protein, said method comprising:
introducing into said cell a second polynucleotide encoding said iso-tRNA; and
expressing said second polynucleotide in said cell,
whereby said virus particle is produced in said cycling cell.

25. A method of expressing a protein from a first polynucleotide in a cell, said method comprising
introducing into a precursor of said cell a second polynucleotide encoding an iso-tRNA, wherein said second polynucleotide is operably linked to a regulatory polynucleotide, and wherein said iso-tRNA is normally in relatively low abundance in said cell in comparison to other iso-tRNAs and corresponds to a codon of said first polynucleotide, wherein said precursor is exposed to conditions sufficient to produce said cell; and
expressing said second polynucleotide in said cell,
whereby said protein is expressed from said first polynucleotide in said cell.

26. A method of producing a virus particle in a cycling eukaryotic cell, wherein said virus particle comprises a protein necessary for assembly of said virus particle, and wherein said protein is expressed in said cell from a parent polynucleotide, but not at a level sufficient to permit virus assembly therein, said method comprising:
replacing a first codon of said parent polynucleotide with a synonymous codon to produce a synthetic polynucleotide having increased translational kinetics compared to said parent polynucleotide, such that said protein is expressible from said synthetic polynucleotide in said cell at a level sufficient to permit virus assembly therein;
introducing into a precursor of said cell said synthetic polynucleotide operably linked to a regulatory polynucleotide; and
exposing said precursor to conditions sufficient to produce said cell, wherein said cell comprises said protein necessary for assembly of said virus particle,
whereby said protein is expressed and said virus particle is produced in said cell.

27. A method of constructing a synthetic polynucleotide encoding a protein, said method comprising:
selecting a first codon of a parent polynucleotide for replacement with a synonymous codon, wherein said synonymous codon is selected on the basis that it exhibits a lower translational efficiency in a first cell of a mammal than in a second cell of said mammal; and
replacing said first codon with said synonymous codon to construct said synthetic polynucleotide.

28. The method of claim 27, wherein said first codon and said synonymous codon are selected by:
comparing translational efficiencies of individual codons in said first cell relative to said second cell; and
selecting said first codon and said synonymous codon based on said comparison.

29. The method of claim 28, wherein the translational efficiency of an individual codon is measured by:
introducing into said first cell and into said second cell, a synthetic construct comprising a reporter polynucleotide fused in frame with a tandem repeat of said individual codon, wherein said reporter polynucleotide encodes a reporter protein, and wherein said synthetic construct is operably linked to a regulatory polynucleotide; and
comparing expression of said reporter protein in said first cell and in said second cell to determine the translational efficiency of said individual codon in said first cell relative to said second cell.

30. The method of claim 29, further comprising:
introducing said synthetic construct into a progenitor cell that is a progenitor of another cell selected from the group consisting of said first cell and said second cell; and
culturing said progenitor cell such that it differentiates to become said other cell, wherein said other cell contains said synthetic construct.

31. The method of claim 29, wherein said synonymous codon is the same as the tandemly repeated codon in a reporter construct from which said reporter protein is expressed in said second cell at a level that is at least 110% the level of said reporter protein that is expressed from the same reporter construct in said first cell.

32. The method of claim 29, wherein said tandem repeat comprises at least three copies of said individual codon.

33. The method of claim 28, wherein the translational efficiency of an individual codon is compared by measuring the abundance of an iso-tRNA corresponding to said individual codon in said first cell relative to said second cell.

34. The method of claim 33, wherein said synonymous codon corresponds to an iso-tRNA which is in lower abundance in said first cell relative to said second cell.

35. The method of claim 33, wherein selecting said first codon and said synonymous codon comprises:
measuring abundance of different iso-tRNAs in said first cell relative to said second cell; and
selecting said first codon and said synonymous codon based on said measurement, wherein said synonymous codon corresponds to an iso-tRNA which is in lower abundance in said first cell than in said second cell.

36. The method of claim 33, wherein said synonymous codon corresponds to an iso-tRNA that is present in said second cell at a level which is at least 110% of the level of the iso-tRNA that is present in said first cell.

37. The method of claim 27, wherein said synonymous codon is selected from the group consisting of (1) a codon used at relatively high frequency by genes of said second cell, (2) a codon used at relatively low frequency by genes of said mammal, (3) a codon used at relatively low frequency by genes of said first cell, and (4) a codon used at relatively high frequency by genes of an organism other than said mammal.

38. The method of claim 27, wherein said first codon is selected from the group consisting of (a) a codon used at relatively high frequency by genes of said first cell, (b) a codon used at relatively low frequency by genes of said second cell, (c) a codon used at relatively high frequency by genes of said mammal, and (d) a codon used at relatively low frequency by genes of an organism other than said mammal.

39. The method of claim 27, wherein said first codon and said synonymous codon are selected such that said protein is expressed from said parent polynucleotide in said first cell at a level which is at least 110% of the level at which said protein is expressed from said synthetic polynucleotide in said first cell.

40. The method of claim 27, wherein said second cell is a precursor cell of said first cell.

41. The method of claim 27, wherein said second cell is a cell derived from said first cell.

42. The method of claim 27, wherein said protein is not substantially expressible in said first cell.

43. The method of claim 27, wherein said first cell is of the same type as said second cell, but is at a different stage of differentiation.

44. The method of claim 27, wherein said first cell is of the same type as said second cell, but is at a different stage of the cell cycle.

45. A method of constructing a synthetic polynucleotide encoding a protein, said method comprising:
providing a comparison of translational efficiencies of individual codons in a cell of a mammal;

selecting from said comparison a first codon of said parent polynucleotide for replacement with a synonymous codon, wherein said synonymous codon is selected on the basis that it exhibits a higher translational efficiency in said cell than said first codon; and replacing said first codon with said synonymous codon to construct said synthetic polynucleotide.

46. The method of claim 45, wherein said synonymous codon corresponds to an iso-tRNA which is in higher abundance in said cell relative to the iso-tRNA corresponding to said first codon.

47. The method of claim 46, wherein said synonymous codon corresponds to an iso-tRNA that is present in said cell at a level which is at least 110% of the level of an iso-tRNA that corresponds to said first codon.

48. The method of claim 45, wherein said first codon and said synonymous codon are selected such that said protein is expressed from said synthetic polynucleotide in said cell at a level which is at least 110% of the level at which said protein is expressed from said parent polynucleotide in said cell.

49. The method of claim 45, wherein said comparison is provided by comparing translational efficiencies of individual codons in said cell.

50. The method of claim 49, wherein said translational efficiencies are compared by measuring abundance of different iso-tRNAs in said cell.

51. A method of constructing a synthetic polynucleotide encoding a protein, said method comprising:

providing a comparison of translational efficiencies of individual codons in a cell of a mammal;

selecting from said comparison a first codon of said parent polynucleotide for replacement with a synonymous codon, wherein said synonymous codon is selected on the basis that it exhibits a lower translational efficiency in said cell than said first codon; and replacing said first codon with said synonymous codon to construct said synthetic polynucleotide.

52. The method of claim 51, wherein said synonymous codon corresponds to an iso-tRNA which is in lower abundance in said cell relative to the iso-tRNA corresponding to said first codon.

53. The method of claim 51, wherein said comparison is provided by comparing translational efficiencies of individual codons in said cell.

54. The method of claim 53, wherein said translational efficiencies are compared by measuring abundance of different iso-tRNAs in said cell.

55. A method of expressing a protein in a mammalian cell, said method comprising:

comparing translational efficiencies of individual codons in cells of the same type and species as said mammalian cell;

selecting a first codon of a parent polynucleotide encoding said protein for replacement with a synonymous codon, wherein said synonymous codon is selected on the basis that it exhibits a higher translational efficiency in said cells than said first codon;

replacing said first codon with said synonymous codon to form a synthetic polynucleotide;

introducing said synthetic polynucleotide into said cell; and expressing said synthetic polynucleotide in said cell, whereby said protein is expressed from said synthetic polynucleotide in said cell at a higher level than from said parent polynucleotide.

56. The method of claim 55, wherein said synonymous codon corresponds to an iso-tRNA which is in higher abundance in said cells relative to the iso-tRNA corresponding to said first codon.

57. The method of claim 56, wherein said synonymous codon corresponds to an iso-tRNA that is present in said cells at a level which is at least 110% of the level of an iso-tRNA that corresponds to said first codon.

58. The method of claim 55, wherein said first codon and said synonymous codon are selected such that said protein is expressed from said synthetic polynucleotide in said cell at a level which is at least 110% of the level at which said protein is expressed from said parent polynucleotide in said cell.

59. The method of claim 55, wherein said translational efficiencies are compared by assessing the translational efficiency of individual synthetic constructs in said cells, wherein each synthetic construct comprises a reporter polynucleotide fused in frame with a tandem repeat of an individual codon, wherein said reporter polynucleotide encodes a reporter protein, and wherein said synthetic construct is operably linked to a regulatory polynucleotide.

60. The method of claim 55, wherein said translational efficiencies are compared by measuring abundance of different iso-tRNAs in said cells.

* * * * *

UNITED STATES PATENT AND TRADEMARK OFFICE
CERTIFICATE OF CORRECTION

PATENT NO. : 6,489,141 B1 Page 1 of 1
DATED : December 3, 2002
INVENTOR(S) : Ian Hector Frazer et al.

It is certified that error appears in the above-identified patent and that said Letters Patent is hereby corrected as shown below:

<u>Title page,</u>
Item [30], Foreign Application Priority Data, please correct the priority application numbers to read as follows:

-- Jul. 9, 1997    (AU)   PO7765/97
   Sep. 11, 1997   (AU)   PO9467/97
   Jan. 8, 1999    (AU)   PP8078/99 --

Signed and Sealed this

Second Day of March, 2004

JON W. DUDAS
*Acting Director of the United States Patent and Trademark Office*

SEQUENCE LISTING

<160> NUMBER OF SEQ ID NOS: 219

<210> SEQ ID NO 1
<211> LENGTH: 1488
<212> TYPE: DNA
<213> ORGANISM: Bovine papillomavirus type 1
<220> FEATURE:
<221> NAME/KEY: CDS
<222> LOCATION: (1)..(1488)
<220> FEATURE:
<223> OTHER INFORMATION: L1 open reading frame (wild-type)

<400> SEQUENCE: 1

```
atg gcg ttg tgg caa caa ggc cag aag ctg tat ctc cct cca acc cct      48
Met Ala Leu Trp Gln Gln Gly Gln Lys Leu Tyr Leu Pro Pro Thr Pro
  1               5                  10                  15 gta agc aag gtg ctt tgc agt gaa acc tat gtg caa aga aaa agc att      96
Val Ser Lys Val Leu Cys Ser Glu Thr Tyr Val Gln Arg Lys Ser Ile
             20                  25                  30 ttt tat cat gca gaa acg gag cgc ctg cta act ata gga cat cca tat     144
Phe Tyr His Ala Glu Thr Glu Arg Leu Leu Thr Ile Gly His Pro Tyr
         35                  40                  45 tac cca gtg tct atc ggg gcc aaa act gtt cct aag gtc tct gca aat     192
Tyr Pro Val Ser Ile Gly Ala Lys Thr Val Pro Lys Val Ser Ala Asn
     50                  55                  60 cag tat agg gta ttt aaa ata caa cta cct gat ccc aat caa ttt gca     240
Gln Tyr Arg Val Phe Lys Ile Gln Leu Pro Asp Pro Asn Gln Phe Ala
 65                  70                  75                  80 cta cct gac agg act gtt cac aac cca agt aaa gag cgg ctg gtg tgg     288
```

```
Leu Pro Asp Arg Thr Val His Asn Pro Ser Lys Glu Arg Leu Val Trp
             85                  90                  95 cca gtc ata ggt gtg cag gtg tcc aga ggg cag cct ctt gga ggt act         336
Pro Val Ile Gly Val Gln Val Ser Arg Gly Gln Pro Leu Gly Gly Thr
            100                 105                 110 gta act ggg cac ccc act ttt aat gct ttg ctt gat gca gaa aat gtg         384
Val Thr Gly His Pro Thr Phe Asn Ala Leu Leu Asp Ala Glu Asn Val
            115                 120                 125 aat aga aaa gtc acc acc caa aca aca gat gac agg aaa caa aca ggc         432
Asn Arg Lys Val Thr Thr Gln Thr Thr Asp Asp Arg Lys Gln Thr Gly
            130                 135                 140 cta gat gct aag caa caa cag att ctg ttg cta ggc tgt acc cct gct         480
Leu Asp Ala Lys Gln Gln Gln Ile Leu Leu Leu Gly Cys Thr Pro Ala
145                 150                 155                 160 gaa ggg gaa tat tgg aca aca gcc cgt cca tgt gtt act gat cgt cta         528
Glu Gly Glu Tyr Trp Thr Thr Ala Arg Pro Cys Val Thr Asp Arg Leu
                165                 170                 175 gaa aat ggc gcc tgc cct cct ctt gaa tta aaa aac aag cac ata gaa         576
Glu Asn Gly Ala Cys Pro Pro Leu Glu Leu Lys Asn Lys His Ile Glu
            180                 185                 190 gat ggg gat atg atg gaa att ggg ttt ggt gca gcc aac ttc aaa gaa         624
Asp Gly Asp Met Met Glu Ile Gly Phe Gly Ala Ala Asn Phe Lys Glu
            195                 200                 205 att aat gca agt aaa tca gat cta cct ctt gac att caa aat gag atc         672
Ile Asn Ala Ser Lys Ser Asp Leu Pro Leu Asp Ile Gln Asn Glu Ile
            210                 215                 220 tgc ttg tac cca gac tac ctc aaa atg gct gag gac gct gct ggt aat         720
Cys Leu Tyr Pro Asp Tyr Leu Lys Met Ala Glu Asp Ala Ala Gly Asn
225                 230                 235                 240 agc atg ttc ttt ttt gca agg aaa gaa cag gtg tat gtt aga cac atc         768
Ser Met Phe Phe Phe Ala Arg Lys Glu Gln Val Tyr Val Arg His Ile
                245                 250                 255 tgg acc aga ggg ggc tcg gag aaa gaa gcc cct acc aca gat ttt tat         816
Trp Thr Arg Gly Gly Ser Glu Lys Glu Ala Pro Thr Thr Asp Phe Tyr
            260                 265                 270 tta aag aat aat aaa ggg gat gcc acc ctt aaa ata ccc agt gtg cat         864
Leu Lys Asn Asn Lys Gly Asp Ala Thr Leu Lys Ile Pro Ser Val His
            275                 280                 285 ttt ggt agt ccc agt ggc tca cta gtc tca act gat aat caa att ttt         912
Phe Gly Ser Pro Ser Gly Ser Leu Val Ser Thr Asp Asn Gln Ile Phe
            290                 295                 300 aat cgg ccc tac tgg cta ttc cgt gcc cag ggc atg aac aat gga att         960
Asn Arg Pro Tyr Trp Leu Phe Arg Ala Gln Gly Met Asn Asn Gly Ile
305                 310                 315                 320 gca tgg aat aat tta ttg ttt tta aca gtg ggg gac aat aca cgt ggt        1008
Ala Trp Asn Asn Leu Leu Phe Leu Thr Val Gly Asp Asn Thr Arg Gly
                325                 330                 335 act aat ctt acc ata agt gta gcc tca gat gga acc cca cta aca gag        1056
Thr Asn Leu Thr Ile Ser Val Ala Ser Asp Gly Thr Pro Leu Thr Glu
            340                 345                 350 tat gat agc tca aaa ttc aat gta tac cat aga cat atg gaa gaa tat        1104
Tyr Asp Ser Ser Lys Phe Asn Val Tyr His Arg His Met Glu Glu Tyr
            355                 360                 365 aag cta gcc ttt ata tta gag cta tgc tct gtg gaa atc aca gct caa        1152
Lys Leu Ala Phe Ile Leu Glu Leu Cys Ser Val Glu Ile Thr Ala Gln
            370                 375                 380 act gtg tca cat ctg caa gga ctt atg ccc tct gtg ctt gaa aat tgg        1200
Thr Val Ser His Leu Gln Gly Leu Met Pro Ser Val Leu Glu Asn Trp
385                 390                 395                 400
```

-continued

```
gaa ata ggt gtg cag cct cct acc tca tcg ata tta gag gac acc tat    1248
Glu Ile Gly Val Gln Pro Pro Thr Ser Ser Ile Leu Glu Asp Thr Tyr
            405                 410                 415 cgc tat ata gag tct cct gca act aaa tgt gca agc aat gta att cct    1296
Arg Tyr Ile Glu Ser Pro Ala Thr Lys Cys Ala Ser Asn Val Ile Pro
            420                 425                 430 gca aaa gaa gac cct tat gca ggg ttt aag ttt tgg aac ata gat ctt    1344
Ala Lys Glu Asp Pro Tyr Ala Gly Phe Lys Phe Trp Asn Ile Asp Leu
            435                 440                 445 aaa gaa aag ctt tct ttg gac tta gat caa ttt ccc ttg gga aga aga    1392
Lys Glu Lys Leu Ser Leu Asp Leu Asp Gln Phe Pro Leu Gly Arg Arg
    450                 455                 460 ttt tta gca cag caa ggg gca gga tgt tca act gtg aga aaa cga aga    1440
Phe Leu Ala Gln Gln Gly Ala Gly Cys Ser Thr Val Arg Lys Arg Arg
465                 470                 475                 480 att agc caa aaa act tcc agt aag cct gca aaa aaa aaa aaa aaa taa    1488
Ile Ser Gln Lys Thr Ser Ser Lys Pro Ala Lys Lys Lys Lys Lys
                485                 490                 495

<210> SEQ ID NO 2
<211> LENGTH: 495
<212> TYPE: PRT
<213> ORGANISM: Bovine papillomavirus type 1
<220> FEATURE:
<223> OTHER INFORMATION: L1 open reading frame (wild-type)

<400> SEQUENCE: 2

Met Ala Leu Trp Gln Gln Gly Gln Lys Leu Tyr Leu Pro Pro Thr Pro
 1               5                  10                  15

Val Ser Lys Val Leu Cys Ser Glu Thr Tyr Val Gln Arg Lys Ser Ile
                20                  25                  30

Phe Tyr His Ala Glu Thr Glu Arg Leu Leu Thr Ile Gly His Pro Tyr
            35                  40                  45

Tyr Pro Val Ser Ile Gly Ala Lys Thr Val Pro Lys Val Ser Ala Asn
        50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Pro Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
        195                 200                 205

Ile Asn Ala Ser Lys Ser Asp Leu Pro Leu Asp Ile Gln Asn Glu Ile
210                 215                 220

Cys Leu Tyr Pro Asp Tyr Leu Lys Met Ala Glu Asp Ala Ala Gly Asn
225                 230                 235                 240
```

```
Ser Met Phe Phe Phe Ala Arg Lys Glu Gln Val Tyr Val Arg His Ile
            245                 250                 255

Trp Thr Arg Gly Gly Ser Glu Lys Glu Ala Pro Thr Thr Asp Phe Tyr
            260                 265                 270

Leu Lys Asn Asn Lys Gly Asp Ala Thr Leu Lys Ile Pro Ser Val His
            275                 280                 285

Phe Gly Ser Pro Ser Gly Ser Leu Val Ser Thr Asp Asn Gln Ile Phe
            290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
            325                 330                 335

Thr Asn Leu Thr Ile Ser Val Ala Ser Asp Gly Thr Pro Leu Thr Glu
            340                 345                 350

Tyr Asp Ser Ser Lys Phe Asn Val Tyr His Arg His Met Glu Glu Tyr
            355                 360                 365

Lys Leu Ala Phe Ile Leu Glu Leu Cys Ser Val Glu Ile Thr Ala Gln
            370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Glu Asp Thr Tyr
            405                 410                 415

Arg Tyr Ile Glu Ser Pro Ala Thr Lys Cys Ala Ser Asn Val Ile Pro
            420                 425                 430

Ala Lys Glu Asp Pro Tyr Ala Gly Phe Lys Phe Trp Asn Ile Asp Leu
            435                 440                 445

Lys Glu Lys Leu Ser Leu Asp Leu Asp Gln Phe Pro Leu Gly Arg Arg
            450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
            485                 490                 495
```

<210> SEQ ID NO 3
<211> LENGTH: 1488
<212> TYPE: DNA
<213> ORGANISM: Artificial Sequence
<220> FEATURE:
<221> NAME/KEY: CDS
<222> LOCATION: (1)..(1488)
<220> FEATURE:
<223> OTHER INFORMATION: Description of Artificial Sequence: Bovine
      papillomavirus type 1 L1 open reading frame
      (humanized)
<220> FEATURE:
<223> OTHER INFORMATION: Wild-type codons replaced with synonymous
      codons used at relatively high frequency by human genes

<400> SEQUENCE: 3

```
atg gcc ctg tgg cag cag ggc cag aag ctg tac ctg ccc cct acc ccc        48
Met Ala Leu Trp Gln Gln Gly Gln Lys Leu Tyr Leu Pro Pro Thr Pro
 1               5                  10                  15 gtg agc aag gtg ctt tgc agt gaa acc tat gtg caa aga aaa agc att        96
Val Ser Lys Val Leu Cys Ser Glu Thr Tyr Val Gln Arg Lys Ser Ile
             20                  25                  30 ttt tat cat gca gaa acg gag cgc ctg ctg acc atc gga cac ccc tat       144
Phe Tyr His Ala Glu Thr Glu Arg Leu Leu Thr Ile Gly His Pro Tyr
         35                  40                  45 tac ccc gtg tcc atc ggg gcc aag act gtg cct aag gtg tcc gcc aat       192
```

-continued

```
Tyr Pro Val Ser Ile Gly Ala Lys Thr Val Pro Lys Val Ser Ala Asn
 50                  55                  60 cag tat agg gtg ttc aaa atc caa ctg cct gat ccc aat caa ttt gca        240
Gln Tyr Arg Val Phe Lys Ile Gln Leu Pro Asp Pro Asn Gln Phe Ala
 65                  70                  75                  80 ctg cct gac agg acc gtg cac aac ccc agc aaa gag cgg ctg gtg tgg        288
Leu Pro Asp Arg Thr Val His Asn Pro Ser Lys Glu Arg Leu Val Trp
                 85                  90                  95 cca gtg atc ggc gtg cag gtg tcc aga ggc cag cct ctg ggc ggc acc        336
Pro Val Ile Gly Val Gln Val Ser Arg Gly Gln Pro Leu Gly Gly Thr
            100                 105                 110 gtg act ggg cac ccc act ttt aat gct ttg ctt gat gca gaa aat gtg        384
Val Thr Gly His Pro Thr Phe Asn Ala Leu Leu Asp Ala Glu Asn Val
        115                 120                 125 aat aga aaa gtc acc acc cag acc acc gac gac agg aaa cag aca ggc        432
Asn Arg Lys Val Thr Thr Gln Thr Thr Asp Asp Arg Lys Gln Thr Gly
130                 135                 140 ctg gat gcc aag cag cag cag atc ctg ctg ctg ggc tgt acc cct gct        480
Leu Asp Ala Lys Gln Gln Gln Ile Leu Leu Leu Gly Cys Thr Pro Ala
145                 150                 155                 160 gaa ggg gaa tat tgg aca aca gcc cgt cca tgt gtg acc gac cgt cta        528
Glu Gly Glu Tyr Trp Thr Thr Ala Arg Pro Cys Val Thr Asp Arg Leu
                165                 170                 175 gaa aac ggc gcc tgc cct cct ctg gag ctg aaa aac aag cac atc gaa        576
Glu Asn Gly Ala Cys Pro Pro Leu Glu Leu Lys Asn Lys His Ile Glu
            180                 185                 190 gat ggg gat atg atg gaa att ggg ttt ggt gca gcc aac ttc aaa gaa        624
Asp Gly Asp Met Met Glu Ile Gly Phe Gly Ala Ala Asn Phe Lys Glu
        195                 200                 205 att aat gca agt aaa tca gat cta cct ctg gac atc caa aat gag atc        672
Ile Asn Ala Ser Lys Ser Asp Leu Pro Leu Asp Ile Gln Asn Glu Ile
210                 215                 220 tgc ctg tac ccc gac tac ctg aaa atg gct gag gac gcc gcc ggc aac        720
Cys Leu Tyr Pro Asp Tyr Leu Lys Met Ala Glu Asp Ala Ala Gly Asn
225                 230                 235                 240 agc atg ttc ttc ttc gcc agg aag gag cag gtg tac gtg aga cac atc        768
Ser Met Phe Phe Phe Ala Arg Lys Glu Gln Val Tyr Val Arg His Ile
                245                 250                 255 tgg acc aga ggc ggc tcc gag aaa gaa gcc cct acc aca gat ttt tat        816
Trp Thr Arg Gly Gly Ser Glu Lys Glu Ala Pro Thr Thr Asp Phe Tyr
            260                 265                 270 ttg aag aac aac aag ggc gac gcc acc ctg aag atc ccc agc gtg cac        864
Leu Lys Asn Asn Lys Gly Asp Ala Thr Leu Lys Ile Pro Ser Val His
        275                 280                 285 ttc ggc agc ccc agc ggc tca cta gtg tcc acc gac aac cag atc ttc        912
Phe Gly Ser Pro Ser Gly Ser Leu Val Ser Thr Asp Asn Gln Ile Phe
290                 295                 300 aac cgg ccc tac tgg ctg ttc cgc gcc cag ggc atg aac aat gga att        960
Asn Arg Pro Tyr Trp Leu Phe Arg Ala Gln Gly Met Asn Asn Gly Ile
305                 310                 315                 320 gcc tgg aac aac ctg ctg ttc ctg acc gtg ggc gac aac aca cgt ggc       1008
Ala Trp Asn Asn Leu Leu Phe Leu Thr Val Gly Asp Asn Thr Arg Gly
                325                 330                 335 acc aac ctg acc atc agc gtg gcc tcc gat gga acc cca ctg acc gag       1056
Thr Asn Leu Thr Ile Ser Val Ala Ser Asp Gly Thr Pro Leu Thr Glu
            340                 345                 350 tat gat agc tcg aaa ttc aac gtg tac cac aga cac atg gag gag tat       1104
Tyr Asp Ser Ser Lys Phe Asn Val Tyr His Arg His Met Glu Glu Tyr
        355                 360                 365
```

-continued

```
aag cta gcc ttc atc ctg gag ctg tgc tcc gtg gag atc acc gcc cag    1152
Lys Leu Ala Phe Ile Leu Glu Leu Cys Ser Val Glu Ile Thr Ala Gln
    370                 375                 380 acc gtg tcc cat ctg caa gga ctg atg ccc tcc gtg ctg gag aat tgg    1200
Thr Val Ser His Leu Gln Gly Leu Met Pro Ser Val Leu Glu Asn Trp
385                 390                 395                 400 gag atc ggc gtg cag ccc ccc acc tca tcg atc ttg gag gac acc tac    1248
Glu Ile Gly Val Gln Pro Pro Thr Ser Ser Ile Leu Glu Asp Thr Tyr
                405                 410                 415 cgc tac atc gag tcc ccc gcc acc aag tgt gcc agc aac gtg att cct    1296
Arg Tyr Ile Glu Ser Pro Ala Thr Lys Cys Ala Ser Asn Val Ile Pro
            420                 425                 430 gca aaa gaa gac cct tat gca ggg ttt aag ttc tgg aac atc gac ctg    1344
Ala Lys Glu Asp Pro Tyr Ala Gly Phe Lys Phe Trp Asn Ile Asp Leu
        435                 440                 445 aag gag aag ctg tct ctg gac ctg gat cag ttc ccc ttg ggc aga aga    1392
Lys Glu Lys Leu Ser Leu Asp Leu Asp Gln Phe Pro Leu Gly Arg Arg
    450                 455                 460 ttt ctg gcc cag cag ggg gcc ggc tgt tcc acc gtg aga aaa cgc agg    1440
Phe Leu Ala Gln Gln Gly Ala Gly Cys Ser Thr Val Arg Lys Arg Arg
465                 470                 475                 480 atc agc cag aag acc tcc agc aag ccc gcc aag aag aag aaa aag taa    1488
Ile Ser Gln Lys Thr Ser Ser Lys Pro Ala Lys Lys Lys Lys Lys
                485                 490                 495
```

<210> SEQ ID NO 4
<211> LENGTH: 495
<212> TYPE: PRT
<213> ORGANISM: Artificial Sequence
<220> FEATURE:
<223> OTHER INFORMATION: Description of Artificial Sequence: Bovine
    papillomavirus type 1 L1 open reading frame
    (humanized)
<220> FEATURE:
<223> OTHER INFORMATION: Wild-type codons replaced with synonymous
    codons used at relatively high frequency by human genes

<400> SEQUENCE: 4

```
Met Ala Leu Trp Gln Gln Gly Gln Lys Leu Tyr Leu Pro Pro Thr Pro
 1               5                  10                  15

Val Ser Lys Val Leu Cys Ser Glu Thr Tyr Val Gln Arg Lys Ser Ile
            20                  25                  30

Phe Tyr His Ala Glu Thr Glu Arg Leu Leu Thr Ile Gly His Pro Tyr
        35                  40                  45

Tyr Pro Val Ser Ile Gly Ala Lys Thr Val Pro Lys Val Ser Ala Asn
    50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Pro Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
    130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175
```

```
Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
            195                 200                 205

Ile Asn Ala Ser Lys Ser Asp Leu Pro Leu Asp Ile Gln Asn Glu Ile
            210                 215                 220

Cys Leu Tyr Pro Asp Tyr Leu Lys Met Ala Glu Asp Ala Ala Gly Asn
225                 230                 235                 240

Ser Met Phe Phe Ala Arg Lys Glu Gln Val Tyr Val Arg His Ile
            245                 250                 255

Trp Thr Arg Gly Gly Ser Glu Lys Glu Ala Pro Thr Thr Asp Phe Tyr
            260                 265                 270

Leu Lys Asn Asn Lys Gly Asp Ala Thr Leu Lys Ile Pro Ser Val His
            275                 280                 285

Phe Gly Ser Pro Ser Gly Ser Leu Val Ser Thr Asp Asn Gln Ile Phe
            290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
            325                 330                 335

Thr Asn Leu Thr Ile Ser Val Ala Ser Asp Gly Thr Pro Leu Thr Glu
            340                 345                 350

Tyr Asp Ser Ser Lys Phe Asn Val Tyr His Arg His Met Glu Glu Tyr
            355                 360                 365

Lys Leu Ala Phe Ile Leu Glu Leu Cys Ser Val Glu Ile Thr Ala Gln
            370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Glu Asp Thr Tyr
            405                 410                 415

Arg Tyr Ile Glu Ser Pro Ala Thr Lys Cys Ala Ser Asn Val Ile Pro
            420                 425                 430

Ala Lys Glu Asp Pro Tyr Ala Gly Phe Lys Phe Trp Asn Ile Asp Leu
            435                 440                 445

Lys Glu Lys Leu Ser Leu Asp Leu Asp Gln Phe Pro Leu Gly Arg Arg
            450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
            485                 490                 495
```

<210> SEQ ID NO 5
<211> LENGTH: 1410
<212> TYPE: DNA
<213> ORGANISM: Bovine papillomavirus type 1
<220> FEATURE:
<221> NAME/KEY: CDS
<222> LOCATION: (1)..(1410)
<220> FEATURE:
<223> OTHER INFORMATION: L2 open reading frame (wild-type)

<400> SEQUENCE: 5

```
atg agt gca cga aaa aga gta aaa cgt gcc agt gcc tat gac ctg tac      48
Met Ser Ala Arg Lys Arg Val Lys Arg Ala Ser Ala Tyr Asp Leu Tyr
  1               5                  10                  15 agg acc tgc aag caa gcg ggc aca tgt cca cca gat gtg ata cga aag      96
```

```
Arg Thr Cys Lys Gln Ala Gly Thr Cys Pro Pro Asp Val Ile Arg Lys
         20                  25                  30 gta gaa gga gat act ata gca gat aaa att ttg aaa ttt ggg ggt ctt       144
Val Glu Gly Asp Thr Ile Ala Asp Lys Ile Leu Lys Phe Gly Gly Leu
         35                  40                  45 gca atc tac tta gga ggg cta gga ata gga aca tgg tct act gga agg       192
Ala Ile Tyr Leu Gly Gly Leu Gly Ile Gly Thr Trp Ser Thr Gly Arg
         50                  55                  60 gtg gcc gca ggt gga tca cca agg tac aca cca ctc cga aca gca ggg       240
Val Ala Ala Gly Gly Ser Pro Arg Tyr Thr Pro Leu Arg Thr Ala Gly
65                   70                  75                  80 tcc aca tca tcg ctt gca tca ata gga tcc aga gct gta aca gca ggg       288
Ser Thr Ser Ser Leu Ala Ser Ile Gly Ser Arg Ala Val Thr Ala Gly
                 85                  90                  95 acc cgc ccc agt ata ggt gcg ggc att cct tta gac acc ctt gaa act       336
Thr Arg Pro Ser Ile Gly Ala Gly Ile Pro Leu Asp Thr Leu Glu Thr
                 100                 105                 110 ctt ggg gcc ttg cgt cca ggg gtg tat gag gac act gtg cta cca gag       384
Leu Gly Ala Leu Arg Pro Gly Val Tyr Glu Asp Thr Val Leu Pro Glu
             115                 120                 125 gcc cct gca ata gtc act cct gat gct gtt cct gca gat tca ggg ctt       432
Ala Pro Ala Ile Val Thr Pro Asp Ala Val Pro Ala Asp Ser Gly Leu
         130                 135                 140 gat gcc ctg tcc ata ggt aca gac tcg tcc acg gag acc ctc att act       480
Asp Ala Leu Ser Ile Gly Thr Asp Ser Ser Thr Glu Thr Leu Ile Thr
145                 150                 155                 160 ctg cta gag cct gag ggt ccc gag gac ata gcg gtt ctt gag ctg caa       528
Leu Leu Glu Pro Glu Gly Pro Glu Asp Ile Ala Val Leu Glu Leu Gln
                 165                 170                 175 ccc ctg gac cgt cca act tgg caa gta agc aat gct gtt cat cag tcc       576
Pro Leu Asp Arg Pro Thr Trp Gln Val Ser Asn Ala Val His Gln Ser
             180                 185                 190 tct gca tac cac gcc cct ctg cag ctg caa tcg tcc att gca gaa aca       624
Ser Ala Tyr His Ala Pro Leu Gln Leu Gln Ser Ser Ile Ala Glu Thr
         195                 200                 205 tct ggt tta gaa aat att ttt gta gga ggc tcg ggt tta ggg gat aca       672
Ser Gly Leu Glu Asn Ile Phe Val Gly Gly Ser Gly Leu Gly Asp Thr
         210                 215                 220 gga gga gaa aac att gaa ctg aca tac ttc ggg tcc cca cga aca agc       720
Gly Gly Glu Asn Ile Glu Leu Thr Tyr Phe Gly Ser Pro Arg Thr Ser
225                 230                 235                 240 acg ccc cgc agt att gcc tct aaa tca cgt ggc att tta aac tgg ttc       768
Thr Pro Arg Ser Ile Ala Ser Lys Ser Arg Gly Ile Leu Asn Trp Phe
                 245                 250                 255 agt aaa cgg tac tac aca cag gtg ccc acg gaa gat cct gaa gtg ttt       816
Ser Lys Arg Tyr Tyr Thr Gln Val Pro Thr Glu Asp Pro Glu Val Phe
             260                 265                 270 tca tcc caa aca ttt gca aac cca ctg tat gaa gca gaa cca gct gtg       864
Ser Ser Gln Thr Phe Ala Asn Pro Leu Tyr Glu Ala Glu Pro Ala Val
         275                 280                 285 ctt aag gga cct agt gga cgt gtt gga ctc agt cag gtt tat aaa cct       912
Leu Lys Gly Pro Ser Gly Arg Val Gly Leu Ser Gln Val Tyr Lys Pro
         290                 295                 300 gat aca ctt aca aca cgt agc ggg aca gag gtg gga cca cag cta cat       960
Asp Thr Leu Thr Thr Arg Ser Gly Thr Glu Val Gly Pro Gln Leu His
305                 310                 315                 320 gtc agg tac tca ttg agt act ata cat gaa gat gta gaa gca atc ccc      1008
Val Arg Tyr Ser Leu Ser Thr Ile His Glu Asp Val Glu Ala Ile Pro
                 325                 330                 335
```

-continued

| | | |
|---|---|---|
| tac aca gtt gat gaa aat aca cag gga ctt gca ttc gta ccc ttg cat<br>Tyr Thr Val Asp Glu Asn Thr Gln Gly Leu Ala Phe Val Pro Leu His<br>               340                        345                   350 | 1056 |
| gaa gag caa gca ggt ttt gag gag ata gaa tta gat gat ttt agt gag<br>Glu Glu Gln Ala Gly Phe Glu Glu Ile Glu Leu Asp Asp Phe Ser Glu<br>            355                     360                   365 | 1104 |
| aca cat aga ctg cta cct cag aac acc tct tct aca cct gtt ggt agt<br>Thr His Arg Leu Leu Pro Gln Asn Thr Ser Ser Thr Pro Val Gly Ser<br>370                        375                   380 | 1152 |
| ggt gta cga aga agc ctc att cca act cga gaa ttt agt gca aca cgg<br>Gly Val Arg Arg Ser Leu Ile Pro Thr Arg Glu Phe Ser Ala Thr Arg<br>385                        390                   395                   400 | 1200 |
| cct aca ggt gtt gta acc tat ggc tca cct gac act tac tct gct agc<br>Pro Thr Gly Val Val Thr Tyr Gly Ser Pro Asp Thr Tyr Ser Ala Ser<br>                   405                     410                   415 | 1248 |
| cca gtt act gac cct gat tct acc tct cct agt cta gtt atc gat gac<br>Pro Val Thr Asp Pro Asp Ser Thr Ser Pro Ser Leu Val Ile Asp Asp<br>            420                     425                   430 | 1296 |
| act act act aca cca atc att ata att gat ggg cac aca gtt gat ttg<br>Thr Thr Thr Thr Pro Ile Ile Ile Ile Asp Gly His Thr Val Asp Leu<br>               435                     440                   445 | 1344 |
| tac agc agt aac tac acc ttg cat ccc tcc ttg ttg agg aaa cga aaa<br>Tyr Ser Ser Asn Tyr Thr Leu His Pro Ser Leu Leu Arg Lys Arg Lys<br>450                        455                   460 | 1392 |
| aaa cgg aaa cat gcc taa<br>Lys Arg Lys His Ala<br>465                     470 | 1410 |

<210> SEQ ID NO 6
<211> LENGTH: 469
<212> TYPE: PRT
<213> ORGANISM: Bovine papillomavirus type 1
<220> FEATURE:
<223> OTHER INFORMATION: L2 open reading frame (wild-type)

<400> SEQUENCE: 6

Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Arg Lys
            20                  25                  30

Val Glu Gly Asp Thr Ile Ala Asp Lys Ile Leu Lys Phe Gly Gly Leu
        35                  40                  45

Ala Ile Tyr Leu Gly Gly Leu Gly Ile Gly Thr Trp Ser Thr Gly Arg
    50                  55                  60

Val Ala Ala Gly Gly Ser Pro Arg Tyr Thr Pro Leu Arg Thr Ala Gly
65                  70                  75                  80

Ser Thr Ser Ser Leu Ala Ser Ile Gly Ser Arg Ala Val Thr Ala Gly
                85                  90                  95

Thr Arg Pro Ser Ile Gly Ala Gly Ile Pro Leu Asp Thr Leu Glu Thr
            100                 105                 110

Leu Gly Ala Leu Arg Pro Gly Val Tyr Glu Asp Thr Val Leu Pro Glu
        115                 120                 125

Ala Pro Ala Ile Val Thr Pro Asp Ala Val Pro Ala Asp Ser Gly Leu
    130                 135                 140

Asp Ala Leu Ser Ile Gly Thr Asp Ser Ser Thr Glu Thr Leu Ile Thr
145                 150                 155                 160

Leu Leu Glu Pro Glu Gly Pro Glu Asp Ile Ala Val Leu Glu Leu Gln
                165                 170                 175

-continued

```
Pro Leu Asp Arg Pro Thr Trp Gln Val Ser Asn Ala Val His Gln Ser
            180                 185                 190

Ser Ala Tyr His Ala Pro Leu Gln Leu Gln Ser Ser Ile Ala Glu Thr
            195                 200                 205

Ser Gly Leu Glu Asn Ile Phe Val Gly Gly Ser Gly Leu Gly Asp Thr
            210                 215                 220

Gly Gly Glu Asn Ile Glu Leu Thr Tyr Phe Gly Ser Pro Arg Thr Ser
225                 230                 235                 240

Thr Pro Arg Ser Ile Ala Ser Lys Ser Arg Gly Ile Leu Asn Trp Phe
            245                 250                 255

Ser Lys Arg Tyr Tyr Thr Gln Val Pro Thr Glu Asp Pro Glu Val Phe
            260                 265                 270

Ser Ser Gln Thr Phe Ala Asn Pro Leu Tyr Glu Ala Glu Pro Ala Val
            275                 280                 285

Leu Lys Gly Pro Ser Gly Arg Val Gly Leu Ser Gln Val Tyr Lys Pro
            290                 295                 300

Asp Thr Leu Thr Thr Arg Ser Gly Thr Glu Val Gly Pro Gln Leu His
305                 310                 315                 320

Val Arg Tyr Ser Leu Ser Thr Ile His Glu Asp Val Glu Ala Ile Pro
            325                 330                 335

Tyr Thr Val Asp Glu Asn Thr Gln Gly Leu Ala Phe Val Pro Leu His
            340                 345                 350

Glu Glu Gln Ala Gly Phe Glu Glu Ile Glu Leu Asp Asp Phe Ser Glu
            355                 360                 365

Thr His Arg Leu Leu Pro Gln Asn Thr Ser Ser Thr Pro Val Gly Ser
            370                 375                 380

Gly Val Arg Arg Ser Leu Ile Pro Thr Arg Glu Phe Ser Ala Thr Arg
385                 390                 395                 400

Pro Thr Gly Val Val Thr Tyr Gly Ser Pro Asp Thr Tyr Ser Ala Ser
            405                 410                 415

Pro Val Thr Asp Pro Asp Ser Thr Ser Pro Ser Leu Val Ile Asp Asp
            420                 425                 430

Thr Thr Thr Thr Pro Ile Ile Ile Ile Asp Gly His Thr Val Asp Leu
            435                 440                 445

Tyr Ser Ser Asn Tyr Thr Leu His Pro Ser Leu Leu Arg Lys Arg Lys
            450                 455                 460

Lys Arg Lys His Ala
465
```

<210> SEQ ID NO 7
<211> LENGTH: 1410
<212> TYPE: DNA
<213> ORGANISM: Artificial Sequence
<220> FEATURE:
<221> NAME/KEY: CDS
<222> LOCATION: (1)..(1410)
<220> FEATURE:
<223> OTHER INFORMATION: Description of Artificial Sequence: Bovine
      papillomavirus type 1 L2 open reading frame
      (humanized)
<220> FEATURE:
<223> OTHER INFORMATION: Wild-type codons replaced with synonymous
      codons used at relatively high frequency by human genes

<400> SEQUENCE: 7

```
atg agc gcc cgc aag aga gtg aag cgc gcc agc gcc tac gac ctg tac      48
Met Ser Ala Arg Lys Arg Val Lys Arg Ala Ser Ala Tyr Asp Leu Tyr
 1               5                  10                  15
```

```
                                                                -continued agg acc tgc aag cag gcc ggc aca tgt cca cca gat gtg atc cga aag      96
Arg Thr Cys Lys Gln Ala Gly Thr Cys Pro Pro Asp Val Ile Arg Lys
        20                  25                  30 gtg gag ggc gac acc atc gcc gac aag atc ctg aag ttc ggc ggc ctg     144
Val Glu Gly Asp Thr Ile Ala Asp Lys Ile Leu Lys Phe Gly Gly Leu
    35                  40                  45 gcc atc tac ctg ggc ggc ctg ggc atc gga aca tgg tct acc ggc agg     192
Ala Ile Tyr Leu Gly Gly Leu Gly Ile Gly Thr Trp Ser Thr Gly Arg
50                  55                  60 gtg gcc gcc ggc ggc tca cca agg tac acc cca ctg cgc acc gcc ggc     240
Val Ala Ala Gly Gly Ser Pro Arg Tyr Thr Pro Leu Arg Thr Ala Gly
65                  70                  75                  80 tcc acc tcc tcc ctg gcc tcc atc gga tcc aga gcc gtg acc gcc ggg     288
Ser Thr Ser Ser Leu Ala Ser Ile Gly Ser Arg Ala Val Thr Ala Gly
                85                  90                  95 acc cgc ccc tcc atc ggc gcg ggc atc cct ctg gac acc ctg gaa act     336
Thr Arg Pro Ser Ile Gly Ala Gly Ile Pro Leu Asp Thr Leu Glu Thr
            100                 105                 110 ctt ggg gcc ctg cgc cct ggc gtg tac gag gac acc gtg ctg ccc gaa     384
Leu Gly Ala Leu Arg Pro Gly Val Tyr Glu Asp Thr Val Leu Pro Glu
        115                 120                 125 gcc cct gcc atc gtg acc cct gac gcc gtg cct gca gac tcc ggc ctg     432
Ala Pro Ala Ile Val Thr Pro Asp Ala Val Pro Ala Asp Ser Gly Leu
    130                 135                 140 gac gcc ctg tcc atc ggc aca gac tcc tcc acc gag acc ctg atc acc     480
Asp Ala Leu Ser Ile Gly Thr Asp Ser Ser Thr Glu Thr Leu Ile Thr
145                 150                 155                 160 ctg ctg gag cct gag ggc ccc gaa gac ata gcc gtg ctg gaa ctc cag     528
Leu Leu Glu Pro Glu Gly Pro Glu Asp Ile Ala Val Leu Glu Leu Gln
                165                 170                 175 ccc ctg gac cgc cca acc tgg cag gtg agc aat gct gtg cac cag tcc     576
Pro Leu Asp Arg Pro Thr Trp Gln Val Ser Asn Ala Val His Gln Ser
            180                 185                 190 tct gcc tac cac gcc cct ctc cag ctg caa tcc tcc atc gcc gag aca     624
Ser Ala Tyr His Ala Pro Leu Gln Leu Gln Ser Ser Ile Ala Glu Thr
        195                 200                 205 tct ggt tta gaa aat att ttt gta gga ggc tcg ggt tta ggg gat acc     672
Ser Gly Leu Glu Asn Ile Phe Val Gly Gly Ser Gly Leu Gly Asp Thr
    210                 215                 220 ggc ggc gag aac atc gag ctg acc tac ttc ggc tcc ccc cgc acc agc     720
Gly Gly Glu Asn Ile Glu Leu Thr Tyr Phe Gly Ser Pro Arg Thr Ser
225                 230                 235                 240 acc ccc cgc tcc atc gcc tcc aag tcc cgc ggc atc ctg aac tgg ttc     768
Thr Pro Arg Ser Ile Ala Ser Lys Ser Arg Gly Ile Leu Asn Trp Phe
                245                 250                 255 agc aag cgg tac tac acc cag gtg ccc acc gaa gat ccc gaa gtg ttc     816
Ser Lys Arg Tyr Tyr Thr Gln Val Pro Thr Glu Asp Pro Glu Val Phe
            260                 265                 270 tcc tcc cag acc ttc gcc aac ccc ctg tac gag gcc gag ccc gcc gtg     864
Ser Ser Gln Thr Phe Ala Asn Pro Leu Tyr Glu Ala Glu Pro Ala Val
        275                 280                 285 ctg aag ggc cct agc ggc cgc gtg ggc ctg tcc cag gtg tac aag cct     912
Leu Lys Gly Pro Ser Gly Arg Val Gly Leu Ser Gln Val Tyr Lys Pro
    290                 295                 300 gat acc ctg acc aca cgt agc ggc aca gag gtg ggc ccc cag ctg cat     960
Asp Thr Leu Thr Thr Arg Ser Gly Thr Glu Val Gly Pro Gln Leu His
305                 310                 315                 320 gtg agg tac tcc ctg tcc acc atc cat gag gat gtg gag gct atc ccc    1008
Val Arg Tyr Ser Leu Ser Thr Ile His Glu Asp Val Glu Ala Ile Pro
                325                 330                 335
```

```
tac acc gtg gat gag aac acc cag ggc ctg gcc ttc gtg ccc ctg cat     1056
Tyr Thr Val Asp Glu Asn Thr Gln Gly Leu Ala Phe Val Pro Leu His
            340                 345                 350 gag gag cag gcc ggc ttc gag gag atc gag ctc gac gat ttc agc gag     1104
Glu Glu Gln Ala Gly Phe Glu Glu Ile Glu Leu Asp Asp Phe Ser Glu
        355                 360                 365 acc cat cgc ctg ctg ccc cag aac acc tcc tcc acc ccc gtg ggc agc     1152
Thr His Arg Leu Leu Pro Gln Asn Thr Ser Ser Thr Pro Val Gly Ser
370                 375                 380 ggc gtg cgc aga agc ctg atc cct acc cga gag ttc agc gcc acc cgg     1200
Gly Val Arg Arg Ser Leu Ile Pro Thr Arg Glu Phe Ser Ala Thr Arg
385                 390                 395                 400 cct acc ggc gtg gtg acc tac ggc tcc ccc gac acc tac tcc gct agc     1248
Pro Thr Gly Val Val Thr Tyr Gly Ser Pro Asp Thr Tyr Ser Ala Ser
            405                 410                 415 ccc gtg acc gac cct gat tct acc tct cct agc ctg gtg atc gac gac     1296
Pro Val Thr Asp Pro Asp Ser Thr Ser Pro Ser Leu Val Ile Asp Asp
        420                 425                 430 acc acc acc acc ccc atc atc atc atc gac ggc cac aca gtg gat ctg     1344
Thr Thr Thr Thr Pro Ile Ile Ile Ile Asp Gly His Thr Val Asp Leu
                435                 440                 445 tac agc agc aac tac acc ctg cat ccc tcc ctg ctg agg aag cgc aag     1392
Tyr Ser Ser Asn Tyr Thr Leu His Pro Ser Leu Leu Arg Lys Arg Lys
450                 455                 460 aag cgc aag cat gcc taa                                             1410
Lys Arg Lys His Ala
465                 470

<210> SEQ ID NO 8
<211> LENGTH: 469
<212> TYPE: PRT
<213> ORGANISM: Artificial Sequence
<220> FEATURE:
<223> OTHER INFORMATION: Description of Artificial Sequence: Bovine
      papillomavirus type 1 L2 open reading frame
      (humanized)
<220> FEATURE:
<223> OTHER INFORMATION: Wild-type codons replaced with synonymous
      codons used at relatively high frequency by human genes

<400> SEQUENCE: 8

Met Ser Ala Arg Lys Arg Val Lys Arg Ala Ser Ala Tyr Asp Leu Tyr
  1               5                  10                  15

Arg Thr Cys Lys Gln Ala Gly Thr Cys Pro Pro Asp Val Ile Arg Lys
             20                  25                  30

Val Glu Gly Asp Thr Ile Ala Asp Lys Ile Leu Lys Phe Gly Gly Leu
         35                  40                  45

Ala Ile Tyr Leu Gly Gly Leu Gly Ile Gly Thr Trp Ser Thr Gly Arg
     50                  55                  60

Val Ala Ala Gly Gly Ser Pro Arg Tyr Thr Pro Leu Arg Thr Ala Gly
 65                  70                  75                  80

Ser Thr Ser Ser Leu Ala Ser Ile Gly Ser Arg Ala Val Thr Ala Gly
                 85                  90                  95

Thr Arg Pro Ser Ile Gly Ala Gly Ile Pro Leu Asp Thr Leu Glu Thr
            100                 105                 110

Leu Gly Ala Leu Arg Pro Gly Val Tyr Glu Asp Thr Val Leu Pro Glu
        115                 120                 125

Ala Pro Ala Ile Val Thr Pro Asp Ala Val Pro Ala Asp Ser Gly Leu
    130                 135                 140
```

```
Asp Ala Leu Ser Ile Gly Thr Asp Ser Ser Thr Glu Thr Leu Ile Thr
145                 150                 155                 160

Leu Leu Glu Pro Glu Gly Pro Glu Asp Ile Ala Val Leu Glu Leu Gln
                165                 170                 175

Pro Leu Asp Arg Pro Thr Trp Gln Val Ser Asn Ala Val His Gln Ser
            180                 185                 190

Ser Ala Tyr His Ala Pro Leu Gln Leu Gln Ser Ser Ile Ala Glu Thr
        195                 200                 205

Ser Gly Leu Glu Asn Ile Phe Val Gly Gly Ser Gly Leu Gly Asp Thr
    210                 215                 220

Gly Gly Glu Asn Ile Glu Leu Thr Tyr Phe Gly Ser Pro Arg Thr Ser
225                 230                 235                 240

Thr Pro Arg Ser Ile Ala Ser Lys Ser Arg Gly Ile Leu Asn Trp Phe
                245                 250                 255

Ser Lys Arg Tyr Tyr Thr Gln Val Pro Thr Glu Asp Pro Glu Val Phe
            260                 265                 270

Ser Ser Gln Thr Phe Ala Asn Pro Leu Tyr Glu Ala Glu Pro Ala Val
        275                 280                 285

Leu Lys Gly Pro Ser Gly Arg Val Gly Leu Ser Gln Val Tyr Lys Pro
    290                 295                 300

Asp Thr Leu Thr Thr Arg Ser Gly Thr Glu Val Gly Pro Gln Leu His
305                 310                 315                 320

Val Arg Tyr Ser Leu Ser Thr Ile His Glu Asp Val Glu Ala Ile Pro
                325                 330                 335

Tyr Thr Val Asp Glu Asn Thr Gln Gly Leu Ala Phe Val Pro Leu His
            340                 345                 350

Glu Glu Gln Ala Gly Phe Glu Glu Ile Glu Leu Asp Asp Phe Ser Glu
        355                 360                 365

Thr His Arg Leu Leu Pro Gln Asn Thr Ser Ser Thr Pro Val Gly Ser
    370                 375                 380

Gly Val Arg Arg Ser Leu Ile Pro Thr Arg Glu Phe Ser Ala Thr Arg
385                 390                 395                 400

Pro Thr Gly Val Val Thr Tyr Gly Ser Pro Asp Thr Tyr Ser Ala Ser
                405                 410                 415

Pro Val Thr Asp Pro Asp Ser Ser Pro Ser Leu Val Ile Asp Asp
            420                 425                 430

Thr Thr Thr Thr Pro Ile Ile Ile Ile Asp Gly His Thr Val Asp Leu
    435                 440                 445

Tyr Ser Ser Asn Tyr Thr Leu His Pro Ser Leu Leu Arg Lys Arg Lys
450                 455                 460

Lys Arg Lys His Ala
465

<210> SEQ ID NO 9
<211> LENGTH: 717
<212> TYPE: DNA
<213> ORGANISM: Artificial Sequence
<220> FEATURE:
<223> OTHER INFORMATION: Description of Artificial Sequence: Aequorea
      victoria gfp gene (humanized)
<220> FEATURE:
<221> NAME/KEY: CDS
<222> LOCATION: (1)..(717)

<400> SEQUENCE: 9 atg agc aag ggc gag gaa ctg ttc act ggc gtg gtc cca att ctc gtg      48
Met Ser Lys Gly Glu Glu Leu Phe Thr Gly Val Val Pro Ile Leu Val
```

```
                     1               5                      10                          15
           gaa ctg gat ggc gat gtg aat ggg cac aaa ttt tct gtc agc gga gag         96
           Glu Leu Asp Gly Asp Val Asn Gly His Lys Phe Ser Val Ser Gly Glu
                            20                      25                  30 ggt gaa ggt gat gcc aca tac gga aag ctc acc ctg aaa ttc atc tgc        144
           Gly Glu Gly Asp Ala Thr Tyr Gly Lys Leu Thr Leu Lys Phe Ile Cys
                        35                      40                  45 acc act gga aag ctc cct gtg cca tgg cca aca ctc gtc act acc ttc        192
           Thr Thr Gly Lys Leu Pro Val Pro Trp Pro Thr Leu Val Thr Thr Phe
                    50                      55                  60 tct tat ggc gtg cag tgc ttt tcc aga tac cca gac cat atg aag cag        240
           Ser Tyr Gly Val Gln Cys Phe Ser Arg Tyr Pro Asp His Met Lys Gln
                65                      70                  75                  80 cat gac ttt ttc aag agc gcc atg ccc gag ggc tat gtg cag gag aga        288
           His Asp Phe Phe Lys Ser Ala Met Pro Glu Gly Tyr Val Gln Glu Arg
                            85                      90                  95 acc atc ttt ttc aaa gat gac ggg aac tac aag acc cgc gct gaa gtc        336
           Thr Ile Phe Phe Lys Asp Asp Gly Asn Tyr Lys Thr Arg Ala Glu Val
                        100                     105                 110 aag ttc gaa ggt gac acc ctg gtg aat aga atc gag ctg aag ggc att        384
           Lys Phe Glu Gly Asp Thr Leu Val Asn Arg Ile Glu Leu Lys Gly Ile
                    115                     120                 125 gac ttt aag gag gat gga aac att ctc ggc cac aag ctg gaa tac aac        432
           Asp Phe Lys Glu Asp Gly Asn Ile Leu Gly His Lys Leu Glu Tyr Asn
                130                     135                 140 tat aac tcc cac aat gtg tac atc atg gcc gac aag caa aag aat ggc        480
           Tyr Asn Ser His Asn Val Tyr Ile Met Ala Asp Lys Gln Lys Asn Gly
           145                     150                 155                 160 atc aag gtc aac ttc aag atc aga cac aac att gag gat gga tcc gtg        528
           Ile Lys Val Asn Phe Lys Ile Arg His Asn Ile Glu Asp Gly Ser Val
                            165                     170                 175 cag ctg gcc gac cat tat caa cag aac act cca atc ggc gac ggc cct        576
           Gln Leu Ala Asp His Tyr Gln Gln Asn Thr Pro Ile Gly Asp Gly Pro
                        180                     185                 190 gtg ctc ctc cca gac aac cat tac ctg tcc acc cag tct gcc ctg tct        624
           Val Leu Leu Pro Asp Asn His Tyr Leu Ser Thr Gln Ser Ala Leu Ser
                    195                     200                 205 aaa gat ccc aac gaa aag aga gac cac atg gtc ctg ctg gag ttt gtg        672
           Lys Asp Pro Asn Glu Lys Arg Asp His Met Val Leu Leu Glu Phe Val
                210                     215                 220 acc gct gct ggg atc aca cat ggc atg gac gag ctg tac aag tga            717
           Thr Ala Ala Gly Ile Thr His Gly Met Asp Glu Leu Tyr Lys
           225                     230                 235

<210> SEQ ID NO 10
           <211> LENGTH: 238
           <212> TYPE: PRT
           <213> ORGANISM: Artificial Sequence
           <220> FEATURE:
           <223> OTHER INFORMATION: Description of Artificial Sequence: Aequorea
                 victoria gfp gene (humanized)

<400> SEQUENCE: 10

Met Ser Lys Gly Glu Glu Leu Phe Thr Gly Val Val Pro Ile Leu Val
           1               5                   10                  15

Glu Leu Asp Gly Asp Val Asn Gly His Lys Phe Ser Val Ser Gly Glu
                           20                  25                  30

Gly Glu Gly Asp Ala Thr Tyr Gly Lys Leu Thr Leu Lys Phe Ile Cys
                       35                  40                  45

Thr Thr Gly Lys Leu Pro Val Pro Trp Pro Thr Leu Val Thr Thr Phe
```

```
        50                  55                  60
Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 11
<211> LENGTH: 717
<212> TYPE: DNA
<213> ORGANISM: Artificial Sequence
<220> FEATURE:
<221> NAME/KEY: CDS
<222> LOCATION: (1)..(717)
<220> FEATURE:
<223> OTHER INFORMATION: Description of Artificial Sequence: Synthetic
      gfp gene (Papillomavirusized)
<220> FEATURE:
<223> OTHER INFORMATION: Codons of humanized gfp gene replaced with
      synonymous codons used at relatively high
      frequency by papillomavirus genes

<400> SEQUENCE: 11 atg agt aaa ggg gaa gaa cta ttt aca ggg gtg gtg cct ata cta gtg    48
Met Ser Lys Gly Glu Glu Leu Phe Thr Gly Val Val Pro Ile Leu Val
  1               5                  10                  15 gaa cta gat ggg gat gtg aat ggg cac aaa ttt tct gtc agt ggg gaa    96
Glu Leu Asp Gly Asp Val Asn Gly His Lys Phe Ser Val Ser Gly Glu
             20                  25                  30 ggg gaa ggg gat gca aca tat ggg aaa cta aca cta aaa ttt ata tgc   144
Gly Glu Gly Asp Ala Thr Tyr Gly Lys Leu Thr Leu Lys Phe Ile Cys
         35                  40                  45 aca aca ggg aaa cta cct gtg cca tgg cct aca cta gtg aca aca ttt   192
Thr Thr Gly Lys Leu Pro Val Pro Trp Pro Thr Leu Val Thr Thr Phe
     50                  55                  60 agt tat ggg gtg caa tgc ttt agt aga tat cct gat cat atg aaa caa   240
Ser Tyr Gly Val Gln Cys Phe Ser Arg Tyr Pro Asp His Met Lys Gln
 65                  70                  75                  80 cat gat ttt ttt aaa agt gca atg ccc gag ggg tat gtg caa gaa aga   288
His Asp Phe Phe Lys Ser Ala Met Pro Glu Gly Tyr Val Gln Glu Arg
                 85                  90                  95 aca ata ttt ttt aaa gat gat ggg aat tat aaa aca aga gca gaa gtc   336
Thr Ile Phe Phe Lys Asp Asp Gly Asn Tyr Lys Thr Arg Ala Glu Val
```

-continued

```
aaa ttt gaa ggg gat aca cta gtg aat aga ata gag ctc aaa ggg ata      384
Lys Phe Glu Gly Asp Thr Leu Val Asn Arg Ile Glu Leu Lys Gly Ile
        115                 120                 125 gat ttt aaa gaa gat ggg aat ata cta ggg cat aaa cta gaa tat aat      432
Asp Phe Lys Glu Asp Gly Asn Ile Leu Gly His Lys Leu Glu Tyr Asn
    130                 135                 140 tat aat agt cat aat gtg tat ata atg gca gat aaa caa aaa aat ggg      480
Tyr Asn Ser His Asn Val Tyr Ile Met Ala Asp Lys Gln Lys Asn Gly
145                 150                 155                 160 ata aaa gtg aat ttt aaa ata ata aga cat ata gaa gat gga tcc gtg      528
Ile Lys Val Asn Phe Lys Ile Ile Arg His Ile Glu Asp Gly Ser Val
                165                 170                 175 caa cta gca gat cat tat caa caa aat aca cct ata ggg gat ggg cct      576
Gln Leu Ala Asp His Tyr Gln Gln Asn Thr Pro Ile Gly Asp Gly Pro
            180                 185                 190 gtg cta cta cct gat aac cat tat cta agt aca caa agt gca cta agt      624
Val Leu Leu Pro Asp Asn His Tyr Leu Ser Thr Gln Ser Ala Leu Ser
        195                 200                 205 aaa gat cct aat gaa aaa aga gat cat atg gtg cta ctc gag ttt gtg      672
Lys Asp Pro Asn Glu Lys Arg Asp His Met Val Leu Leu Glu Phe Val
210                 215                 220 aca gca gca ggg ata aca cat ggg atg gat gaa cta tat aaa tga         717
Thr Ala Ala Gly Ile Thr His Gly Met Asp Glu Leu Tyr Lys
225                 230                 235
```

<210> SEQ ID NO 12
<211> LENGTH: 238
<212> TYPE: PRT
<213> ORGANISM: Artificial Sequence
<220> FEATURE:
<223> OTHER INFORMATION: Description of Artificial Sequence: Synthetic
      gfp gene (Papillomavirusized)
<220> FEATURE:
<223> OTHER INFORMATION: Codons of humanized gfp gene replaced with
      synonymous codons used at relatively high
      frequency by papillomavirus genes

<400> SEQUENCE: 12

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160
```

```
Ile Lys Val Asn Phe Lys Ile Ile Arg His Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr His Gly Met Asp Glu Leu Tyr Lys
225                 230                 235

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Ala(GCA)

<400> SEQUENCE: 13
taaggactgt aagactt                                                  17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Arg(CGA)

<400> SEQUENCE: 14
cgagccagcc aggagtc                                                  17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Asn(AAC)

<400> SEQUENCE: 15
ctagattggc aggaatt                                                  17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Asp(GAC)

<400> SEQUENCE: 16
taagatatat agattat                                                  17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for  Cys(TGC)

<400> SEQUENCE: 17
aagtcttagt agagatt                                                  17
```

-continued

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Glu(GAA)

<400> SEQUENCE: 18
tatttctaca cagcatt                                                17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Gln(CAA)

<400> SEQUENCE: 19
ctaggacaat aggaatt                                                17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Gly(GGA)

<400> SEQUENCE: 20
tactctcttc tgggttt                                                17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for His(CAC)

<400> SEQUENCE: 21
tgccgtgact cggattc                                                17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Ile(ATC)

<400> SEQUENCE: 22
tagaaataag agggctt                                                17

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Leu(CTA)

<400> SEQUENCE: 23 tactttttatt tggattt                                               17

```
<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Leu(CTT)

<400> SEQUENCE: 24
tattagggag aggattt                                                  17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Lys(AAA)

<400> SEQUENCE: 25
tcactatgga gatttta                                                  17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Lys(AAG)

<400> SEQUENCE: 26
cgcccaacgt ggggctc                                                  17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Met (elong)

<400> SEQUENCE: 27
tagtacggga aggattt                                                  17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Phe(TTC)

<400> SEQUENCE: 28
tgtttatggg atacaat                                                  17

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Pro(CCA)

<400> SEQUENCE: 29
tcaagaagaa ggagcta                                                  17
```

```
<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Pro(CCI)

<400> SEQUENCE: 30
gggctcgtcc gggattt                                               17

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Ser(AGC)

<400> SEQUENCE: 31
ataagaaagg aagatcg                                               17

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Thr(ACA)

<400> SEQUENCE: 32
tgtcttgaga agagaag                                               17

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Tyr(TAC)

<400> SEQUENCE: 33
tggtaaaaag aggattt                                               17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide specific for Val(GTA)

<400> SEQUENCE: 34
tcagagtgtt cattggt                                               17

<210> SEQ ID NO 35
<211> LENGTH: 732
<212> TYPE: DNA
<213> ORGANISM: Artificial Sequence
<220> FEATURE:
<223> OTHER INFORMATION: Description of Artificial Sequence:
      Ala(GCA)5GFP
<220> FEATURE:
<221> NAME/KEY: CDS
<222> LOCATION: (1)..(732)

<400> SEQUENCE: 35 atg agc agc agc agc agc agc aag ggc gag gaa ctg ttc act ggc gtg      48
```

```
Met Ser Ser Ser Ser Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                 165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
             180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
         195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
     210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 36
<211> LENGTH: 243
<212> TYPE: PRT
<213> ORGANISM: Artificial Sequence
<220> FEATURE:
<223> OTHER INFORMATION: Description of Artificial Sequence:
      Ala(GCA)5GFP

<400> SEQUENCE: 36

Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30
```

-continued

```
Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
                180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 37
<211> LENGTH: 732
<212> TYPE: DNA
<213> ORGANISM: Artificial Sequence
<220> FEATURE:
<223> OTHER INFORMATION: Description of Artificial Sequence:
      Ala(GCC)5GFP
<220> FEATURE:
<221> NAME/KEY: CDS
<222> LOCATION: (1)..(732)

<400> SEQUENCE: 37 atg gcc gcc gcc gcc agc aag ggc gag gaa ctg ttc act ggc gtg       48
Met Ala Ala Ala Ala Ser Lys Gly Glu Glu Leu Phe Thr Gly Val
 1               5                  10                  15 gtc cca att ctc gtg gaa ctg gat ggc gat gtg aat ggg cac aaa ttt   96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95
```

```
tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 38
<211> LENGTH: 243
<212> TYPE: PRT
<213> ORGANISM: Artificial Sequence
<220> FEATURE:
<223> OTHER INFORMATION: Description of Artificial Sequence:
      Ala(GCC)5GFP

<400> SEQUENCE: 38

Met Ala Ala Ala Ala Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160
```

-continued

```
Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 39
<211> LENGTH: 732
<212> TYPE: DNA
<213> ORGANISM: Artificial Sequence
<220> FEATURE:
<223> OTHER INFORMATION: Description of Artificial Sequence:
      Ala(GCG)5GFP
<220> FEATURE:
<221> NAME/KEY: CDS
<222> LOCATION: (1)..(732)

<400> SEQUENCE: 39

```
atg gcg gcg gcg gcg gcg agc aag ggc gag gaa ctg ttc act ggc gtg        48
Met Ala Ala Ala Ala Ala Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190
```

```
atc ggc gac ggc cct gtg ctc ctc cca gac aac cat tac ctg tcc acc      624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 40
<211> LENGTH: 243
<212> TYPE: PRT
<213> ORGANISM: Artificial Sequence
<220> FEATURE:
<223> OTHER INFORMATION: Description of Artificial Sequence:
      Ala(GCG)5GFP

<400> SEQUENCE: 40

```
Met Ala Ala Ala Ala Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 41
<211> LENGTH: 732
<212> TYPE: DNA
<213> ORGANISM: Artificial Sequence

```
<220> FEATURE:
<223> OTHER INFORMATION: Description of Artificial Sequence:
      Ala(GCT)5GFP
<220> FEATURE:
<221> NAME/KEY: CDS
<222> LOCATION: (1)..(732)

<400> SEQUENCE: 41 atg gct gct gct gct gct agc aag ggc gag gaa ctg ttc act ggc gtg        48
Met Ala Ala Ala Ala Ala Ser Lys Gly Glu Glu Leu Phe Thr Gly Val
  1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 42
<211> LENGTH: 243
<212> TYPE: PRT
<213> ORGANISM: Artificial Sequence
<220> FEATURE:
<223> OTHER INFORMATION: Description of Artificial Sequence:
```

Ala(GCT)5GFP

<400> SEQUENCE: 42

```
Met Ala Ala Ala Ala Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 43
<211> LENGTH: 732
<212> TYPE: DNA
<213> ORGANISM: Artificial Sequence
<220> FEATURE:
<223> OTHER INFORMATION: Description of Artificial Sequence:
      Arg(AGA)5GFP
<220> FEATURE:
<221> NAME/KEY: CDS
<222> LOCATION: (1)..(732)

<400> SEQUENCE: 43

```
atg aga aga aga aga aga agc aag ggc gag gaa ctg ttc act ggc gtg      48
Met Arg Arg Arg Arg Arg Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
```

```
          50                  55                  60
ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 44
<211> LENGTH: 243
<212> TYPE: PRT
<213> ORGANISM: Artificial Sequence
<220> FEATURE:
<223> OTHER INFORMATION: Description of Artificial Sequence:
      Arg(AGA)5GFP

<400> SEQUENCE: 44

Met Arg Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
```

```
              100                 105                 110
Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 45
<211> LENGTH: 732
<212> TYPE: DNA
<213> ORGANISM: Artificial Sequence
<220> FEATURE:
<223> OTHER INFORMATION: Description of Artificial Sequence:
      Arg(AGG)5GFP
<220> FEATURE:
<221> NAME/KEY: CDS
<222> LOCATION: (1)..(732)

<400> SEQUENCE: 45 atg agg agg agg agg agg agc aag ggc gag gaa ctg ttc act ggc gtg    48
Met Arg Arg Arg Arg Arg Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag   336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc   384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac   432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac   480
```

```
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys
```

<210> SEQ ID NO 46
<211> LENGTH: 243
<212> TYPE: PRT
<213> ORGANISM: Artificial Sequence
<220> FEATURE:
<223> OTHER INFORMATION: Description of Artificial Sequence:
    Arg(AGG)5GFP

<400> SEQUENCE: 46

```
Met Arg Arg Arg Arg Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220
```

Leu Leu Glu Phe Val Thr Ala Ala Gly Ile Thr His Gly Met Asp Glu
225                 230                 235                 240

Leu Tyr Lys

<210> SEQ ID NO 47
<211> LENGTH: 732
<212> TYPE: DNA
<213> ORGANISM: Artificial Sequence
<220> FEATURE:
<223> OTHER INFORMATION: Description of Artificial Sequence:
      Arg(CGA)5GFP
<220> FEATURE:
<221> NAME/KEY: CDS
<222> LOCATION: (1)..(732)

<400> SEQUENCE: 47

```
atg cga cga cga cga cga agc aag ggc gag gaa ctg ttc act ggc gtg      48
Met Arg Arg Arg Arg Arg Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240
```

```
ctg tac aag tga                                                    732
Leu Tyr Lys <210> SEQ ID NO 48
<211> LENGTH: 243
<212> TYPE: PRT
<213> ORGANISM: Artificial Sequence
<220> FEATURE:
<223> OTHER INFORMATION: Description of Artificial Sequence:
      Arg(CGA)5GFP

<400> SEQUENCE: 48

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 49
<211> LENGTH: 732
<212> TYPE: DNA
<213> ORGANISM: Artificial Sequence
<220> FEATURE:
<223> OTHER INFORMATION: Description of Artificial Sequence:
      Arg(CGC)5GFP
<220> FEATURE:
<221> NAME/KEY: CDS
<222> LOCATION: (1)..(732)

<400> SEQUENCE: 49 atg cgc cgc cgc cgc cgc agc aag ggc gag gaa ctg ttc act ggc gtg    48
Met Arg Arg Arg Arg Arg Ser Lys Gly Glu Glu Leu Phe Thr Gly Val
 1               5                  10                  15
```

```
gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
 130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                 165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
             180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
         195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
 210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 50
<211> LENGTH: 243
<212> TYPE: PRT
<213> ORGANISM: Artificial Sequence
<220> FEATURE:
<223> OTHER INFORMATION: Description of Artificial Sequence:
      Arg(CGC)5GFP

<400> SEQUENCE: 50

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45
```

```
Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
                180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys

<210> SEQ ID NO 51
<211> LENGTH: 732
<212> TYPE: DNA
<213> ORGANISM: Artificial Sequence
<220> FEATURE:
<223> OTHER INFORMATION: Description of Artificial Sequence:
      Arg(CGG)5GFP
<220> FEATURE:
<221> NAME/KEY: CDS
<222> LOCATION: (1)..(732)

<400> SEQUENCE: 51 atg cgg cgg cgg cgg cgg agc aag ggc gag gaa ctg ttc act ggc gtg      48
Met Arg Arg Arg Arg Arg Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
                100                 105                 110
```

```
acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 52
<211> LENGTH: 243
<212> TYPE: PRT
<213> ORGANISM: Artificial Sequence
<220> FEATURE:
<223> OTHER INFORMATION: Description of Artificial Sequence:
      Arg(CGG)5GFP

<400> SEQUENCE: 52

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175
```

```
Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 53
<211> LENGTH: 732
<212> TYPE: DNA
<213> ORGANISM: Artificial Sequence
<220> FEATURE:
<223> OTHER INFORMATION: Description of Artificial Sequence:
      Arg(CGT)5GFP
<220> FEATURE:
<221> NAME/KEY: CDS
<222> LOCATION: (1)..(732)

<400> SEQUENCE: 53
```

| | | | | | | | | | | | | | | | | |
|---|---|---|---|---|---|---|---|---|---|---|---|---|---|---|---|---|
| atg | cgt | cgt | cgt | cgt | cgt | agc | aag | ggc | gag | gaa | ctg | ttc | act | ggc | gtg | 48 |
| Met | Arg | Arg | Arg | Arg | Arg | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| | 50 | | | | | 55 | | | | | 60 | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |

```
          195                 200                 205
cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 54
<211> LENGTH: 243
<212> TYPE: PRT
<213> ORGANISM: Artificial Sequence
<220> FEATURE:
<223> OTHER INFORMATION: Description of Artificial Sequence:
      Arg(CGT)5GFP

<400> SEQUENCE: 54

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 55
<211> LENGTH: 732
<212> TYPE: DNA
<213> ORGANISM: Artificial Sequence
<220> FEATURE:
<223> OTHER INFORMATION: Description of Artificial Sequence:
      Asn(AAC)5GFP
```

<220> FEATURE:
<221> NAME/KEY: CDS
<222> LOCATION: (1)..(732)

<400> SEQUENCE: 55

```
atg aac aac aac aac aac agc aag ggc gag gaa ctg ttc act ggc gtg      48
Met Asn Asn Asn Asn Asn Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 56
<211> LENGTH: 243
<212> TYPE: PRT
<213> ORGANISM: Artificial Sequence
<220> FEATURE:
<223> OTHER INFORMATION: Description of Artificial Sequence:
      Asn(AAC)5GFP

<400> SEQUENCE: 56

-continued

```
Met Asn Asn Asn Asn Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
             100                 105                 110

Thr Arg Ala Glu Val Lys Phe Glu Gly Asp Thr Leu Val Asn Arg Ile
         115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 57
<211> LENGTH: 732
<212> TYPE: DNA
<213> ORGANISM: Artificial Sequence
<220> FEATURE:
<223> OTHER INFORMATION: Description of Artificial Sequence: Asn(AAT)5GFP
<220> FEATURE:
<221> NAME/KEY: CDS
<222> LOCATION: (1)..(732)

<400> SEQUENCE: 57

```
atg aat aat aat aat aat agc aag ggc gag gaa ctg ttc act ggc gtg    48
Met Asn Asn Asn Asn Asn Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca   240
```

```
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 58
<211> LENGTH: 243
<212> TYPE: PRT
<213> ORGANISM: Artificial Sequence
<220> FEATURE:
<223> OTHER INFORMATION: Description of Artificial Sequence:
      Asn(AAT)5GFP

<400> SEQUENCE: 58

Met Asn Asn Asn Asn Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
```

```
                115                 120                 125
       Glu Leu Lys Gly Ile Asp Phe Lys Glu Asp Gly Asn Ile Leu Gly His
           130                 135                 140

Lys Leu Glu Tyr Asn Tyr Asn Ser His Asn Val Tyr Ile Met Ala Asp
       145                 150                 155                 160

Lys Gln Lys Asn Gly Ile Lys Val Asn Phe Lys Ile Arg His Asn Ile
                       165                 170                 175

Glu Asp Gly Ser Val Gln Leu Ala Asp His Tyr Gln Gln Asn Thr Pro
                   180                 185                 190

Ile Gly Asp Gly Pro Val Leu Leu Pro Asp Asn His Tyr Leu Ser Thr
                   195                 200                 205

Gln Ser Ala Leu Ser Lys Asp Pro Asn Glu Lys Arg Asp His Met Val
           210                 215                 220

Leu Leu Glu Phe Val Thr Ala Ala Gly Ile Thr His Gly Met Asp Glu
       225                 230                 235                 240

Leu Tyr Lys

<210> SEQ ID NO 59
<211> LENGTH: 732
<212> TYPE: DNA
<213> ORGANISM: Artificial Sequence
<220> FEATURE:
<223> OTHER INFORMATION: Description of Artificial Sequence:
      Asp(GAC)5GFP
<220> FEATURE:
<221> NAME/KEY: CDS
<222> LOCATION: (1)..(732)

<400> SEQUENCE: 59 atg gac gac gac gac gac agc aag ggc gag gaa ctg ttc act ggc gtg      48
Met Asp Asp Asp Asp Asp Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160
```

```
aag caa aag aat ggc atc aag gtc aac ttc aag atc aga cac aac att     528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 60
<211> LENGTH: 243
<212> TYPE: PRT
<213> ORGANISM: Artificial Sequence
<220> FEATURE:
<223> OTHER INFORMATION: Description of Artificial Sequence:
    Asp(GAC)5GFP

<400> SEQUENCE: 60

```
Met Asp Asp Asp Asp Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240
```

Leu Tyr Lys

<210> SEQ ID NO 61
<211> LENGTH: 732
<212> TYPE: DNA
<213> ORGANISM: Artificial Sequence
<220> FEATURE:
<223> OTHER INFORMATION: Description of Artificial Sequence:
      Asp(GAT)5GFP
<220> FEATURE:
<221> NAME/KEY: CDS
<222> LOCATION: (1)..(732)

<400> SEQUENCE: 61

| | | |
|---|---|---|
| atg gat gat gat gat gat agc aag ggc gag gaa ctg ttc act ggc gtg<br>Met Asp Asp Asp Asp Asp Ser Lys Gly Glu Glu Leu Phe Thr Gly Val<br>1              5                    10                  15 | | 48 |
| gtc cca att ctc gtg gaa ctg gat ggc gat gtg aat ggg cac aaa ttt<br>Val Pro Ile Leu Val Glu Leu Asp Gly Asp Val Asn Gly His Lys Phe<br>              20                    25                    30 | | 96 |
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>        35                    40                    45 | | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50                    55                    60 | | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                    70                    75                  80 | | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                    85                    90                    95 | | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>              100                   105                 110 | | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>            115                   120                 125 | | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>130                   135                 140 | | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                   150                 155                 160 | | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                    165                 170                 175 | | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>              180                   185                 190 | | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>            195                   200                 205 | | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210                   215                 220 | | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                   230                 235                 240 | | 720 |
| ctg tac aag tga<br>Leu Tyr Lys | | 732 |

<210> SEQ ID NO 62
<211> LENGTH: 243
<212> TYPE: PRT
<213> ORGANISM: Artificial Sequence
<220> FEATURE:
<223> OTHER INFORMATION: Description of Artificial Sequence: Asp(GAT)5GFP

<400> SEQUENCE: 62

```
Met Asp Asp Asp Asp Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 63
<211> LENGTH: 732
<212> TYPE: DNA
<213> ORGANISM: Artificial Sequence
<220> FEATURE:
<223> OTHER INFORMATION: Description of Artificial Sequence: Cys(TGC)5GFP
<220> FEATURE:
<221> NAME/KEY: CDS
<222> LOCATION: (1)..(732)

<400> SEQUENCE: 63

```
atg tgc tgc tgc tgc agc aag ggc gag gaa ctg ttc act ggc gtg       48
Met Cys Cys Cys Cys Ser Lys Gly Glu Glu Leu Phe Thr Gly Val
 1               5                  10                  15 gtc cca att ctc gtg gaa ctg gat ggc gat gtg aat ggg cac aaa ttt   96
Val Pro Ile Leu Val Glu Leu Asp Gly Asp Val Asn Gly His Lys Phe
             20                  25                  30
```

```
tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 64
<211> LENGTH: 243
<212> TYPE: PRT
<213> ORGANISM: Artificial Sequence
<220> FEATURE:
<223> OTHER INFORMATION: Description of Artificial Sequence:
      Cys(TGC)5GFP

<400> SEQUENCE: 64

Met Cys Cys Cys Cys Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60
```

```
Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 65
<211> LENGTH: 732
<212> TYPE: DNA
<213> ORGANISM: Artificial Sequence
<220> FEATURE:
<223> OTHER INFORMATION: Description of Artificial Sequence:
      Cys(TGT)5GFP
<220> FEATURE:
<221> NAME/KEY: CDS
<222> LOCATION: (1)..(732)

<400> SEQUENCE: 65 atg tgt tgt tgt tgt tgt agc aag ggc gag gaa ctg ttc act ggc gtg      48
Met Cys Cys Cys Cys Cys Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
```

-continued

```
              115                 120                 125
gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 66
<211> LENGTH: 243
<212> TYPE: PRT
<213> ORGANISM: Artificial Sequence
<220> FEATURE:
<223> OTHER INFORMATION: Description of Artificial Sequence:
    Cys(TGT)5GFP

<400> SEQUENCE: 66

```
Met Cys Cys Cys Cys Ser Lys Gly Glu Glu Leu Phe Thr Gly Val
  1               5                  10                 15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190
```

```
Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 67
<211> LENGTH: 732
<212> TYPE: DNA
<213> ORGANISM: Artificial Sequence
<220> FEATURE:
<223> OTHER INFORMATION: Description of Artificial Sequence:
      Gln(CAA)5GFP
<220> FEATURE:
<221> NAME/KEY: CDS
<222> LOCATION: (1)..(732)

<400> SEQUENCE: 67 atg caa caa caa caa caa agc aag ggc gag gaa ctg ttc act ggc gtg      48
Met Gln Gln Gln Gln Gln Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
            20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
```

```
Gln Ser Ala Leu Ser Lys Asp Pro Asn Glu Lys Arg Asp His Met Val
        210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 68
<211> LENGTH: 243
<212> TYPE: PRT
<213> ORGANISM: Artificial Sequence
<220> FEATURE:
<223> OTHER INFORMATION: Description of Artificial Sequence:
      Gln(CAA)5GFP

<400> SEQUENCE: 68

```
Met Gln Gln Gln Gln Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 69
<211> LENGTH: 732
<212> TYPE: DNA
<213> ORGANISM: Artificial Sequence
<220> FEATURE:
<223> OTHER INFORMATION: Description of Artificial Sequence:
      Gln(CAG)5GFP
<220> FEATURE:
<221> NAME/KEY: CDS
<222> LOCATION: (1)..(732)

<400> SEQUENCE: 69

```
atg cag cag cag cag cag agc aag ggc gag gaa ctg ttc act ggc gtg      48
Met Gln Gln Gln Gln Gln Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
        35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 70
<211> LENGTH: 243
<212> TYPE: PRT
<213> ORGANISM: Artificial Sequence
<220> FEATURE:
<223> OTHER INFORMATION: Description of Artificial Sequence:
      Gln(CAG)5GFP

<400> SEQUENCE: 70

```
Met Gln Gln Gln Gln Gln Ser Lys Gly Glu Glu Leu Phe Thr Gly Val
1               5                   10                  15
```

-continued

```
Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 71
<211> LENGTH: 732
<212> TYPE: DNA
<213> ORGANISM: Artificial Sequence
<220> FEATURE:
<223> OTHER INFORMATION: Description of Artificial Sequence:
      Glu(GAA)5GFP
<220> FEATURE:
<221> NAME/KEY: CDS
<222> LOCATION: (1)..(732)

<400> SEQUENCE: 71 atg gaa gaa gaa gaa gaa agc aag ggc gag gaa ctg ttc act ggc gtg      48
Met Glu Glu Glu Glu Glu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80
```

```
gac cat atg aag cag cat gac ttt ttc aag agc gcc atg ccc gag ggc        288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
        100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 72
<211> LENGTH: 243
<212> TYPE: PRT
<213> ORGANISM: Artificial Sequence
<220> FEATURE:
<223> OTHER INFORMATION: Description of Artificial Sequence:
      Glu(GAA)5GFP

<400> SEQUENCE: 72

Met Glu Glu Glu Glu Ser Lys Gly Glu Glu Leu Phe Thr Gly Val
  1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
```

```
                130                  135                  140
Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 73
<211> LENGTH: 732
<212> TYPE: DNA
<213> ORGANISM: Artificial Sequence
<220> FEATURE:
<223> OTHER INFORMATION: Description of Artificial Sequence:
      Glu(GAG)5GFP
<220> FEATURE:
<221> NAME/KEY: CDS
<222> LOCATION: (1)..(732)

<400> SEQUENCE: 73 atg gag gag gag gag gag agc aag ggc gag gaa ctg ttc act ggc gtg        48
Met Glu Glu Glu Glu Glu Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175
```

```
gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 74
<211> LENGTH: 243
<212> TYPE: PRT
<213> ORGANISM: Artificial Sequence
<220> FEATURE:
<223> OTHER INFORMATION: Description of Artificial Sequence:
      Glu(GAG)5GFP

<400> SEQUENCE: 74

```
Met Glu Glu Glu Glu Glu Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
     65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

```
<210> SEQ ID NO 75
<211> LENGTH: 732
<212> TYPE: DNA
<213> ORGANISM: Artificial Sequence
<220> FEATURE:
<223> OTHER INFORMATION: Description of Artificial Sequence:
      Gly(GGA)5GFP
<220> FEATURE:
<221> NAME/KEY: CDS
<222> LOCATION: (1)..(732)

<400> SEQUENCE: 75 atg gga gga gga gga gga agc aag ggc gag gaa ctg ttc act ggc gtg      48
Met Gly Gly Gly Gly Gly Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys

<210> SEQ ID NO 76
<211> LENGTH: 243
```

```
<212> TYPE: PRT
<213> ORGANISM: Artificial Sequence
<220> FEATURE:
<223> OTHER INFORMATION: Description of Artificial Sequence:
      Gly(GGA)5GFP

<400> SEQUENCE: 76

Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 77
<211> LENGTH: 732
<212> TYPE: DNA
<213> ORGANISM: Artificial Sequence
<220> FEATURE:
<223> OTHER INFORMATION: Description of Artificial Sequence:
      Gly(GGC)5GFP
<220> FEATURE:
<221> NAME/KEY: CDS
<222> LOCATION: (1)..(732)

<400> SEQUENCE: 77 atg ggc ggc ggc ggc agc aag ggc gag gaa ctg ttc act ggc gtg        48
Met Gly Gly Gly Gly Ser Lys Gly Glu Glu Leu Phe Thr Gly Val
 1               5                  10                  15 gtc cca att ctc gtg gaa ctg gat ggc gat gtg aat ggg cac aaa ttt   96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc  144
Ser Val Ser Gly Glu Gly Glu Gly Asp Ala Thr Tyr Gly Lys Leu Thr
```

```
ctg aaa ttc atc tgc acc act gga aag ctc cct gtg cca tgg cca aca    192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 78
<211> LENGTH: 243
<212> TYPE: PRT
<213> ORGANISM: Artificial Sequence
<220> FEATURE:
<223> OTHER INFORMATION: Description of Artificial Sequence:
      Gly(GGC)5GFP

<400> SEQUENCE: 78

Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80
```

```
Asp His Met Lys Gln His Asp Phe Phe Lys Ser Ala Met Pro Glu Gly
             85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 79
<211> LENGTH: 732
<212> TYPE: DNA
<213> ORGANISM: Artificial Sequence
<220> FEATURE:
<223> OTHER INFORMATION: Description of Artificial Sequence:
       Gly(GGG)5GFP
<220> FEATURE:
<221> NAME/KEY: CDS
<222> LOCATION: (1)..(732)

<400> SEQUENCE: 79

```
atg ggg ggg ggg ggg ggg agc aag ggc gag gaa ctg ttc act ggc gtg      48
Met Gly Gly Gly Gly Gly Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
```

```
Glu Leu Lys Gly Ile Asp Phe Lys Glu Asp Gly Asn Ile Leu Gly His
        130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 80
<211> LENGTH: 243
<212> TYPE: PRT
<213> ORGANISM: Artificial Sequence
<220> FEATURE:
<223> OTHER INFORMATION: Description of Artificial Sequence:
    Gly(GGG)5GFP

<400> SEQUENCE: 80

```
Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205
```

```
Gln Ser Ala Leu Ser Lys Asp Pro Asn Glu Lys Arg Asp His Met Val
    210                 215                 220
Leu Leu Glu Phe Val Thr Ala Ala Gly Ile Thr His Gly Met Asp Glu
225                 230                 235                 240
Leu Tyr Lys

<210> SEQ ID NO 81
<211> LENGTH: 732
<212> TYPE: DNA
<213> ORGANISM: Artificial Sequence
<220> FEATURE:
<223> OTHER INFORMATION: Description of Artificial Sequence:
      Gly(GGT)5GFP
<220> FEATURE:
<221> NAME/KEY: CDS
<222> LOCATION: (1)..(732)

<400> SEQUENCE: 81 atg ggt ggt ggt ggt ggt agc aag ggc gag gaa ctg ttc act ggc gtg      48
Met Gly Gly Gly Gly Gly Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
        130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
                180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
        210                 215                 220
```

```
ctg ctg gag ttt gtg acc gct gct ggg atc aca cat ggc atg gac gag    720
Leu Leu Glu Phe Val Thr Ala Ala Gly Ile Thr His Gly Met Asp Glu
225             230                 235                 240 ctg tac aag tga                                                    732
Leu Tyr Lys
```

<210> SEQ ID NO 82
<211> LENGTH: 243
<212> TYPE: PRT
<213> ORGANISM: Artificial Sequence
<220> FEATURE:
<223> OTHER INFORMATION: Description of Artificial Sequence:
      Gly(GGT)5GFP

<400> SEQUENCE: 82

```
Met Gly Gly Gly Gly Ser Lys Gly Glu Glu Leu Phe Thr Gly Val
 1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 83
<211> LENGTH: 732
<212> TYPE: DNA
<213> ORGANISM: Artificial Sequence
<220> FEATURE:
<223> OTHER INFORMATION: Description of Artificial Sequence:
      His(CAC)5GFP
<220> FEATURE:
<221> NAME/KEY: CDS
<222> LOCATION: (1)..(732)

<400> SEQUENCE: 83

```
atg cac cac cac cac cac agc aag ggc gag gaa ctg ttc act ggc gtg         48
Met His His His His His Ser Lys Gly Glu Glu Leu Phe Thr Gly Val
 1               5                  10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
 130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                 165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
             180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
         195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
 210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys
```

<210> SEQ ID NO 84
<211> LENGTH: 243
<212> TYPE: PRT
<213> ORGANISM: Artificial Sequence
<220> FEATURE:
<223> OTHER INFORMATION: Description of Artificial Sequence:
      His(CAC)5GFP

<400> SEQUENCE: 84

Met His His His His His Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

```
Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 85
<211> LENGTH: 732
<212> TYPE: DNA
<213> ORGANISM: Artificial Sequence
<220> FEATURE:
<223> OTHER INFORMATION: Description of Artificial Sequence:
      His(CAT)5GFP
<220> FEATURE:
<221> NAME/KEY: CDS
<222> LOCATION: (1)..(732)

<400> SEQUENCE: 85 atg cat cat cat cat cat agc aag ggc gag gaa ctg ttc act ggc gtg    48
Met His His His His His Ser Lys Gly Glu Glu Leu Phe Thr Gly Val
 1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95
```

-continued

```
tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 86
<211> LENGTH: 243
<212> TYPE: PRT
<213> ORGANISM: Artificial Sequence
<220> FEATURE:
<223> OTHER INFORMATION: Description of Artificial Sequence:
      His(CAT)5GFP

<400> SEQUENCE: 86

```
Met His His His His Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
```

| | | | | |
|---|---|---|---|---|
| 145 | | 150 | 155 | 160 |

Lys Gln Lys Asn Gly Ile Lys Val Asn Phe Lys Ile Arg His Asn Ile
                165              170             175

Glu Asp Gly Ser Val Gln Leu Ala Asp His Tyr Gln Gln Asn Thr Pro
         180              185             190

Ile Gly Asp Gly Pro Val Leu Leu Pro Asp Asn His Tyr Leu Ser Thr
            195             200             205

Gln Ser Ala Leu Ser Lys Asp Pro Asn Glu Lys Arg Asp His Met Val
     210              215             220

Leu Leu Glu Phe Val Thr Ala Ala Gly Ile Thr His Gly Met Asp Glu
225             230             235            240

Leu Tyr Lys

<210> SEQ ID NO 87
<211> LENGTH: 732
<212> TYPE: DNA
<213> ORGANISM: Artificial Sequence
<220> FEATURE:
<223> OTHER INFORMATION: Description of Artificial Sequence:
     Ile(ATA)5GFP
<220> FEATURE:
<221> NAME/KEY: CDS
<222> LOCATION: (1)..(732)

<400> SEQUENCE: 87

| | |
|---|---|
| atg ata ata ata ata ata agc aag ggc gag gaa ctg ttc act ggc gtg<br>Met Ile Ile Ile Ile Ile Ser Lys Gly Glu Glu Leu Phe Thr Gly Val<br>  1              5                 10              15 | 48 |
| gtc cca att ctc gtg gaa ctg gat ggc gat gtg aat ggg cac aaa ttt<br>Val Pro Ile Leu Val Glu Leu Asp Gly Asp Val Asn Gly His Lys Phe<br>             20                 25              30 | 96 |
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>         35              40               45 | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50              55               60 | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65              70              75              80 | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                  85               90              95 | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>            100             105            110 | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>        115             120            125 | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>130             135            140 | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145             150            155            160 | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                165             170            175 | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro | 576 |

```
                180                 185                 190
atc ggc gac ggc cct gtg ctc ctc cca gac aac cat tac ctg tcc acc      624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 88
<211> LENGTH: 243
<212> TYPE: PRT
<213> ORGANISM: Artificial Sequence
<220> FEATURE:
<223> OTHER INFORMATION: Description of Artificial Sequence:
      Ile(ATA)5GFP

<400> SEQUENCE: 88

Met Ile Ile Ile Ile Ile Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 89
<211> LENGTH: 732
<212> TYPE: DNA
```

<213> ORGANISM: Artificial Sequence
<220> FEATURE:
<223> OTHER INFORMATION: Description of Artificial Sequence: Ile(ATC)5GFP
<220> FEATURE:
<221> NAME/KEY: CDS
<222> LOCATION: (1)..(732)

<400> SEQUENCE: 89

| | | |
|---|---|---|
| atg atc atc atc atc atc agc aag ggc gag gaa ctg ttc act ggc gtg<br>Met Ile Ile Ile Ile Ile Ser Lys Gly Glu Glu Leu Phe Thr Gly Val<br>1                       5                   10                 15 | 48 |
| gtc cca att ctc gtg gaa ctg gat ggc gat gtg aat ggg cac aaa ttt<br>Val Pro Ile Leu Val Glu Leu Asp Gly Asp Val Asn Gly His Lys Phe<br>                 20                   25                 30 | 96 |
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>              35                   40                 45 | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br> 50                   55                   60 | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                      70                  75                 80 | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                 85                   90                 95 | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>           100                 105               110 | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>           115                 120               125 | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>     130                 135               140 | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                  150               155              160 | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                 165               170               175 | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>           180                 185               190 | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>     195                 200               205 | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210                  215               220 | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                  230               235              240 | 720 |
| ctg tac aag tga<br>Leu Tyr Lys | 732 |

<210> SEQ ID NO 90
<211> LENGTH: 243
<212> TYPE: PRT
<213> ORGANISM: Artificial Sequence
<220> FEATURE:

<223> OTHER INFORMATION: Description of Artificial Sequence:
       Ile(ATC)5GFP

<400> SEQUENCE: 90

```
Met Ile Ile Ile Ile Ile Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 91
<211> LENGTH: 732
<212> TYPE: DNA
<213> ORGANISM: Artificial Sequence
<220> FEATURE:
<223> OTHER INFORMATION: Description of Artificial Sequence:
       Ile(ATT)5GFP
<220> FEATURE:
<221> NAME/KEY: CDS
<222> LOCATION: (1)..(732)

<400> SEQUENCE: 91

```
atg att att att att att agc aag ggc gag gaa ctg ttc act ggc gtg         48
Met Ile Ile Ile Ile Ile Ser Lys Gly Glu Glu Leu Phe Thr Gly Val
  1               5                  10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca        192
```

```
                                                                        240
ctg gtc act acc ttc tct tat ggc gtg cag tgc ttt tcc aga tac cca
Leu Val Thr Thr Phe Ser Tyr Gly Val Gln Cys Phe Ser Arg Tyr Pro
 65             70                  75                  80

288
gac cat atg aag cag cat gac ttt ttc aag agc gcc atg ccc gag ggc
Asp His Met Lys Gln His Asp Phe Phe Lys Ser Ala Met Pro Glu Gly
                85                  90                  95

336
tat gtg cag gag aga acc atc ttt ttc aaa gat gac ggg aac tac aag
Tyr Val Gln Glu Arg Thr Ile Phe Phe Lys Asp Asp Gly Asn Tyr Lys
            100                 105                 110

384
acc cgc gct gaa gtc aag ttc gaa ggt gac acc ctg gtg aat aga atc
Thr Arg Ala Glu Val Lys Phe Glu Gly Asp Thr Leu Val Asn Arg Ile
        115                 120                 125

432
gag ctg aag ggc att gac ttt aag gag gat gga aac att ctc ggc cac
Glu Leu Lys Gly Ile Asp Phe Lys Glu Asp Gly Asn Ile Leu Gly His
130                 135                 140

480
aag ctg gaa tac aac tat aac tcc cac aat gtg tac atc atg gcc gac
Lys Leu Glu Tyr Asn Tyr Asn Ser His Asn Val Tyr Ile Met Ala Asp
145                 150                 155                 160

528
aag caa aag aat ggc atc aag gtc aac ttc aag atc aga cac aac att
Lys Gln Lys Asn Gly Ile Lys Val Asn Phe Lys Ile Arg His Asn Ile
                165                 170                 175

576
gag gat gga tcc gtg cag ctg gcc gac cat tat caa cag aac act cca
Glu Asp Gly Ser Val Gln Leu Ala Asp His Tyr Gln Gln Asn Thr Pro
            180                 185                 190

624
atc ggc gac ggc cct gtg ctc ctc cca gac aac cat tac ctg tcc acc
Ile Gly Asp Gly Pro Val Leu Leu Pro Asp Asn His Tyr Leu Ser Thr
        195                 200                 205

672
cag tct gcc ctg tct aaa gat ccc aac gaa aag aga gac cac atg gtc
Gln Ser Ala Leu Ser Lys Asp Pro Asn Glu Lys Arg Asp His Met Val
210                 215                 220

720
ctg ctg gag ttt gtg acc gct gct ggg atc aca cat ggc atg gac gag
Leu Leu Glu Phe Val Thr Ala Ala Gly Ile Thr His Gly Met Asp Glu
225                 230                 235                 240

732
ctg tac aag tga
Leu Tyr Lys

<210> SEQ ID NO 92
<211> LENGTH: 243
<212> TYPE: PRT
<213> ORGANISM: Artificial Sequence
<220> FEATURE:
<223> OTHER INFORMATION: Description of Artificial Sequence:
      Ile(ATT)5GFP

<400> SEQUENCE: 92

Met Ile Ile Ile Ile Ile Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95
```

```
Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 93
<211> LENGTH: 732
<212> TYPE: DNA
<213> ORGANISM: Artificial Sequence
<220> FEATURE:
<223> OTHER INFORMATION: Description of Artificial Sequence:
      Leu(CTA)5GFP
<220> FEATURE:
<221> NAME/KEY: CDS
<222> LOCATION: (1)..(732)

<400> SEQUENCE: 93 atg cta cta cta cta cta agc aag ggc gag gaa ctg ttc act ggc gtg        48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                 70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
        130                 135                 140
```

```
aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 94
<211> LENGTH: 243
<212> TYPE: PRT
<213> ORGANISM: Artificial Sequence
<220> FEATURE:
<223> OTHER INFORMATION: Description of Artificial Sequence:
      Leu(CTA)5GFP

<400> SEQUENCE: 94

Met Leu Leu Leu Leu Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220
```

```
Leu Leu Glu Phe Val Thr Ala Ala Gly Ile Thr His Gly Met Asp Glu
225                 230                 235                 240

Leu Tyr Lys

<210> SEQ ID NO 95
<211> LENGTH: 732
<212> TYPE: DNA
<213> ORGANISM: Artificial Sequence
<220> FEATURE:
<223> OTHER INFORMATION: Description of Artificial Sequence:
      Leu(CTC)5GFP
<220> FEATURE:
<221> NAME/KEY: CDS
<222> LOCATION: (1)..(732)

<400> SEQUENCE: 95 atg ctc ctc ctc ctc ctc agc aag ggc gag gaa ctg ttc act ggc gtg     48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca    240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc    288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag    336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240
```

```
ctg tac aag tga                                                              732
Leu Tyr Lys
```

```
<210> SEQ ID NO 96
<211> LENGTH: 243
<212> TYPE: PRT
<213> ORGANISM: Artificial Sequence
<220> FEATURE:
<223> OTHER INFORMATION: Description of Artificial Sequence:
      Leu(CTC)5GFP

<400> SEQUENCE: 96

Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

```
<210> SEQ ID NO 97
<211> LENGTH: 732
<212> TYPE: DNA
<213> ORGANISM: Artificial Sequence
<220> FEATURE:
<223> OTHER INFORMATION: Description of Artificial Sequence:
      Leu(CTG)5GFP
<220> FEATURE:
<221> NAME/KEY: CDS
<222> LOCATION: (1)..(732)

<400> SEQUENCE: 97 atg ctg ctg ctg ctg ctg agc aag ggc gag gaa ctg ttc act ggc gtg        48
Met Leu Leu Leu Leu Leu Ser Lys Gly Glu Glu Leu Phe Thr Gly Val
 1               5                  10                  15
```

```
gtc cca att ctc gtg gaa ctg gat ggc gat gtg aat ggg cac aaa ttt          96
Val Pro Ile Leu Val Glu Leu Asp Gly Asp Val Asn Gly His Lys Phe
         20                  25                  30 tct gtc agc gga gag ggt gaa ggt gat gcc aca tac gga aag ctc acc         144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca         192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca         240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc         288
Asp His Met Lys Gln His Asp Phe Phe Lys Ser Ala Met Pro Glu Gly
                     85                  90                  95 tat gtg cag gag aga acc atc ttt ttc aaa gat gac ggg aac tac aag         336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc         384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac         432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac         480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att         528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca         576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc         624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc         672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag         720
Leu Leu Glu Phe Val Thr Ala Ala Gly Ile Thr His Gly Met Asp Glu
225                 230                 235                 240 ctg tac aag tga                                                         732
Leu Tyr Lys <210> SEQ ID NO 98
<211> LENGTH: 243
<212> TYPE: PRT
<213> ORGANISM: Artificial Sequence
<220> FEATURE:
<223> OTHER INFORMATION: Description of Artificial Sequence:
      Leu(CTG)5GFP

<400> SEQUENCE: 98

Met Leu Leu Leu Leu Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45
```

```
Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 99
<211> LENGTH: 732
<212> TYPE: DNA
<213> ORGANISM: Artificial Sequence
<220> FEATURE:
<223> OTHER INFORMATION: Description of Artificial Sequence:
      Leu(CTT)5GFP
<220> FEATURE:
<221> NAME/KEY: CDS
<222> LOCATION: (1)..(732)

<400> SEQUENCE: 99 atg ctt ctt ctt ctt ctt agc aag ggc gag gaa ctg ttc act ggc gtg      48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
```

| | | | | | | | | | | | | | | | | |
|---|---|---|---|---|---|---|---|---|---|---|---|---|---|---|---|---|
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | | 115 | | | | 120 | | | | 125 | | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| 130 | | | | | 135 | | | | | 140 | | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | 210 | | | | | 215 | | | | | 220 | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

<210> SEQ ID NO 100
<211> LENGTH: 243
<212> TYPE: PRT
<213> ORGANISM: Artificial Sequence
<220> FEATURE:
<223> OTHER INFORMATION: Description of Artificial Sequence:
    Leu(CTT)5GFP

<400> SEQUENCE: 100

Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile

```
                     165                 170                 175
Glu Asp Gly Ser Val Gln Leu Ala Asp His Tyr Gln Gln Asn Thr Pro
            180                 185                 190
Ile Gly Asp Gly Pro Val Leu Leu Pro Asp Asn His Tyr Leu Ser Thr
        195                 200                 205
Gln Ser Ala Leu Ser Lys Asp Pro Asn Glu Lys Arg Asp His Met Val
    210                 215                 220
Leu Leu Glu Phe Val Thr Ala Ala Gly Ile Thr His Gly Met Asp Glu
225                 230                 235                 240
Leu Tyr Lys

<210> SEQ ID NO 101
<211> LENGTH: 732
<212> TYPE: DNA
<213> ORGANISM: Artificial Sequence
<220> FEATURE:
<223> OTHER INFORMATION: Description of Artificial Sequence:
      Leu(TTA)5GFP
<220> FEATURE:
<221> NAME/KEY: CDS
<222> LOCATION: (1)..(732)

<400> SEQUENCE: 101 atg tta tta tta tta tta agc aag ggc gag gaa ctg ttc act ggc gtg      48
Met Leu Leu Leu Leu Leu Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
```

```
                                                     -continued

Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc         672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag         720
Leu Leu Glu Phe Val Thr Ala Ala Gly Ile Thr His Gly Met Asp Glu
225                 230                 235                 240 ctg tac aag tga                                                         732
Leu Tyr Lys
```

<210> SEQ ID NO 102
<211> LENGTH: 243
<212> TYPE: PRT
<213> ORGANISM: Artificial Sequence
<220> FEATURE:
<223> OTHER INFORMATION: Description of Artificial Sequence:
      Leu(TTA)5GFP

<400> SEQUENCE: 102

```
Met Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 103
<211> LENGTH: 732
<212> TYPE: DNA
<213> ORGANISM: Artificial Sequence
<220> FEATURE:
<223> OTHER INFORMATION: Description of Artificial Sequence:

```
       Leu(TTG)5GFP
<220> FEATURE:
<221> NAME/KEY: CDS
<222> LOCATION: (1)..(732)

<400> SEQUENCE: 103 atg ttg ttg ttg ttg ttg agc aag ggc gag gaa ctg ttc act ggc gtg      48
Met Leu Leu Leu Leu Leu Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 104
<211> LENGTH: 243
<212> TYPE: PRT
<213> ORGANISM: Artificial Sequence
<220> FEATURE:
<223> OTHER INFORMATION: Description of Artificial Sequence:
      Leu(TTG)5GFP
```

-continued

```
<400> SEQUENCE: 104

Met Leu Leu Leu Leu Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
             100                 105                 110

Thr Arg Ala Glu Val Lys Phe Glu Gly Asp Thr Leu Val Asn Arg Ile
         115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 105
<211> LENGTH: 732
<212> TYPE: DNA
<213> ORGANISM: Artificial Sequence
<220> FEATURE:
<223> OTHER INFORMATION: Description of Artificial Sequence:
      Lys(AAA)5GFP
<220> FEATURE:
<221> NAME/KEY: CDS
<222> LOCATION: (1)..(732)

<400> SEQUENCE: 105 atg aaa aaa aaa aaa aaa agc aag ggc gag gaa ctg ttc act ggc gtg      48
Met Lys Lys Lys Lys Lys Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60
```

```
ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys
```

<210> SEQ ID NO 106
<211> LENGTH: 243
<212> TYPE: PRT
<213> ORGANISM: Artificial Sequence
<220> FEATURE:
<223> OTHER INFORMATION: Description of Artificial Sequence:
      Lys(AAA)5GFP

<400> SEQUENCE: 106

```
Met Lys Lys Lys Lys Ser Lys Gly Glu Glu Leu Phe Thr Gly Val
 1               5                   10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110
```

```
Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 107
<211> LENGTH: 732
<212> TYPE: DNA
<213> ORGANISM: Artificial Sequence
<220> FEATURE:
<223> OTHER INFORMATION: Description of Artificial Sequence:
      Lys(AAG)5GFP
<220> FEATURE:
<221> NAME/KEY: CDS
<222> LOCATION: (1)..(732)

<400> SEQUENCE: 107

```
atg aag aag aag aag aag agc aag ggc gag gaa ctg ttc act ggc gtg       48
Met Lys Lys Lys Lys Lys Ser Lys Gly Glu Glu Leu Phe Thr Gly Val
 1               5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                 70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160
```

```
aag caa aag aat ggc atc aag gtc aac ttc aag atc aga cac aac att    528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys
```

<210> SEQ ID NO 108
<211> LENGTH: 243
<212> TYPE: PRT
<213> ORGANISM: Artificial Sequence
<220> FEATURE:
<223> OTHER INFORMATION: Description of Artificial Sequence:
      Lys(AAG)5GFP

<400> SEQUENCE: 108

```
Met Lys Lys Lys Lys Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240
```

Leu Tyr Lys

<210> SEQ ID NO 109
<211> LENGTH: 732
<212> TYPE: DNA
<213> ORGANISM: Artificial Sequence
<220> FEATURE:
<223> OTHER INFORMATION: Description of Artificial Sequence: Phe(TTT)5GFP
<220> FEATURE:
<221> NAME/KEY: CDS
<222> LOCATION: (1)..(732)

<400> SEQUENCE: 109

| | | | | | | | | | | | | | | | | |
|---|---|---|---|---|---|---|---|---|---|---|---|---|---|---|---|---|
| atg | ttt | ttt | ttt | ttt | ttt | agc | aag | ggc | gag | gaa | ctg | ttc | act | ggc | gtg | 48 |
| Met | Phe | Phe | Phe | Phe | Phe | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| 50 | | | | | 55 | | | | | 60 | | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| 130 | | | | | 135 | | | | | 140 | | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | 210 | | | | | 215 | | | | | 220 | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

```
<210> SEQ ID NO 110
<211> LENGTH: 243
<212> TYPE: PRT
<213> ORGANISM: Artificial Sequence
<220> FEATURE:
<223> OTHER INFORMATION: Description of Artificial Sequence:
      Phe(TTT)5GFP

<400> SEQUENCE: 110

Met Leu Leu Leu Leu Leu Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 111
<211> LENGTH: 732
<212> TYPE: DNA
<213> ORGANISM: Artificial Sequence
<220> FEATURE:
<223> OTHER INFORMATION: Description of Artificial Sequence:
      Phe(TTC)5GFP
<220> FEATURE:
<221> NAME/KEY: CDS
<222> LOCATION: (1)..(732)

<400> SEQUENCE: 111 atg ttc ttc ttc ttc ttc agc aag ggc gag gaa ctg ttc act ggc gtg      48
Met Phe Phe Phe Phe Phe Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
```

```
                  20                        25                       30
tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
             35                       40                      45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
 50                      55                      60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                      70                      75                 80 gac cat atg aag cag cat gac ttt ttc aag agc gcc atg ccc gag ggc        288
Asp His Met Lys Gln His Asp Phe Phe Lys Ser Ala Met Pro Glu Gly
             85                       90                      95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
             100                      105                     110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
             115                      120                     125 gag ctg aag ggc att gac ttt aag gag gat gga aac att ctc ggc cac        432
Glu Leu Lys Gly Ile Asp Phe Lys Glu Asp Gly Asn Ile Leu Gly His
 130                     135                     140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
 145                     150                     155                160 aag caa aag aat ggc atc aag gtc aac ttc aag atc aga cac aac att        528
Lys Gln Lys Asn Gly Ile Lys Val Asn Phe Lys Ile Arg His Asn Ile
             165                      170                     175 gag gat gga tcc gtg cag ctg gcc gac cat tat caa cag aac act cca        576
Glu Asp Gly Ser Val Gln Leu Ala Asp His Tyr Gln Gln Asn Thr Pro
             180                      185                     190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
             195                      200                     205 cag tct gcc ctg tct aaa gat ccc aac gaa aag aga gac cac atg gtc        672
Gln Ser Ala Leu Ser Lys Asp Pro Asn Glu Lys Arg Asp His Met Val
 210                     215                     220 ctg ctg gag ttt gtg acc gct gct ggg atc aca cat ggc atg gac gag        720
Leu Leu Glu Phe Val Thr Ala Ala Gly Ile Thr His Gly Met Asp Glu
 225                     230                     235                240 ctg tac aag tga                                                        732
Leu Tyr Lys <210> SEQ ID NO 112
<211> LENGTH: 243
<212> TYPE: PRT
<213> ORGANISM: Artificial Sequence
<220> FEATURE:
<223> OTHER INFORMATION: Description of Artificial Sequence:
      Phe(TTC)5GFP

<400> SEQUENCE: 112

Met Phe Phe Phe Phe Phe Ser Lys Gly Glu Glu Leu Phe Thr Gly Val
 1               5                   10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60
```

```
Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 113
<211> LENGTH: 732
<212> TYPE: DNA
<213> ORGANISM: Artificial Sequence
<220> FEATURE:
<223> OTHER INFORMATION: Description of Artificial Sequence:
      Pro(CCC)5GFP
<220> FEATURE:
<221> NAME/KEY: CDS
<222> LOCATION: (1)..(732)

<400> SEQUENCE: 113 atg ccc ccc ccc ccc ccc agc aag ggc gag gaa ctg ttc act ggc gtg      48
Met Pro Pro Pro Pro Pro Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
```

```
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 114
<211> LENGTH: 243
<212> TYPE: PRT
<213> ORGANISM: Artificial Sequence
<220> FEATURE:
<223> OTHER INFORMATION: Description of Artificial Sequence:
      Pro(CCC)5GFP

<400> SEQUENCE: 114

Met Pro Pro Pro Pro Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
```

```
                    180                 185                 190
Ile Gly Asp Gly Pro Val Leu Leu Pro Asp Asn His Tyr Leu Ser Thr
        195                 200                 205
Gln Ser Ala Leu Ser Lys Asp Pro Asn Glu Lys Arg Asp His Met Val
    210                 215                 220
Leu Leu Glu Phe Val Thr Ala Ala Gly Ile Thr His Gly Met Asp Glu
225                 230                 235                 240
Leu Tyr Lys

<210> SEQ ID NO 115
<211> LENGTH: 732
<212> TYPE: DNA
<213> ORGANISM: Artificial Sequence
<220> FEATURE:
<223> OTHER INFORMATION: Description of Artificial Sequence:
      Pro(CCG)5GFP
<220> FEATURE:
<221> NAME/KEY: CDS
<222> LOCATION: (1)..(732)

<400> SEQUENCE: 115 atg ccg ccg ccg ccg ccg agc aag ggc gag gaa ctg ttc act ggc gtg       48
Met Pro Pro Pro Pro Pro Ser Lys Gly Glu Glu Leu Phe Thr Gly Val
  1               5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205
```

```
cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 116
<211> LENGTH: 243
<212> TYPE: PRT
<213> ORGANISM: Artificial Sequence
<220> FEATURE:
<223> OTHER INFORMATION: Description of Artificial Sequence:
      Pro(CCG)5GFP

<400> SEQUENCE: 116

```
Met Pro Pro Pro Pro Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
        50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 117
<211> LENGTH: 732
<212> TYPE: DNA
<213> ORGANISM: Artificial Sequence
<220> FEATURE:
<223> OTHER INFORMATION: Description of Artificial Sequence:
      Pro(CCT)5GFP
<220> FEATURE:
<221> NAME/KEY: CDS

```
<222> LOCATION: (1)..(732)

<400> SEQUENCE: 117 atg cct cct cct cct cct agc aag ggc gag gaa ctg ttc act ggc gtg      48
Met Pro Pro Pro Pro Pro Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 118
<211> LENGTH: 243
<212> TYPE: PRT
<213> ORGANISM: Artificial Sequence
<220> FEATURE:
<223> OTHER INFORMATION: Description of Artificial Sequence:
      Pro(CCT)5GFP

<400> SEQUENCE: 118

Met Pro Pro Pro Pro Pro Ser Lys Gly Glu Glu Leu Phe Thr Gly Val
```

```
                1               5                    10                       15
            Val Pro Ile Leu Val Glu Leu Asp Gly Asp Val Asn Gly His Lys Phe
                            20                  25                  30

Ser Val Ser Gly Glu Gly Glu Gly Asp Ala Thr Tyr Gly Lys Leu Thr
                        35                  40                  45

Leu Lys Phe Ile Cys Thr Thr Gly Lys Leu Pro Val Pro Trp Pro Thr
                    50                  55                  60

Leu Val Thr Thr Phe Ser Tyr Gly Val Gln Cys Phe Ser Arg Tyr Pro
            65                  70                  75                  80

Asp His Met Lys Gln His Asp Phe Phe Lys Ser Ala Met Pro Glu Gly
                            85                  90                  95

Tyr Val Gln Glu Arg Thr Ile Phe Phe Lys Asp Asp Gly Asn Tyr Lys
                        100                 105                 110

Thr Arg Ala Glu Val Lys Phe Glu Gly Asp Thr Leu Val Asn Arg Ile
                    115                 120                 125

Glu Leu Lys Gly Ile Asp Phe Lys Glu Asp Gly Asn Ile Leu Gly His
                        130                 135                 140

Lys Leu Glu Tyr Asn Tyr Asn Ser His Asn Val Tyr Ile Met Ala Asp
            145                 150                 155                 160

Lys Gln Lys Asn Gly Ile Lys Val Asn Phe Lys Ile Arg His Asn Ile
                            165                 170                 175

Glu Asp Gly Ser Val Gln Leu Ala Asp His Tyr Gln Gln Asn Thr Pro
                        180                 185                 190

Ile Gly Asp Gly Pro Val Leu Leu Pro Asp Asn His Tyr Leu Ser Thr
                    195                 200                 205

Gln Ser Ala Leu Ser Lys Asp Pro Asn Glu Lys Arg Asp His Met Val
                        210                 215                 220

Leu Leu Glu Phe Val Thr Ala Ala Gly Ile Thr His Gly Met Asp Glu
            225                 230                 235                 240

Leu Tyr Lys

<210> SEQ ID NO 119
<211> LENGTH: 732
<212> TYPE: DNA
<213> ORGANISM: Artificial Sequence
<220> FEATURE:
<223> OTHER INFORMATION: Description of Artificial Sequence:
      Pro(CGA)5GFP
<220> FEATURE:
<221> NAME/KEY: CDS
<222> LOCATION: (1)..(732)

<400> SEQUENCE: 119 atg cga cga cga cga cga agc aag ggc gag gaa ctg ttc act ggc gtg      48
Met Arg Arg Arg Arg Arg Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80
```

```
gac cat atg aag cag cat gac ttt ttc aag agc gcc atg ccc gag ggc      288
Asp His Met Lys Gln His Asp Phe Phe Lys Ser Ala Met Pro Glu Gly
             85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 120
<211> LENGTH: 243
<212> TYPE: PRT
<213> ORGANISM: Artificial Sequence
<220> FEATURE:
<223> OTHER INFORMATION: Description of Artificial Sequence:
      Pro(CGA)5GFP

<400> SEQUENCE: 120

Met Arg Arg Arg Arg Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125
```

```
Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 121
<211> LENGTH: 732
<212> TYPE: DNA
<213> ORGANISM: Artificial Sequence
<220> FEATURE:
<223> OTHER INFORMATION: Description of Artificial Sequence:
      Ser(AGC)5GFP
<220> FEATURE:
<221> NAME/KEY: CDS
<222> LOCATION: (1)..(732)

<400> SEQUENCE: 121 atg agc agc agc agc agc agc aag ggc gag gaa ctg ttc act ggc gtg        48
Met Ser Ser Ser Ser Ser Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
```

```
                       165                  170                    175
gag gat gga tcc gtg cag ctg gcc gac cat tat caa cag aac act cca          576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc          624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc          672
Gln Ser Ala Leu Ser Lys Asp Pro Asn Glu Lys Arg Asp His Met Val
        210                 215                 220 ctg ctg gag ttt gtg acc gct gct ggg atc aca cat ggc atg gac gag          720
Leu Leu Glu Phe Val Thr Ala Ala Gly Ile Thr His Gly Met Asp Glu
225                 230                 235                 240 ctg tac aag tga                                                          732
Leu Tyr Lys <210> SEQ ID NO 122
<211> LENGTH: 243
<212> TYPE: PRT
<213> ORGANISM: Artificial Sequence
<220> FEATURE:
<223> OTHER INFORMATION: Description of Artificial Sequence:
      Ser(AGC)5GFP

<400> SEQUENCE: 122

Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 123
<211> LENGTH: 732
<212> TYPE: DNA
<213> ORGANISM: Artificial Sequence
<220> FEATURE:
<223> OTHER INFORMATION: Description of Artificial Sequence: Ser(AGT)5GFP
<220> FEATURE:
<221> NAME/KEY: CDS
<222> LOCATION: (1)..(732)

<400> SEQUENCE: 123

| | | | | | | | | | | | | | | | | |
|---|---|---|---|---|---|---|---|---|---|---|---|---|---|---|---|---|
| atg | agt | agt | agt | agt | agt | agc | aag | ggc | gag | gaa | ctg | ttc | act | ggc | gtg | 48 |
| Met | Ser | Ser | Ser | Ser | Ser | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | | 20 | | | | | 25 | | | | | 30 | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | | 35 | | | | | 40 | | | | | 45 | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| | 50 | | | | | 55 | | | | | 60 | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | | 70 | | | | | 75 | | | | | 80 | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | | 180 | | | | | 185 | | | | | 190 | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | | 195 | | | | | 200 | | | | | 205 | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| | 210 | | | | | 215 | | | | | 220 | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | | 230 | | | | | 235 | | | | | 240 | |
| ctg | tac | aag | tga | | | | | | | | | | | | | 732 |
| Leu | Tyr | Lys | | | | | | | | | | | | | | |

<210> SEQ ID NO 124

<211> LENGTH: 243
<212> TYPE: PRT
<213> ORGANISM: Artificial Sequence
<220> FEATURE:
<223> OTHER INFORMATION: Description of Artificial Sequence:
      Ser(AGT)5GFP

<400> SEQUENCE: 124

Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 125
<211> LENGTH: 732
<212> TYPE: DNA
<213> ORGANISM: Artificial Sequence
<220> FEATURE:
<223> OTHER INFORMATION: Description of Artificial Sequence:
      Ser(TCA)5GFP
<220> FEATURE:
<221> NAME/KEY: CDS
<222> LOCATION: (1)..(732)

<400> SEQUENCE: 125 atg tca tca tca tca tca agc aag ggc gag gaa ctg ttc act ggc gtg      48
Met Ser Ser Ser Ser Ser Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144

```
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 126
<211> LENGTH: 243
<212> TYPE: PRT
<213> ORGANISM: Artificial Sequence
<220> FEATURE:
<223> OTHER INFORMATION: Description of Artificial Sequence:
      Ser(TCA)5GFP

<400> SEQUENCE: 126

Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80
```

```
Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 127
<211> LENGTH: 732
<212> TYPE: DNA
<213> ORGANISM: Artificial Sequence
<220> FEATURE:
<223> OTHER INFORMATION: Description of Artificial Sequence:
      Ser(TCC)5GFP
<220> FEATURE:
<221> NAME/KEY: CDS
<222> LOCATION: (1)..(732)

<400> SEQUENCE: 127 atg tcc tcc tcc tcc tcc agc aag ggc gag gaa ctg ttc act ggc gtg      48
Met Ser Ser Ser Ser Ser Ser Lys Gly Glu Glu Leu Phe Thr Gly Val
  1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
            115                 120                 125
```

```
gag ctg aag ggc att gac ttt aag gag gat gga aac att ctc ggc cac        432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                         732
Leu Tyr Lys <210> SEQ ID NO 128
<211> LENGTH: 243
<212> TYPE: PRT
<213> ORGANISM: Artificial Sequence
<220> FEATURE:
<223> OTHER INFORMATION: Description of Artificial Sequence:
      Ser(TCC)5GFP

<400> SEQUENCE: 128

Met Ser Ser Ser Ser Ser Lys Gly Glu Glu Leu Phe Thr Gly Val
1               5                   10                  15

Val Pro Ile Leu Val Glu Leu Asp Gly Asp Val Asn Gly His Lys Phe
            20                  25                  30

Ser Val Ser Gly Glu Gly Glu Gly Asp Ala Thr Tyr Gly Lys Leu Thr
        35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
```

```
            195                 200                 205
Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 129
<211> LENGTH: 732
<212> TYPE: DNA
<213> ORGANISM: Artificial Sequence
<220> FEATURE:
<223> OTHER INFORMATION: Description of Artificial Sequence:
      Ser(TCG)5GFP
<220> FEATURE:
<221> NAME/KEY: CDS
<222> LOCATION: (1)..(732)

<400> SEQUENCE: 129 atg tcg tcg tcg tcg tcg agc aag ggc gag gaa ctg ttc act ggc gtg      48
Met Ser Ser Ser Ser Ser Ser Lys Gly Glu Glu Leu Phe Thr Gly Val
1               5                   10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220
```

```
ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                     732
Leu Tyr Lys
```

<210> SEQ ID NO 130
<211> LENGTH: 243
<212> TYPE: PRT
<213> ORGANISM: Artificial Sequence
<220> FEATURE:
<223> OTHER INFORMATION: Description of Artificial Sequence:
      Ser(TCG)5GFP

<400> SEQUENCE: 130

```
Met Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 131
<211> LENGTH: 732
<212> TYPE: DNA
<213> ORGANISM: Artificial Sequence
<220> FEATURE:
<223> OTHER INFORMATION: Description of Artificial Sequence:
      Ser(TCT)5GFP
<220> FEATURE:
<221> NAME/KEY: CDS
<222> LOCATION: (1)..(732)

<400> SEQUENCE: 131

```
atg tct tct tct tct tct agc aag ggc gag gaa ctg ttc act ggc gtg        48
Met Ser Ser Ser Ser Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
             100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
         115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys
```

<210> SEQ ID NO 132
<211> LENGTH: 243
<212> TYPE: PRT
<213> ORGANISM: Artificial Sequence
<220> FEATURE:
<223> OTHER INFORMATION: Description of Artificial Sequence:
      Ser(TCT)5GFP

<400> SEQUENCE: 132

Met Ser Ser Ser Ser Ser Ser Lys Gly Glu Glu Leu Phe Thr Gly Val
 1               5                  10                  15

Val Pro Ile Leu Val Glu Leu Asp Gly Asp Val Asn Gly His Lys Phe

```
                        20                  25                  30
Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
 50                      55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                     85                  90                  95

Tyr Val Gln Glu Arg Thr Ile Phe Phe Lys Asp Asp Gly Asn Tyr Lys
                100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 133
<211> LENGTH: 732
<212> TYPE: DNA
<213> ORGANISM: Artificial Sequence
<220> FEATURE:
<223> OTHER INFORMATION: Description of Artificial Sequence:
      Thr(ACA)5GFP
<220> FEATURE:
<221> NAME/KEY: CDS
<222> LOCATION: (1)..(732)

<400> SEQUENCE: 133

```
atg aca aca aca aca aca agc aag ggc gag gaa ctg ttc act ggc gtg         48
Met Thr Thr Thr Thr Thr Ser Lys Gly Glu Glu Leu Phe Thr Gly Val
 1               5                  10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
```

|  |  |  |  |  |  |  |  |  |  |  |  |  | | |
|---|---|---|---|---|---|---|---|---|---|---|---|---|---|---|
| | | | 85 | | | | 90 | | | | 95 | | | |
| tat | gtg | cag | gag | aga | acc | atc | ttt | ttc | aaa | gat | gac | ggg | aac tac aag | 336 |
| Tyr | Val | Gln | Glu | Arg | Thr | Ile | Phe | Phe | Lys | Asp | Asp | Gly | Asn Tyr Lys | |
| | | | 100 | | | | 105 | | | | 110 | | | |
| acc | cgc | gct | gaa | gtc | aag | ttc | gaa | ggt | gac | acc | ctg | gtg | aat aga atc | 384 |
| Thr | Arg | Ala | Glu | Val | Lys | Phe | Glu | Gly | Asp | Thr | Leu | Val | Asn Arg Ile | |
| | | | 115 | | | | 120 | | | | 125 | | | |
| gag | ctg | aag | ggc | att | gac | ttt | aag | gag | gat | gga | aac | att | ctc ggc cac | 432 |
| Glu | Leu | Lys | Gly | Ile | Asp | Phe | Lys | Glu | Asp | Gly | Asn | Ile | Leu Gly His | |
| | | 130 | | | | | 135 | | | | 140 | | | |
| aag | ctg | gaa | tac | aac | tat | aac | tcc | cac | aat | gtg | tac | atc | atg gcc gac | 480 |
| Lys | Leu | Glu | Tyr | Asn | Tyr | Asn | Ser | His | Asn | Val | Tyr | Ile | Met Ala Asp | |
| 145 | | | | | 150 | | | | 155 | | | | 160 | |
| aag | caa | aag | aat | ggc | atc | aag | gtc | aac | ttc | aag | atc | aga | cac aac att | 528 |
| Lys | Gln | Lys | Asn | Gly | Ile | Lys | Val | Asn | Phe | Lys | Ile | Arg | His Asn Ile | |
| | | | | 165 | | | | 170 | | | | | 175 | |
| gag | gat | gga | tcc | gtg | cag | ctg | gcc | gac | cat | tat | caa | cag | aac act cca | 576 |
| Glu | Asp | Gly | Ser | Val | Gln | Leu | Ala | Asp | His | Tyr | Gln | Gln | Asn Thr Pro | |
| | | | 180 | | | | | 185 | | | | 190 | | |
| atc | ggc | gac | ggc | cct | gtg | ctc | ctc | cca | gac | aac | cat | tac | ctg tcc acc | 624 |
| Ile | Gly | Asp | Gly | Pro | Val | Leu | Leu | Pro | Asp | Asn | His | Tyr | Leu Ser Thr | |
| | | | 195 | | | | 200 | | | | | 205 | | |
| cag | tct | gcc | ctg | tct | aaa | gat | ccc | aac | gaa | aag | aga | gac | cac atg gtc | 672 |
| Gln | Ser | Ala | Leu | Ser | Lys | Asp | Pro | Asn | Glu | Lys | Arg | Asp | His Met Val | |
| 210 | | | | | 215 | | | | | 220 | | | | |
| ctg | ctg | gag | ttt | gtg | acc | gct | gct | ggg | atc | aca | cat | ggc | atg gac gag | 720 |
| Leu | Leu | Glu | Phe | Val | Thr | Ala | Ala | Gly | Ile | Thr | His | Gly | Met Asp Glu | |
| 225 | | | | 230 | | | | | 235 | | | | 240 | |
| ctg | tac | aag | tga | | | | | | | | | | | 732 |
| Leu | Tyr | Lys | | | | | | | | | | | | |

<210> SEQ ID NO 134
<211> LENGTH: 243
<212> TYPE: PRT
<213> ORGANISM: Artificial Sequence
<220> FEATURE:
<223> OTHER INFORMATION: Description of Artificial Sequence:
    Thr(ACA)5GFP

<400> SEQUENCE: 134

Met Thr Thr Thr Thr Thr Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

```
Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
            165                 170                 175

Glu Asp Gly Ser Val Gln Leu Ala Asp His Tyr Gln Gln Asn Thr Pro
        180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 135
<211> LENGTH: 732
<212> TYPE: DNA
<213> ORGANISM: Artificial Sequence
<220> FEATURE:
<223> OTHER INFORMATION: Description of Artificial Sequence:
      Thr(ACC)5GFP
<220> FEATURE:
<221> NAME/KEY: CDS
<222> LOCATION: (1)..(732)

<400> SEQUENCE: 135 atg acc acc acc acc acc agc aag ggc gag gaa ctg ttc act ggc gtg        48
Met Thr Thr Thr Thr Thr Ser Lys Gly Glu Glu Leu Phe Thr Gly Val
 1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca       576
```

```
                                          Glu Asp Gly Ser Val Gln Leu Ala Asp His Tyr Gln Gln Asn Thr Pro
                                                          180                 185                 190 atc ggc gac ggc cct gtg ctc ctc cca gac aac cat tac ctg tcc acc            624
Ile Gly Asp Gly Pro Val Leu Leu Pro Asp Asn His Tyr Leu Ser Thr
                195                 200                 205 cag tct gcc ctg tct aaa gat ccc aac gaa aag aga gac cac atg gtc            672
Gln Ser Ala Leu Ser Lys Asp Pro Asn Glu Lys Arg Asp His Met Val
        210                 215                 220 ctg ctg gag ttt gtg acc gct gct ggg atc aca cat ggc atg gac gag            720
Leu Leu Glu Phe Val Thr Ala Ala Gly Ile Thr His Gly Met Asp Glu
225                 230                 235                 240 ctg tac aag tga                                                            732
Leu Tyr Lys
```

<210> SEQ ID NO 136
<211> LENGTH: 243
<212> TYPE: PRT
<213> ORGANISM: Artificial Sequence
<220> FEATURE:
<223> OTHER INFORMATION: Description of Artificial Sequence:
      Thr(ACC)5GFP

<400> SEQUENCE: 136

```
Met Thr Thr Thr Thr Thr Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
     65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 137
<211> LENGTH: 732

```
<212> TYPE: DNA
<213> ORGANISM: Artificial Sequence
<220> FEATURE:
<223> OTHER INFORMATION: Description of Artificial Sequence:
      Thr(ACG)5GFP
<220> FEATURE:
<221> NAME/KEY: CDS
<222> LOCATION: (1)..(732)

<400> SEQUENCE: 137 atg acg acg acg acg acg agc aag ggc gag gaa ctg ttc act ggc gtg      48
Met Thr Thr Thr Thr Thr Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
225                 230                 235                 240 ctg tac aag tga                                                     732
Leu Tyr Lys <210> SEQ ID NO 138
<211> LENGTH: 243
<212> TYPE: PRT
<213> ORGANISM: Artificial Sequence
```

-continued

```
<220> FEATURE:
<223> OTHER INFORMATION: Description of Artificial Sequence:
      Thr(ACG)5GFP

<400> SEQUENCE: 138

Met Thr Thr Thr Thr Thr Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 139
<211> LENGTH: 732
<212> TYPE: DNA
<213> ORGANISM: Artificial Sequence
<220> FEATURE:
<223> OTHER INFORMATION: Description of Artificial Sequence:
      Thr(ACT)5GFP
<220> FEATURE:
<221> NAME/KEY: CDS
<222> LOCATION: (1)..(732)

<400> SEQUENCE: 139 atg act act act act act agc aag ggc gag gaa ctg ttc act ggc gtg     48
Met Thr Thr Thr Thr Thr Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45
```

```
ctg aaa ttc atc tgc acc act gga aag ctc cct gtg cca tgg cca aca      192
Leu Lys Phe Ile Cys Thr Thr Gly Lys Leu Pro Val Pro Trp Pro Thr
        50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                     85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
                100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
        130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att      528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca      576
Glu Asp Gly Ser Val Gln Leu Ala Asp His Tyr Gln Gln Asn Thr Pro
                180                 185                 190 atc ggc gac ggc cct gtg ctc ctc cca gac aac cat tac ctg tcc acc      624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc      672
Gln Ser Ala Leu Ser Lys Asp Pro Asn Glu Lys Arg Asp His Met Val
        210                 215                 220 ctg ctg gag ttt gtg acc gct gct ggg atc aca cat ggc atg gac gag      720
Leu Leu Glu Phe Val Thr Ala Ala Gly Ile Thr His Gly Met Asp Glu
225                 230                 235                 240 ctg tac aag tga                                                      732
Leu Tyr Lys <210> SEQ ID NO 140
<211> LENGTH: 243
<212> TYPE: PRT
<213> ORGANISM: Artificial Sequence
<220> FEATURE:
<223> OTHER INFORMATION: Description of Artificial Sequence:
      Thr(ACT)5GFP

<400> SEQUENCE: 140

Met Thr Thr Thr Thr Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                     85                  90                  95
```

```
Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
        130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 141
<211> LENGTH: 732
<212> TYPE: DNA
<213> ORGANISM: Artificial Sequence
<220> FEATURE:
<223> OTHER INFORMATION: Description of Artificial Sequence:
      Trp(TGG)5GFP
<220> FEATURE:
<221> NAME/KEY: CDS
<222> LOCATION: (1)..(732)

<400> SEQUENCE: 141 atg tgg tgg tgg tgg tgg agc aag ggc gag gaa ctg ttc act ggc gtg        48
Met Trp Trp Trp Trp Trp Ser Lys Gly Glu Glu Leu Phe Thr Gly Val
  1               5                  10                  15 gtc cca att ctc gtg gaa ctg gat ggc gat gtg aat ggg cac aaa ttt        96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
    130                 135                 140
```

```
aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 142
<211> LENGTH: 243
<212> TYPE: PRT
<213> ORGANISM: Artificial Sequence
<220> FEATURE:
<223> OTHER INFORMATION: Description of Artificial Sequence:
      Trp(TGG)5GFP

<400> SEQUENCE: 142

Met Trp Trp Trp Trp Trp Ser Lys Gly Glu Glu Leu Phe Thr Gly Val
1               5                   10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
            165                 170                 175

Glu Asp Gly Ser Val Gln Leu Ala Asp His Tyr Gln Gln Asn Thr Pro
        180                 185                 190

Ile Gly Asp Gly Pro Val Leu Leu Pro Asp Asn His Tyr Leu Ser Thr
    195                 200                 205

Gln Ser Ala Leu Ser Lys Asp Pro Asn Glu Lys Arg Asp His Met Val
```

```
                210             215             220
Leu Leu Glu Phe Val Thr Ala Ala Gly Ile Thr His Gly Met Asp Glu
225                 230                 235                 240

Leu Tyr Lys

<210> SEQ ID NO 143
<211> LENGTH: 732
<212> TYPE: DNA
<213> ORGANISM: Artificial Sequence
<220> FEATURE:
<223> OTHER INFORMATION: Description of Artificial Sequence:
      Tyr(TAT)5GFP
<220> FEATURE:
<221> NAME/KEY: CDS
<222> LOCATION: (1)..(732)

<400> SEQUENCE: 143 atg tat tat tat tat tat agc aag ggc gag gaa ctg ttc act ggc gtg      48
Met Tyr Tyr Tyr Tyr Tyr Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc     624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc     672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag     720
Leu Leu Glu Phe Val Thr Ala Ala Gly Ile Thr His Gly Met Asp Glu
```

-continued

```
                225                 230                 235                 240 ctg tac aag tga                                                                          732
Leu Tyr Lys
```

<210> SEQ ID NO 144
<211> LENGTH: 243
<212> TYPE: PRT
<213> ORGANISM: Artificial Sequence
<220> FEATURE:
<223> OTHER INFORMATION: Description of Artificial Sequence:
      Tyr(TAT)5GFP

<400> SEQUENCE: 144

```
Met Tyr Tyr Tyr Tyr Tyr Ser Lys Gly Glu Glu Leu Phe Thr Gly Val
  1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
     50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 145
<211> LENGTH: 732
<212> TYPE: DNA
<213> ORGANISM: Artificial Sequence
<220> FEATURE:
<223> OTHER INFORMATION: Description of Artificial Sequence:
      Tyr(TAC)5GFP
<220> FEATURE:
<221> NAME/KEY: CDS
<222> LOCATION: (1)..(732)

<400> SEQUENCE: 145

```
atg tac tac tac tac tac agc aag ggc gag gaa ctg ttc act ggc gtg     48
Met Tyr Tyr Tyr Tyr Tyr Ser Lys Gly Glu Glu Leu Phe Thr Gly Val
```

```
            1               5                   10                  15
gtc cca att ctc gtg gaa ctg gat ggc gat gtg aat ggg cac aaa ttt        96
Val Pro Ile Leu Val Glu Leu Asp Gly Asp Val Asn Gly His Lys Phe
                    20                  25                  30 tct gtc agc gga gag ggt gaa ggt gat gcc aca tac gga aag ctc acc       144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca       192
Leu Lys Phe Ile Cys Thr Thr Gly Lys Leu Pro Val Pro Trp Pro Thr
    50                  55                  60 ctg gtc act acc ttc tct tat ggc gtg cag tgc ttt tcc aga tac cca       240
Leu Val Thr Thr Phe Ser Tyr Gly Val Gln Cys Phe Ser Arg Tyr Pro
65                  70                  75                  80 gac cat atg aag cag cat gac ttt ttc aag agc gcc atg ccc gag ggc       288
Asp His Met Lys Gln His Asp Phe Phe Lys Ser Ala Met Pro Glu Gly
                    85                  90                  95 tat gtg cag gag aga acc atc ttt ttc aaa gat gac ggg aac tac aag       336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc       384
Thr Arg Ala Glu Val Lys Phe Glu Gly Asp Thr Leu Val Asn Arg Ile
    115                 120                 125 gag ctg aag ggc att gac ttt aag gag gat gga aac att ctc ggc cac       432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac       480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att       528
Lys Gln Lys Asn Gly Ile Lys Val Asn Phe Lys Ile Arg His Asn Ile
                    165                 170                 175 gag gat gga tcc gtg cag ctg gcc gac cat tat caa cag aac act cca       576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc       624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc       672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag       720
Leu Leu Glu Phe Val Thr Ala Ala Gly Ile Thr His Gly Met Asp Glu
225                 230                 235                 240 ctg tac aag tga                                                       732
Leu Tyr Lys <210> SEQ ID NO 146
<211> LENGTH: 243
<212> TYPE: PRT
<213> ORGANISM: Artificial Sequence
<220> FEATURE:
<223> OTHER INFORMATION: Description of Artificial Sequence:
      Tyr(TAC)5GFP

<400> SEQUENCE: 146

Met Tyr Tyr Tyr Tyr Ser Lys Gly Glu Glu Leu Phe Thr Gly Val
 1               5                   10                  15

Val Pro Ile Leu Val Glu Leu Asp Gly Asp Val Asn Gly His Lys Phe
                    20                  25                  30

Ser Val Ser Gly Glu Gly Glu Gly Asp Ala Thr Tyr Gly Lys Leu Thr
```

```
                35                  40                  45
Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 147
<211> LENGTH: 732
<212> TYPE: DNA
<213> ORGANISM: Artificial Sequence
<220> FEATURE:
<223> OTHER INFORMATION: Description of Artificial Sequence:
      Val(GTA)5GFP
<220> FEATURE:
<221> NAME/KEY: CDS
<222> LOCATION: (1)..(732)

<400> SEQUENCE: 147 atg gta gta gta gta gta agc aag ggc gag gaa ctg ttc act ggc gtg    48
Met Val Val Val Val Val Ser Lys Gly Glu Glu Leu Phe Thr Gly Val
  1               5                  10                  15 gtc cca att ctc gtg gaa ctg gat ggc gat gtg aat ggg cac aaa ttt    96
Val Pro Ile Leu Val Glu Leu Asp Gly Asp Val Asn Gly His Lys Phe
                 20                  25                  30 tct gtc agc gga gag ggt gaa ggt gat gcc aca tac gga aag ctc acc   144
Ser Val Ser Gly Glu Gly Glu Gly Asp Ala Thr Tyr Gly Lys Leu Thr
             35                  40                  45 ctg aaa ttc atc tgc acc act gga aag ctc cct gtg cca tgg cca aca   192
Leu Lys Phe Ile Cys Thr Thr Gly Lys Leu Pro Val Pro Trp Pro Thr
         50                  55                  60 ctg gtc act acc ttc tct tat ggc gtg cag tgc ttt tcc aga tac cca   240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc   288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag   336
Tyr Val Gln Glu Arg Thr Ile Phe Phe Lys Asp Asp Gly Asn Tyr Lys
```

```
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc    384
Thr Arg Ala Glu Val Lys Phe Glu Gly Asp Thr Leu Val Asn Arg Ile
            115                 120                 125 gag ctg aag ggc att gac ttt aag gag gat gga aac att ctc ggc cac    432
Glu Leu Lys Gly Ile Asp Phe Lys Glu Asp Gly Asn Ile Leu Gly His
130                 135                 140 aag ctg gaa tac aac tat aac tcc cac aat gtg tac atc atg gcc gac    480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att    528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca    576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc    624
Ile Gly Asp Gly Pro Val Leu Leu Pro Asp Asn His Tyr Leu Ser Thr
            195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys <210> SEQ ID NO 148
<211> LENGTH: 243
<212> TYPE: PRT
<213> ORGANISM: Artificial Sequence
<220> FEATURE:
<223> OTHER INFORMATION: Description of Artificial Sequence:
      Val(GTA)5GFP

<400> SEQUENCE: 148

Met Val Val Val Val Ser Lys Gly Glu Glu Leu Phe Thr Gly Val
  1               5                  10                  15

Val Pro Ile Leu Val Glu Leu Asp Gly Asp Val Asn Gly His Lys Phe
                 20                  25                  30

Ser Val Ser Gly Glu Gly Glu Gly Asp Ala Thr Tyr Gly Lys Leu Thr
             35                  40                  45

Leu Lys Phe Ile Cys Thr Thr Gly Lys Leu Pro Val Pro Trp Pro Thr
         50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
            115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160
```

-continued

```
Lys Gln Lys Asn Gly Ile Lys Val Asn Phe Lys Ile Arg His Asn Ile
            165                 170                 175

Glu Asp Gly Ser Val Gln Leu Ala Asp His Tyr Gln Gln Asn Thr Pro
        180                 185                 190

Ile Gly Asp Gly Pro Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys
```

<210> SEQ ID NO 149
<211> LENGTH: 732
<212> TYPE: DNA
<213> ORGANISM: Artificial Sequence
<220> FEATURE:
<223> OTHER INFORMATION: Description of Artificial Sequence:
      Val(GTC)5GFP
<220> FEATURE:
<221> NAME/KEY: CDS
<222> LOCATION: (1)..(732)

<400> SEQUENCE: 149

```
atg gtc gtc gtc gtc gtc agc aag ggc gag gaa ctg ttc act ggc gtg      48
Met Val Val Val Val Val Ser Lys Gly Glu Glu Leu Phe Thr Gly Val
 1               5                  10                  15 gtc cca att ctc gtg gaa ctg gat ggc gat gtg aat ggg cac aaa ttt      96
Val Pro Ile Leu Val Glu Leu Asp Gly Asp Val Asn Gly His Lys Phe
                20                  25                  30 tct gtc agc gga gag ggt gaa ggt gat gcc aca tac gga aag ctc acc     144
Ser Val Ser Gly Glu Gly Glu Gly Asp Ala Thr Tyr Gly Lys Leu Thr
            35                  40                  45 ctg aaa ttc atc tgc acc act gga aag ctc cct gtg cca tgg cca aca     192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca     240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc     288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag     336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc     384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac     432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac     480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att     528
Lys Gln Lys Asn Gly Ile Lys Val Asn Phe Lys Ile Arg His Asn Ile
                165                 170                 175 gag gat gga tcc gtg cag ctg gcc gac cat tat caa cag aac act cca     576
Glu Asp Gly Ser Val Gln Leu Ala Asp His Tyr Gln Gln Asn Thr Pro
            180                 185                 190
```

```
atc ggc gac ggc cct gtg ctc ctc cca gac aac cat tac ctg tcc acc    624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc    672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag    720
Leu Leu Glu Phe Val Thr Ala Ala Gly Ile Thr His Gly Met Asp Glu
225                 230                 235                 240 ctg tac aag tga                                                    732
Leu Tyr Lys
```

<210> SEQ ID NO 150
<211> LENGTH: 243
<212> TYPE: PRT
<213> ORGANISM: Artificial Sequence
<220> FEATURE:
<223> OTHER INFORMATION: Description of Artificial Sequence:
      Val(GTC)5GFP

<400> SEQUENCE: 150

```
Met Val Val Val Val Ser Lys Gly Glu Glu Leu Phe Thr Gly Val
 1               5                  10                  15

Val Pro Ile Leu Val Glu Leu Asp Gly Asp Val Asn Gly His Lys Phe
                20                  25                  30

Ser Val Ser Gly Glu Gly Glu Gly Asp Ala Thr Tyr Gly Lys Leu Thr
            35                  40                  45

Leu Lys Phe Ile Cys Thr Thr Gly Lys Leu Pro Val Pro Trp Pro Thr
    50                  55                  60

Leu Val Thr Thr Phe Ser Tyr Gly Val Gln Cys Phe Ser Arg Tyr Pro
65                  70                  75                  80

Asp His Met Lys Gln His Asp Phe Phe Lys Ser Ala Met Pro Glu Gly
                85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
    130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 151
<211> LENGTH: 732
<212> TYPE: DNA
<213> ORGANISM: Artificial Sequence
<220> FEATURE:

<223> OTHER INFORMATION: Description of Artificial Sequence:
      Val(GTG)5GFP
<220> FEATURE:
<221> NAME/KEY: CDS
<222> LOCATION: (1)..(732)

<400> SEQUENCE: 151

| | | | | | | | | | | | | | | | | |
|---|---|---|---|---|---|---|---|---|---|---|---|---|---|---|---|---|
| atg | gtg | gtg | gtg | gtg | gtg | agc | aag | ggc | gag | gaa | ctg | ttc | act | ggc | gtg | 48 |
| Met | Val | Val | Val | Val | Val | Ser | Lys | Gly | Glu | Glu | Leu | Phe | Thr | Gly | Val | |
| 1 | | | | 5 | | | | | 10 | | | | | 15 | | |
| gtc | cca | att | ctc | gtg | gaa | ctg | gat | ggc | gat | gtg | aat | ggg | cac | aaa | ttt | 96 |
| Val | Pro | Ile | Leu | Val | Glu | Leu | Asp | Gly | Asp | Val | Asn | Gly | His | Lys | Phe | |
| | | | 20 | | | | | 25 | | | | | 30 | | | |
| tct | gtc | agc | gga | gag | ggt | gaa | ggt | gat | gcc | aca | tac | gga | aag | ctc | acc | 144 |
| Ser | Val | Ser | Gly | Glu | Gly | Glu | Gly | Asp | Ala | Thr | Tyr | Gly | Lys | Leu | Thr | |
| | 35 | | | | | 40 | | | | | 45 | | | | | |
| ctg | aaa | ttc | atc | tgc | acc | act | gga | aag | ctc | cct | gtg | cca | tgg | cca | aca | 192 |
| Leu | Lys | Phe | Ile | Cys | Thr | Thr | Gly | Lys | Leu | Pro | Val | Pro | Trp | Pro | Thr | |
| 50 | | | | | 55 | | | | | 60 | | | | | | |
| ctg | gtc | act | acc | ttc | tct | tat | ggc | gtg | cag | tgc | ttt | tcc | aga | tac | cca | 240 |
| Leu | Val | Thr | Thr | Phe | Ser | Tyr | Gly | Val | Gln | Cys | Phe | Ser | Arg | Tyr | Pro | |
| 65 | | | | 70 | | | | | 75 | | | | | 80 | | |
| gac | cat | atg | aag | cag | cat | gac | ttt | ttc | aag | agc | gcc | atg | ccc | gag | ggc | 288 |
| Asp | His | Met | Lys | Gln | His | Asp | Phe | Phe | Lys | Ser | Ala | Met | Pro | Glu | Gly | |
| | | | | 85 | | | | | 90 | | | | | 95 | | |
| tat | gtg | cag | gag | aga | acc | atc | ttt | ttc | aaa | gat | gac | ggg | aac | tac | aag | 336 |
| Tyr | Val | Gln | Glu | Arg | Thr | Ile | Phe | Phe | Lys | Asp | Asp | Gly | Asn | Tyr | Lys | |
| | | | 100 | | | | | 105 | | | | | 110 | | | |
| acc | cgc | gct | gaa | gtc | aag | ttc | gaa | ggt | gac | acc | ctg | gtg | aat | aga | atc | 384 |
| Thr | Arg | Ala | Glu | Val | Lys | Phe | Glu | Gly | Asp | Thr | Leu | Val | Asn | Arg | Ile | |
| | | 115 | | | | | 120 | | | | | 125 | | | | |
| gag | ctg | aag | ggc | att | gac | ttt | aag | gag | gat | gga | aac | att | ctc | ggc | cac | 432 |
| Glu | Leu | Lys | Gly | Ile | Asp | Phe | Lys | Glu | Asp | Gly | Asn | Ile | Leu | Gly | His | |
| | 130 | | | | | 135 | | | | | 140 | | | | | |
| aag | ctg | gaa | tac | aac | tat | aac | tcc | cac | aat | gtg | tac | atc | atg | gcc | gac | 480 |
| Lys | Leu | Glu | Tyr | Asn | Tyr | Asn | Ser | His | Asn | Val | Tyr | Ile | Met | Ala | Asp | |
| 145 | | | | | 150 | | | | | 155 | | | | | 160 | |
| aag | caa | aag | aat | ggc | atc | aag | gtc | aac | ttc | aag | atc | aga | cac | aac | att | 528 |
| Lys | Gln | Lys | Asn | Gly | Ile | Lys | Val | Asn | Phe | Lys | Ile | Arg | His | Asn | Ile | |
| | | | | 165 | | | | | 170 | | | | | 175 | | |
| gag | gat | gga | tcc | gtg | cag | ctg | gcc | gac | cat | tat | caa | cag | aac | act | cca | 576 |
| Glu | Asp | Gly | Ser | Val | Gln | Leu | Ala | Asp | His | Tyr | Gln | Gln | Asn | Thr | Pro | |
| | | 180 | | | | | 185 | | | | | 190 | | | | |
| atc | ggc | gac | ggc | cct | gtg | ctc | ctc | cca | gac | aac | cat | tac | ctg | tcc | acc | 624 |
| Ile | Gly | Asp | Gly | Pro | Val | Leu | Leu | Pro | Asp | Asn | His | Tyr | Leu | Ser | Thr | |
| | 195 | | | | | 200 | | | | | 205 | | | | | |
| cag | tct | gcc | ctg | tct | aaa | gat | ccc | aac | gaa | aag | aga | gac | cac | atg | gtc | 672 |
| Gln | Ser | Ala | Leu | Ser | Lys | Asp | Pro | Asn | Glu | Lys | Arg | Asp | His | Met | Val | |
| 210 | | | | | 215 | | | | | 220 | | | | | | |
| ctg | ctg | gag | ttt | gtg | acc | gct | gct | ggg | atc | aca | cat | ggc | atg | gac | gag | 720 |
| Leu | Leu | Glu | Phe | Val | Thr | Ala | Ala | Gly | Ile | Thr | His | Gly | Met | Asp | Glu | |
| 225 | | | | 230 | | | | | 235 | | | | | 240 | | |
| ctg | tac | aag | tga | | | | | | | | | | | | | 732 |
| Leu | Tyr | Lys | | | | | | | | | | | | | | |

<210> SEQ ID NO 152
<211> LENGTH: 243
<212> TYPE: PRT
<213> ORGANISM: Artificial Sequence
<220> FEATURE:
<223> OTHER INFORMATION: Description of Artificial Sequence:
      Val(GTG)5GFP -continued

```
<400> SEQUENCE: 152

Met Val Val Val Val Ser Lys Gly Glu Glu Leu Phe Thr Gly Val
 1               5                  10                  15

Val Pro Ile Leu Val Glu Leu Asp Gly Asp Val Asn Gly His Lys Phe
             20                  25                  30

Ser Val Ser Gly Glu Gly Glu Gly Asp Ala Thr Tyr Gly Lys Leu Thr
         35                  40                  45

Leu Lys Phe Ile Cys Thr Thr Gly Lys Leu Pro Val Pro Trp Pro Thr
 50                  55                  60

Leu Val Thr Thr Phe Ser Tyr Gly Val Gln Cys Phe Ser Arg Tyr Pro
 65                  70                  75                  80

Asp His Met Lys Gln His Asp Phe Phe Lys Ser Ala Met Pro Glu Gly
                 85                  90                  95

Tyr Val Gln Glu Arg Thr Ile Phe Phe Lys Asp Asp Gly Asn Tyr Lys
            100                 105                 110

Thr Arg Ala Glu Val Lys Phe Glu Gly Asp Thr Leu Val Asn Arg Ile
        115                 120                 125

Glu Leu Lys Gly Ile Asp Phe Lys Glu Asp Gly Asn Ile Leu Gly His
130                 135                 140

Lys Leu Glu Tyr Asn Tyr Asn Ser His Asn Val Tyr Ile Met Ala Asp
145                 150                 155                 160

Lys Gln Lys Asn Gly Ile Lys Val Asn Phe Lys Ile Arg His Asn Ile
                165                 170                 175

Glu Asp Gly Ser Val Gln Leu Ala Asp His Tyr Gln Gln Asn Thr Pro
            180                 185                 190

Ile Gly Asp Gly Pro Val Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 153
<211> LENGTH: 732
<212> TYPE: DNA
<213> ORGANISM: Artificial Sequence
<220> FEATURE:
<223> OTHER INFORMATION: Description of Artificial Sequence:
      Val(GTT)5GFP
<220> FEATURE:
<221> NAME/KEY: CDS
<222> LOCATION: (1)..(732)

<400> SEQUENCE: 153 atg gtt gtt gtt gtt gtt agc aag ggc gag gaa ctg ttc act ggc gtg     48
Met Val Val Val Val Val Ser Lys Gly Glu Glu Leu Phe Thr Gly Val
 1               5                  10                  15 gtc cca att ctc gtg gaa ctg gat ggc gat gtg aat ggg cac aaa ttt     96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc    144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca    192
Leu Lys Phe Ile Cys Thr Thr Gly Lys Leu Pro Val Pro Trp Pro Thr
 50                  55                  60
```

| | | |
|---|---|---|
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                        70                      75                    80 | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                      85                      90                    95 | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>              100                      105                    110 | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>115                      120                      125 | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>    130                      135                    140 | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                      150                      155                    160 | 480 |
| aag caa aag aat ggc atc aag gtc aac ttc aag atc aga cac aac att<br>Lys Gln Lys Asn Gly Ile Lys Val Asn Phe Lys Ile Arg His Asn Ile<br>                165                      170                    175 | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>              180                      185                    190 | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>                195                      200                    205 | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210                      215                      220 | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                      230                      235                    240 | 720 |
| ctg tac aag tga<br>Leu Tyr Lys | 732 |

<210> SEQ ID NO 154
<211> LENGTH: 243
<212> TYPE: PRT
<213> ORGANISM: Artificial Sequence
<220> FEATURE:
<223> OTHER INFORMATION: Description of Artificial Sequence:
      Val(GTT)5GFP

<400> SEQUENCE: 154

Met Val Val Val Val Ser Lys Gly Glu Glu Leu Phe Thr Gly Val
 1               5                    10                    15

Val Pro Ile Leu Val Glu Leu Asp Gly Asp Val Asn Gly His Lys Phe
                20                      25                    30

Ser Val Ser Gly Glu Gly Glu Gly Asp Ala Thr Tyr Gly Lys Leu Thr
          35                      40                    45

Leu Lys Phe Ile Cys Thr Thr Gly Lys Leu Pro Val Pro Trp Pro Thr
    50                      55                    60

Leu Val Thr Thr Phe Ser Tyr Gly Val Gln Cys Phe Ser Arg Tyr Pro
65                        70                      75                    80

Asp His Met Lys Gln His Asp Phe Phe Lys Ser Ala Met Pro Glu Gly
                85                      90                    95

Tyr Val Gln Glu Arg Thr Ile Phe Phe Lys Asp Asp Gly Asn Tyr Lys
              100                      105                    110

```
Thr Arg Ala Glu Val Lys Phe Glu Gly Asp Thr Leu Val Asn Arg Ile
        115                 120                 125
Glu Leu Lys Gly Ile Asp Phe Lys Glu Asp Gly Asn Ile Leu Gly His
    130                 135                 140
Lys Leu Glu Tyr Asn Tyr Asn Ser His Asn Val Tyr Ile Met Ala Asp
145                 150                 155                 160
Lys Gln Lys Asn Gly Ile Lys Val Asn Phe Lys Ile Arg His Asn Ile
                165                 170                 175
Glu Asp Gly Ser Val Gln Leu Ala Asp His Tyr Gln Gln Asn Thr Pro
            180                 185                 190
Ile Gly Asp Gly Pro Val Leu Leu Pro Asp Asn His Tyr Leu Ser Thr
        195                 200                 205
Gln Ser Ala Leu Ser Lys Asp Pro Asn Glu Lys Arg Asp His Met Val
    210                 215                 220
Leu Leu Glu Phe Val Thr Ala Ala Gly Ile Thr His Gly Met Asp Glu
225                 230                 235                 240
Leu Tyr Lys

<210> SEQ ID NO 155
<211> LENGTH: 732
<212> TYPE: DNA
<213> ORGANISM: Artificial Sequence
<220> FEATURE:
<223> OTHER INFORMATION: Description of Artificial Sequence:
      Stop(TAA)5GFP
<220> FEATURE:
<221> NAME/KEY: CDS
<222> LOCATION: (1)..(732)

<400> SEQUENCE: 155 atg taa taa taa taa taa agc aag ggc gag gaa ctg ttc act ggc gtg       48
Met             Ser Lys Gly Glu Glu Leu Phe Thr Gly Val
  1           5                  10                  15 gtc cca att ctc gtg gaa ctg gat ggc gat gtg aat ggg cac aaa ttt       96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc      144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca      192
Leu Lys Phe Ile Cys Thr Thr Gly Lys Leu Pro Val Pro Trp Pro Thr
 50                  55                  60 ctg gtc act acc ttc tct tat ggc gtg cag tgc ttt tcc aga tac cca      240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc      288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag      336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc      384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac      432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac      480
Lys Leu Glu Tyr Asn Tyr Asn Ser His Asn Val Tyr Ile Met Ala Asp
```

| | |
|---|---|
| aag caa aag aat ggc atc aag gtc aac ttc aag atc aga cac aac att<br>Lys Gln Lys Asn Gly Ile Lys Val Asn Phe Lys Ile Arg His Asn Ile<br>                            165                      170                    175 | 528 |
| gag gat gga tcc gtg cag ctg gcc gac cat tat caa cag aac act cca<br>Glu Asp Gly Ser Val Gln Leu Ala Asp His Tyr Gln Gln Asn Thr Pro<br>                180                      185                      190 | 576 |
| atc ggc gac ggc cct gtg ctc ctc cca gac aac cat tac ctg tcc acc<br>Ile Gly Asp Gly Pro Val Leu Leu Pro Asp Asn His Tyr Leu Ser Thr<br>         195                      200                      205 | 624 |
| cag tct gcc ctg tct aaa gat ccc aac gaa aag aga gac cac atg gtc<br>Gln Ser Ala Leu Ser Lys Asp Pro Asn Glu Lys Arg Asp His Met Val<br>210                      215                      220 | 672 |
| ctg ctg gag ttt gtg acc gct gct ggg atc aca cat ggc atg gac gag<br>Leu Leu Glu Phe Val Thr Ala Ala Gly Ile Thr His Gly Met Asp Glu<br>225                      230                      235                      240 | 720 |
| ctg tac aag tga<br>Leu Tyr Lys | 732 |

<210> SEQ ID NO 156
<211> LENGTH: 732
<212> TYPE: DNA
<213> ORGANISM: Artificial Sequence
<220> FEATURE:
<223> OTHER INFORMATION: Description of Artificial Sequence:
    Stop(TAG)5GFP
<220> FEATURE:
<221> NAME/KEY: CDS
<222> LOCATION: (1)..(732)

<400> SEQUENCE: 156

| | |
|---|---|
| atg tag tag tag tag tag agc aag ggc gag gaa ctg ttc act ggc gtg<br>Met                                 Ser Lys Gly Glu Glu Leu Phe Thr Gly Val<br>1                  5                      10                      15 | 48 |
| gtc cca att ctc gtg gaa ctg gat ggc gat gtg aat ggg cac aaa ttt<br>Val Pro Ile Leu Val Glu Leu Asp Gly Asp Val Asn Gly His Lys Phe<br>                20                      25                      30 | 96 |
| tct gtc agc gga gag ggt gaa ggt gat gcc aca tac gga aag ctc acc<br>Ser Val Ser Gly Glu Gly Glu Gly Asp Ala Thr Tyr Gly Lys Leu Thr<br>         35                      40                      45 | 144 |
| ctg aaa ttc atc tgc acc act gga aag ctc cct gtg cca tgg cca aca<br>Leu Lys Phe Ile Cys Thr Thr Gly Lys Leu Pro Val Pro Trp Pro Thr<br>50                      55                      60 | 192 |
| ctg gtc act acc ttc tct tat ggc gtg cag tgc ttt tcc aga tac cca<br>Leu Val Thr Thr Phe Ser Tyr Gly Val Gln Cys Phe Ser Arg Tyr Pro<br>65                      70                      75                      80 | 240 |
| gac cat atg aag cag cat gac ttt ttc aag agc gcc atg ccc gag ggc<br>Asp His Met Lys Gln His Asp Phe Phe Lys Ser Ala Met Pro Glu Gly<br>                85                      90                      95 | 288 |
| tat gtg cag gag aga acc atc ttt ttc aaa gat gac ggg aac tac aag<br>Tyr Val Gln Glu Arg Thr Ile Phe Phe Lys Asp Asp Gly Asn Tyr Lys<br>                100                      105                      110 | 336 |
| acc cgc gct gaa gtc aag ttc gaa ggt gac acc ctg gtg aat aga atc<br>Thr Arg Ala Glu Val Lys Phe Glu Gly Asp Thr Leu Val Asn Arg Ile<br>         115                      120                      125 | 384 |
| gag ctg aag ggc att gac ttt aag gag gat gga aac att ctc ggc cac<br>Glu Leu Lys Gly Ile Asp Phe Lys Glu Asp Gly Asn Ile Leu Gly His<br>         130                      135                      140 | 432 |
| aag ctg gaa tac aac tat aac tcc cac aat gtg tac atc atg gcc gac<br>Lys Leu Glu Tyr Asn Tyr Asn Ser His Asn Val Tyr Ile Met Ala Asp<br>145                      150                      155                      160 | 480 |

```
aag caa aag aat ggc atc aag gtc aac ttc aag atc aga cac aac att        528
Lys Gln Lys Asn Gly Ile Lys Val Asn Phe Lys Ile Arg His Asn Ile
            165                 170                 175 gag gat gga tcc gtg cag ctg gcc gac cat tat caa cag aac act cca        576
Glu Asp Gly Ser Val Gln Leu Ala Asp His Tyr Gln Gln Asn Thr Pro
        180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
    195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 157
<211> LENGTH: 732
<212> TYPE: DNA
<213> ORGANISM: Artificial Sequence
<220> FEATURE:
<223> OTHER INFORMATION: Description of Artificial Sequence:
      Stop(TGA)5GFP
<220> FEATURE:
<221> NAME/KEY: CDS
<222> LOCATION: (1)..(732)

<400> SEQUENCE: 157 atg tga tga tga tga tga agc aag ggc gag gaa ctg ttc act ggc gtg         48
Met                     Ser Lys Gly Glu Glu Leu Phe Thr Gly Val
  1               5                  10                  15 gtc cca att ctc gtg gaa ctg gat ggc gat gtg aat ggg cac aaa ttt         96
Val Pro Ile Leu Val Glu Leu Asp Gly Asp Val Asn Gly His Lys Phe
             20                  25                  30 tct gtc agc gga gag ggt gaa ggt gat gcc aca tac gga aag ctc acc        144
Ser Val Ser Gly Glu Gly Glu Gly Asp Ala Thr Tyr Gly Lys Leu Thr
         35                  40                  45 ctg aaa ttc atc tgc acc act gga aag ctc cct gtg cca tgg cca aca        192
Leu Lys Phe Ile Cys Thr Thr Gly Lys Leu Pro Val Pro Trp Pro Thr
     50                  55                  60 ctg gtc act acc ttc tct tat ggc gtg cag tgc ttt tcc aga tac cca        240
Leu Val Thr Thr Phe Ser Tyr Gly Val Gln Cys Phe Ser Arg Tyr Pro
 65                  70                  75                  80 gac cat atg aag cag cat gac ttt ttc aag agc gcc atg ccc gag ggc        288
Asp His Met Lys Gln His Asp Phe Phe Lys Ser Ala Met Pro Glu Gly
                 85                  90                  95 tat gtg cag gag aga acc atc ttt ttc aaa gat gac ggg aac tac aag        336
Tyr Val Gln Glu Arg Thr Ile Phe Phe Lys Asp Asp Gly Asn Tyr Lys
            100                 105                 110 acc cgc gct gaa gtc aag ttc gaa ggt gac acc ctg gtg aat aga atc        384
Thr Arg Ala Glu Val Lys Phe Glu Gly Asp Thr Leu Val Asn Arg Ile
        115                 120                 125 gag ctg aag ggc att gac ttt aag gag gat gga aac att ctc ggc cac        432
Glu Leu Lys Gly Ile Asp Phe Lys Glu Asp Gly Asn Ile Leu Gly His
    130                 135                 140 aag ctg gaa tac aac tat aac tcc cac aat gtg tac atc atg gcc gac        480
Lys Leu Glu Tyr Asn Tyr Asn Ser His Asn Val Tyr Ile Met Ala Asp
145                 150                 155                 160 aag caa aag aat ggc atc aag gtc aac ttc aag atc aga cac aac att        528
Lys Gln Lys Asn Gly Ile Lys Val Asn Phe Lys Ile Arg His Asn Ile
```

-continued

```
                   165                 170                 175
gag gat gga tcc gtg cag ctg gcc gac cat tat caa cag aac act cca        576
Glu Asp Gly Ser Val Gln Leu Ala Asp His Tyr Gln Gln Asn Thr Pro
            180                 185                 190 atc ggc gac ggc cct gtg ctc ctc cca gac aac cat tac ctg tcc acc        624
Ile Gly Asp Gly Pro Val Leu Leu Pro Asp Asn His Tyr Leu Ser Thr
        195                 200                 205 cag tct gcc ctg tct aaa gat ccc aac gaa aag aga gac cac atg gtc        672
Gln Ser Ala Leu Ser Lys Asp Pro Asn Glu Lys Arg Asp His Met Val
    210                 215                 220 ctg ctg gag ttt gtg acc gct gct ggg atc aca cat ggc atg gac gag        720
Leu Leu Glu Phe Val Thr Ala Ala Gly Ile Thr His Gly Met Asp Glu
225                 230                 235                 240 ctg tac aag tga                                                        732
Leu Tyr Lys <210> SEQ ID NO 158
<211> LENGTH: 717
<212> TYPE: DNA
<213> ORGANISM: Artificial Sequence
<220> FEATURE:
<223> OTHER INFORMATION: Description of Artificial Sequence:
      GFP humanized control
<220> FEATURE:
<221> NAME/KEY: CDS
<222> LOCATION: (1)..(717)

<400> SEQUENCE: 158 atg agc aag ggc gag gaa ctg ttc act ggc gtg gtc cca att ctc gtg         48
Met Ser Lys Gly Glu Glu Leu Phe Thr Gly Val Val Pro Ile Leu Val
  1               5                  10                  15 gaa ctg gat ggc gat gtg aat ggg cac aaa ttt tct gtc agc gga gag         96
Glu Leu Asp Gly Asp Val Asn Gly His Lys Phe Ser Val Ser Gly Glu
             20                  25                  30 ggt gaa ggt gat gcc aca tac gga aag ctc acc ctg aaa ttc atc tgc        144
Gly Glu Gly Asp Ala Thr Tyr Gly Lys Leu Thr Leu Lys Phe Ile Cys
         35                  40                  45 acc act gga aag ctc cct gtg cca tgg cca aca ctg gtc act acc ttc        192
Thr Thr Gly Lys Leu Pro Val Pro Trp Pro Thr Leu Val Thr Thr Phe
     50                  55                  60 tct tat ggc gtg cag tgc ttt tcc aga tac cca gac cat atg aag cag        240
Ser Tyr Gly Val Gln Cys Phe Ser Arg Tyr Pro Asp His Met Lys Gln
 65                  70                  75                  80 cat gac ttt ttc aag agc gcc atg ccc gag ggc tat gtg cag gag aga        288
His Asp Phe Phe Lys Ser Ala Met Pro Glu Gly Tyr Val Gln Glu Arg
                 85                  90                  95 acc atc ttt ttc aaa gat gac ggg aac tac aag acc cgc gct gaa gtc        336
Thr Ile Phe Phe Lys Asp Asp Gly Asn Tyr Lys Thr Arg Ala Glu Val
            100                 105                 110 aag ttc gaa ggt gac acc ctg gtg aat aga atc gag ctg aag ggc att        384
Lys Phe Glu Gly Asp Thr Leu Val Asn Arg Ile Glu Leu Lys Gly Ile
        115                 120                 125 gac ttt aag gag gat gga aac att ctc ggc cac aag ctg gaa tac aac        432
Asp Phe Lys Glu Asp Gly Asn Ile Leu Gly His Lys Leu Glu Tyr Asn
    130                 135                 140 tat aac tcc cac aat gtg tac atc atg gcc gac aag caa aag aat ggc        480
Tyr Asn Ser His Asn Val Tyr Ile Met Ala Asp Lys Gln Lys Asn Gly
145                 150                 155                 160 atc aag gtc aac ttc aag atc aga cac aac att gag gat gga tcc gtg        528
Ile Lys Val Asn Phe Lys Ile Arg His Asn Ile Glu Asp Gly Ser Val
                165                 170                 175
```

```
cag ctg gcc gac cat tat caa cag aac act cca atc ggc gac ggc cct      576
Gln Leu Ala Asp His Tyr Gln Gln Asn Thr Pro Ile Gly Asp Gly Pro
        180                 185                 190 gtg ctc ctc cca gac aac cat tac ctg tcc acc cag tct gcc ctg tct      624
Val Leu Leu Pro Asp Asn His Tyr Leu Ser Thr Gln Ser Ala Leu Ser
    195                 200                 205 aaa gat ccc aac gaa aag aga gac cac atg gtc ctg ctg gag ttt gtg      672
Lys Asp Pro Asn Glu Lys Arg Asp His Met Val Leu Leu Glu Phe Val
210                 215                 220 acc gct gct ggg atc aca cat ggc atg gac gag ctg tac aag tga          717
Thr Ala Ala Gly Ile Thr His Gly Met Asp Glu Leu Tyr Lys
225                 230                 235

<210> SEQ ID NO 159
<211> LENGTH: 238
<212> TYPE: PRT
<213> ORGANISM: Artificial Sequence
<220> FEATURE:
<223> OTHER INFORMATION: Description of Artificial Sequence: GFP
      humanized control

<400> SEQUENCE: 159

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 160
<211> LENGTH: 54
<212> TYPE: DNA
<213> ORGANISM: Artificial Sequence
<220> FEATURE:
<223> OTHER INFORMATION: Description of Artificial Sequence: Ala(GCA)5
```

-continued primer

<400> SEQUENCE: 160
cggggtacca tggcagcagc agcagcaagc aagggcgagg aactgttcac tggc      54

<210> SEQ ID NO 161
<211> LENGTH: 54
<212> TYPE: DNA
<213> ORGANISM: Artificial Sequence
<220> FEATURE:
<223> OTHER INFORMATION: Description of Artificial Sequence: Ala(GCC)5
      primer

<400> SEQUENCE: 161
cggggtacca tggccgccgc cgccgccagc aagggcgagg aactgttcac tggc      54

<210> SEQ ID NO 162
<211> LENGTH: 54
<212> TYPE: DNA
<213> ORGANISM: Artificial Sequence
<220> FEATURE:
<223> OTHER INFORMATION: Description of Artificial Sequence: Ala(GCG)5
      primer

<400> SEQUENCE: 162
cggggtacca tggcggcggc ggcggcgagc aagggcgagg aactgttcac tggc      54

<210> SEQ ID NO 163
<211> LENGTH: 54
<212> TYPE: DNA
<213> ORGANISM: Artificial Sequence
<220> FEATURE:
<223> OTHER INFORMATION: Description of Artificial Sequence: Ala(GCT)5
      primer

<400> SEQUENCE: 163
cggggtacca tggctgctgc tgctgctagc aagggcgagg aactgttcac tggc      54

<210> SEQ ID NO 164
<211> LENGTH: 54
<212> TYPE: DNA
<213> ORGANISM: Artificial Sequence
<220> FEATURE:
<223> OTHER INFORMATION: Description of Artificial Sequence: Arg(AGA)5
      primer

<400> SEQUENCE: 164
cggggtacca tgagaagaag aagaagaagc aagggcgagg aactgttcac tggc      54

<210> SEQ ID NO 165
<211> LENGTH: 54
<212> TYPE: DNA
<213> ORGANISM: Artificial Sequence
<220> FEATURE:
<223> OTHER INFORMATION: Description of Artificial Sequence: Arg(AGG)5
      primer

<400> SEQUENCE: 165
cggggtacca tgaggaggag gaggaggagc aagggcgagg aactgttcac tggc      54

<210> SEQ ID NO 166
<211> LENGTH: 54
<212> TYPE: DNA
<213> ORGANISM: Artificial Sequence
<220> FEATURE:
<223> OTHER INFORMATION: Description of Artificial Sequence: Arg(CGA)5
      primer

<400> SEQUENCE: 166
cggggtacca tgcgacgacg acgacgaagc aagggcgagg aactgttcac tggc        54

<210> SEQ ID NO 167
<211> LENGTH: 54
<212> TYPE: DNA
<213> ORGANISM: Artificial Sequence
<220> FEATURE:
<223> OTHER INFORMATION: Description of Artificial Sequence: Arg(CGC)5
      primer

<400> SEQUENCE: 167
cggggtacca tgcgccgccg ccgccgcagc aagggcgagg aactgttcac tggc        54

<210> SEQ ID NO 168
<211> LENGTH: 54
<212> TYPE: DNA
<213> ORGANISM: Artificial Sequence
<220> FEATURE:
<223> OTHER INFORMATION: Description of Artificial Sequence: Arg(CGG)5
      primer

<400> SEQUENCE: 168
cggggtacca tgcggcggcg gcggcggagc aagggcgagg aactgttcac tggc        54

<210> SEQ ID NO 169
<211> LENGTH: 54
<212> TYPE: DNA
<213> ORGANISM: Artificial Sequence
<220> FEATURE:
<223> OTHER INFORMATION: Description of Artificial Sequence: arg(CGT)5
      primer

<400> SEQUENCE: 169
cggggtacca tgcgtcgtcg tcgtcgtagc aagggcgagg aactgttcac tggc        54

<210> SEQ ID NO 170
<211> LENGTH: 54
<212> TYPE: DNA
<213> ORGANISM: Artificial Sequence
<220> FEATURE:
<223> OTHER INFORMATION: Description of Artificial Sequence: Asn(AAC)5
      primer

<400> SEQUENCE: 170
cggggtacca tgaacaacaa caacaacagc aagggcgagg aactgttcac tggc        54

<210> SEQ ID NO 171
<211> LENGTH: 54
<212> TYPE: DNA
<213> ORGANISM: Artificial Sequence
<220> FEATURE:
<223> OTHER INFORMATION: Description of Artificial Sequence: Asn(AAT)5
      primer

<400> SEQUENCE: 171
cggggtacca tgaataataa taataatagc aagggcgagg aactgttcac tggc        54

<210> SEQ ID NO 172
<211> LENGTH: 54
<212> TYPE: DNA
<213> ORGANISM: Artificial Sequence
<220> FEATURE:
<223> OTHER INFORMATION: Description of Artificial Sequence: Asp(GAC)5
      primer

<400> SEQUENCE: 172
cggggtacca tggacgacga cgacgacagc aagggcgagg aactgttcac tggc    54

<210> SEQ ID NO 173
<211> LENGTH: 54
<212> TYPE: DNA
<213> ORGANISM: Artificial Sequence
<220> FEATURE:
<223> OTHER INFORMATION: Description of Artificial Sequence: Asp(GAT)5
      primer

<400> SEQUENCE: 173
cggggtacca tggatgatga tgatgatagc aagggcgagg aactgttcac tggc    54

<210> SEQ ID NO 174
<211> LENGTH: 54
<212> TYPE: DNA
<213> ORGANISM: Artificial Sequence
<220> FEATURE:
<223> OTHER INFORMATION: Description of Artificial Sequence: Cys(TGC)5
      primer

<400> SEQUENCE: 174
cggggtacca tgtgctgctg ctgctgcagc aagggcgagg aactgttcac tggc    54

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Cys(TGT)5
      primer

<400> SEQUENCE: 175
cggggtacca tgtgttgttg ttgttgtagc aagggcgagg aactgttcac tggc    54

<210> SEQ ID NO 176
<211> LENGTH: 54
<212> TYPE: DNA
<213> ORGANISM: Artificial Sequence
<220> FEATURE:
<223> OTHER INFORMATION: Description of Artificial Sequence: Gln(CAA)5
      primer

<400> SEQUENCE: 176
cggggtacca tgcaacaaca acaacaaagc aagggcgagg aactgttcac tggc    54

<210> SEQ ID NO 177
<211> LENGTH: 54
<212> TYPE: DNA
<213> ORGANISM: Artificial Sequence
<220> FEATURE:
<223> OTHER INFORMATION: Description of Artificial Sequence: Gln(CAG)5
      primer

<400> SEQUENCE: 177
cggggtacca tgcagcagca gcagcagagc aagggcgagg aactgttcac tggc    54

<210> SEQ ID NO 178
<211> LENGTH: 54
<212> TYPE: DNA
<213> ORGANISM: Artificial Sequence
<220> FEATURE:
<223> OTHER INFORMATION: Description of Artificial Sequence: Glu(GAA)5
      primer

<400> SEQUENCE: 178
cggggtacca tggaagaaga agaagaaagc aagggcgagg aactgttcac tggc          54

<210> SEQ ID NO 179
<211> LENGTH: 54
<212> TYPE: DNA
<213> ORGANISM: Artificial Sequence
<220> FEATURE:
<223> OTHER INFORMATION: Description of Artificial Sequence: Glu(GAG)5
      primer

<400> SEQUENCE: 179
cggggtacca tggaggagga ggaggagagc aagggcgagg aactgttcac tggc          54

<210> SEQ ID NO 180
<211> LENGTH: 54
<212> TYPE: DNA
<213> ORGANISM: Artificial Sequence
<220> FEATURE:
<223> OTHER INFORMATION: Description of Artificial Sequence: Gly(GGA)5
      primer

<400> SEQUENCE: 180
cggggtacca tgggaggagg aggaggaagc aagggcgagg aactgttcac tggc          54

<210> SEQ ID NO 181
<211> LENGTH: 54
<212> TYPE: DNA
<213> ORGANISM: Artificial Sequence
<220> FEATURE:
<223> OTHER INFORMATION: Description of Artificial Sequence: Gly(GGC)5
      primer

<400> SEQUENCE: 181
cggggtacca tgggcggcgg cggcggcagc aagggcgagg aactgttcac tggc          54

<210> SEQ ID NO 182
<211> LENGTH: 54
<212> TYPE: DNA
<213> ORGANISM: Artificial Sequence
<220> FEATURE:
<223> OTHER INFORMATION: Description of Artificial Sequence: Gly(GGG)5
      primer

<400> SEQUENCE: 182
cggggtacca tgggggggggg gggggggagc aagggcgagg aactgttcac tggc          54

<210> SEQ ID NO 183
<211> LENGTH: 54
<212> TYPE: DNA
<213> ORGANISM: Artificial Sequence
<220> FEATURE:
<223> OTHER INFORMATION: Description of Artificial Sequence: Gly(GGT)5
      primer

<400> SEQUENCE: 183
cggggtacca tgggtggtgg tggtggtagc aagggcgagg aactgttcac tggc          54

<210> SEQ ID NO 184
<211> LENGTH: 54
<212> TYPE: DNA
<213> ORGANISM: Artificial Sequence
<220> FEATURE:
<223> OTHER INFORMATION: Description of Artificial Sequence: His(CAC)5
      primer

<400> SEQUENCE: 184
cggggtacca tgcaccacca ccaccacagc aagggcgagg aactgttcac tggc    54

<210> SEQ ID NO 185
<211> LENGTH: 54
<212> TYPE: DNA
<213> ORGANISM: Artificial Sequence
<220> FEATURE:
<223> OTHER INFORMATION: Description of Artificial Sequence: His(CAT)5
      primer

<400> SEQUENCE: 185
cggggtacca tgcatcatca tcatcatagc aagggcgagg aactgttcac tggc    54

<210> SEQ ID NO 186
<211> LENGTH: 54
<212> TYPE: DNA
<213> ORGANISM: Artificial Sequence
<220> FEATURE:
<223> OTHER INFORMATION: Description of Artificial Sequence: Ile(ATA)5
      primer

<400> SEQUENCE: 186
cggggtacca tgataataat aataataagc aagggcgagg aactgttcac tggc    54

<210> SEQ ID NO 187
<211> LENGTH: 54
<212> TYPE: DNA
<213> ORGANISM: Artificial Sequence
<220> FEATURE:
<223> OTHER INFORMATION: Description of Artificial Sequence: Ile(ATC)5
      primer

<400> SEQUENCE: 187
cggggtacca tgatcatcat catcatcagc aagggcgagg aactgttcac tggc    54

<210> SEQ ID NO 188
<211> LENGTH: 54
<212> TYPE: DNA
<213> ORGANISM: Artificial Sequence
<220> FEATURE:
<223> OTHER INFORMATION: Description of Artificial Sequence: Ile(ATT)5
      primer

<400> SEQUENCE: 188
cggggtacca tgattattat tattattagc aagggcgagg aactgttcac tggc    54

<210> SEQ ID NO 189
<211> LENGTH: 54
<212> TYPE: DNA
<213> ORGANISM: Artificial Sequence
<220> FEATURE:
<223> OTHER INFORMATION: Description of Artificial Sequence: Leu(CTA)5
      primer

<400> SEQUENCE: 189
cggggtacca tgctactact actactaagc aagggcgagg aactgttcac tggc    54

<210> SEQ ID NO 190
<211> LENGTH: 54
<212> TYPE: DNA
<213> ORGANISM: Artificial Sequence
<220> FEATURE:
<223> OTHER INFORMATION: Description of Artificial Sequence: Leu(CTC)5
      primer

<400> SEQUENCE: 190
cggggtacca tgctcctcct cctcctcagc aagggcgagg aactgttcac tggc    54

<210> SEQ ID NO 191
<211> LENGTH: 54
<212> TYPE: DNA
<213> ORGANISM: Artificial Sequence
<220> FEATURE:
<223> OTHER INFORMATION: Description of Artificial Sequence: Leu(CTG)5
      primer

<400> SEQUENCE: 191
cggggtacca tgctgctgct gctgctgagc aagggcgagg aactgttcac tggc        54

<210> SEQ ID NO 192
<211> LENGTH: 54
<212> TYPE: DNA
<213> ORGANISM: Artificial Sequence
<220> FEATURE:
<223> OTHER INFORMATION: Description of Artificial Sequence: Leu(CTT)5
      primer

<400> SEQUENCE: 192
cggggtacca tgcttcttct tcttcttagc aagggcgagg aactgttcac tggc        54

<210> SEQ ID NO 193
<211> LENGTH: 54
<212> TYPE: DNA
<213> ORGANISM: Artificial Sequence
<220> FEATURE:
<223> OTHER INFORMATION: Description of Artificial Sequence: Leu(TTA)5
      primer

<400> SEQUENCE: 193
cggggtacca tgttattatt attattaagc aagggcgagg aactgttcac tggc        54

<210> SEQ ID NO 194
<211> LENGTH: 54
<212> TYPE: DNA
<213> ORGANISM: Artificial Sequence
<220> FEATURE:
<223> OTHER INFORMATION: Description of Artificial Sequence: Leu(TTG)5
      primer

<400> SEQUENCE: 194
cggggtacca tgttgttgtt gttgttgagc aagggcgagg aactgttcac tggc        54

<210> SEQ ID NO 195
<211> LENGTH: 54
<212> TYPE: DNA
<213> ORGANISM: Artificial Sequence
<220> FEATURE:
<223> OTHER INFORMATION: Description of Artificial Sequence: Lys(AAA)5
      primer

<400> SEQUENCE: 195
cggggtacca tgaaaaaaaa aaaaaaaagc aagggcgagg aactgttcac tggc        54

<210> SEQ ID NO 196
<211> LENGTH: 54
<212> TYPE: DNA
<213> ORGANISM: Artificial Sequence
<220> FEATURE:
<223> OTHER INFORMATION: Description of Artificial Sequence: Lys(AAG)5
      primer

<400> SEQUENCE: 196
cggggtacca tgaagaagaa gaagaagagc aagggcgagg aactgttcac tggc        54

<210> SEQ ID NO 197
<211> LENGTH: 54
<212> TYPE: DNA
<213> ORGANISM: Artificial Sequence
<220> FEATURE:
<223> OTHER INFORMATION: Description of Artificial Sequence: Phe(CTT)5
      primer

<400> SEQUENCE: 197
cggggtacca tgcttcttct tcttcttagc aagggcgagg aactgttcac tggc         54

<210> SEQ ID NO 198
<211> LENGTH: 54
<212> TYPE: DNA
<213> ORGANISM: Artificial Sequence
<220> FEATURE:
<223> OTHER INFORMATION: Description of Artificial Sequence: Phe(TTC)5
      primer

<400> SEQUENCE: 198
cggggtacca tgttcttctt cttcttcagc aagggcgagg aactgttcac tggc         54

<210> SEQ ID NO 199
<211> LENGTH: 54
<212> TYPE: DNA
<213> ORGANISM: Artificial Sequence
<220> FEATURE:
<223> OTHER INFORMATION: Description of Artificial Sequence: Pro(CCC)5
      primer

<400> SEQUENCE: 199
cggggtacca tgcccccccc ccccccagc aagggcgagg aactgttcac tggc          54

<210> SEQ ID NO 200
<211> LENGTH: 54
<212> TYPE: DNA
<213> ORGANISM: Artificial Sequence
<220> FEATURE:
<223> OTHER INFORMATION: Description of Artificial Sequence: Pro(CCG)5
      primer

<400> SEQUENCE: 200
cggggtacca tgccgccgcc gccgccgagc aagggcgagg aactgttcac tggc         54

<210> SEQ ID NO 201
<211> LENGTH: 54
<212> TYPE: DNA
<213> ORGANISM: Artificial Sequence
<220> FEATURE:
<223> OTHER INFORMATION: Description of Artificial Sequence: Pro(CCT)5
      primer

<400> SEQUENCE: 201
cggggtacca tgcctcctcc tcctcctagc aagggcgagg aactgttcac tggc         54

<210> SEQ ID NO 202
<211> LENGTH: 54
<212> TYPE: DNA
<213> ORGANISM: Artificial Sequence
<220> FEATURE:
<223> OTHER INFORMATION: Description of Artificial Sequence: Pro(CGA)5
      primer

<400> SEQUENCE: 202
cggggtacca tgcgacgacg acgacgaagc aagggcgagg aactgttcac tggc         54

```
<210> SEQ ID NO 203
<211> LENGTH: 54
<212> TYPE: DNA
<213> ORGANISM: Artificial Sequence
<220> FEATURE:
<223> OTHER INFORMATION: Description of Artificial Sequence: Ser(AGC)5
      primer

<400> SEQUENCE: 203
cggggtacca tgagcagcag cagcagcagc aagggcgagg aactgttcac tggc          54

<210> SEQ ID NO 204
<211> LENGTH: 54
<212> TYPE: DNA
<213> ORGANISM: Artificial Sequence
<220> FEATURE:
<223> OTHER INFORMATION: Description of Artificial Sequence: Ser(AGT)5
      primer

<400> SEQUENCE: 204
cggggtacca tgagtagtag tagtagtagc aagggcgagg aactgttcac tggc          54

<210> SEQ ID NO 205
<211> LENGTH: 54
<212> TYPE: DNA
<213> ORGANISM: Artificial Sequence
<220> FEATURE:
<223> OTHER INFORMATION: Description of Artificial Sequence: Ser(TCA)5
      primer

<400> SEQUENCE: 205
cggggtacca tgtcatcatc atcatcaagc aagggcgagg aactgttcac tggc          54

<210> SEQ ID NO 206
<211> LENGTH: 54
<212> TYPE: DNA
<213> ORGANISM: Artificial Sequence
<220> FEATURE:
<223> OTHER INFORMATION: Description of Artificial Sequence: Ser(TCC)5
      primer

<400> SEQUENCE: 206
cggggtacca tgtcctcctc ctcctccagc aagggcgagg aactgttcac tggc          54

<210> SEQ ID NO 207
<211> LENGTH: 54
<212> TYPE: DNA
<213> ORGANISM: Artificial Sequence
<220> FEATURE:
<223> OTHER INFORMATION: Description of Artificial Sequence: Ser(TCG)5
      primer

<400> SEQUENCE: 207
cggggtacca tgtcgtcgtc gtcgtcgagc aagggcgagg aactgttcac tggc          54

<210> SEQ ID NO 208
<211> LENGTH: 54
<212> TYPE: DNA
<213> ORGANISM: Artificial Sequence
<220> FEATURE:
<223> OTHER INFORMATION: Description of Artificial Sequence: Ser(TCT)5
      primer

<400> SEQUENCE: 208
cggggtacca tgtcttcttc ttcttctagc aagggcgagg aactgttcac tggc          54

<210> SEQ ID NO 209
```

<210> SEQ ID NO 209
<211> LENGTH: 54
<212> TYPE: DNA
<213> ORGANISM: Artificial Sequence
<220> FEATURE:
<223> OTHER INFORMATION: Description of Artificial Sequence: Thr(ACA)5
      primer

<400> SEQUENCE: 209
cggggtacca tgacaacaac aacaacaagc aagggcgagg aactgttcac tggc         54

<210> SEQ ID NO 210
<211> LENGTH: 54
<212> TYPE: DNA
<213> ORGANISM: Artificial Sequence
<220> FEATURE:
<223> OTHER INFORMATION: Description of Artificial Sequence: Thr(ACC)5
      primer

<400> SEQUENCE: 210
cggggtacca tgaccaccac caccaccagc aagggcgagg aactgttcac tggc         54

<210> SEQ ID NO 211
<211> LENGTH: 54
<212> TYPE: DNA
<213> ORGANISM: Artificial Sequence
<220> FEATURE:
<223> OTHER INFORMATION: Description of Artificial Sequence: Thr(ACG)5
      primer

<400> SEQUENCE: 211
cggggtacca tgacgacgac gacgacgagc aagggcgagg aactgttcac tggc         54

<210> SEQ ID NO 212
<211> LENGTH: 54
<212> TYPE: DNA
<213> ORGANISM: Artificial Sequence
<220> FEATURE:
<223> OTHER INFORMATION: Description of Artificial Sequence: Thr(ACT)5
      primer

<400> SEQUENCE: 212
cggggtacca tgactactac tactactagc aagggcgagg aactgttcac tggc         54

<210> SEQ ID NO 213
<211> LENGTH: 54
<212> TYPE: DNA
<213> ORGANISM: Artificial Sequence
<220> FEATURE:
<223> OTHER INFORMATION: Description of Artificial Sequence: Trp(TGG)5
      primer

<400> SEQUENCE: 213
cggggtacca tgtggtggtg gtggtggagc aagggcgagg aactgttcac tggc         54

<210> SEQ ID NO 214
<211> LENGTH: 54
<212> TYPE: DNA
<213> ORGANISM: Artificial Sequence
<220> FEATURE:
<223> OTHER INFORMATION: Description of Artificial Sequence: Tyr(TAT)5
      primer

<400> SEQUENCE: 214
cggggtacca tgtattatta ttattatagc aagggcgagg aactgttcac tggc         54

<210> SEQ ID NO 215
<211> LENGTH: 54

```
<212> TYPE: DNA
<213> ORGANISM: Artificial Sequence
<220> FEATURE:
<223> OTHER INFORMATION: Description of Artificial Sequence: Val(GTA)5
      primer

<400> SEQUENCE: 215
cggggtacca tggtagtagt agtagtaagc aagggcgagg aactgttcac tggc        54

<210> SEQ ID NO 216
<211> LENGTH: 54
<212> TYPE: DNA
<213> ORGANISM: Artificial Sequence
<220> FEATURE:
<223> OTHER INFORMATION: Description of Artificial Sequence: Val(GTC)5
      primer

<400> SEQUENCE: 216
cggggtacca tggtcgtcgt cgtcgtcagc aagggcgagg aactgttcac tggc        54

<210> SEQ ID NO 217
<211> LENGTH: 54
<212> TYPE: DNA
<213> ORGANISM: Artificial Sequence
<220> FEATURE:
<223> OTHER INFORMATION: Description of Artificial Sequence: Val(GTG)5
      primer

<400> SEQUENCE: 217
cggggtacca tggtggtggt ggtggtgagc aagggcgagg aactgttcac tggc        54

<210> SEQ ID NO 218
<211> LENGTH: 54
<212> TYPE: DNA
<213> ORGANISM: Artificial Sequence
<220> FEATURE:
<223> OTHER INFORMATION: Description of Artificial Sequence: Val(GTT)5
      primer

<400> SEQUENCE: 218
cggggtacca tggttgttgt tgttgttagc aagggcgagg aactgttcac tggc        54

<210> SEQ ID NO 219
<211> LENGTH: 33
<212> TYPE: DNA
<213> ORGANISM: Artificial Sequence
<220> FEATURE:
<223> OTHER INFORMATION: Description of Artificial Sequence: 3'
      oligonucleotide common primer

<400> SEQUENCE: 219
ccggaattct cacttgtaca ggtggtccat gcc                              33
```